US009226883B2

(12) United States Patent
Sabelle et al.

(10) Patent No.: US 9,226,883 B2
(45) Date of Patent: Jan. 5, 2016

(54) PARTICULAR AZOMETHINE DIRECT DYES, DYE COMPOSITION COMPRISING AT LEAST ONE SUCH COMPOUND, IMPLEMENTATION PROCESS THEREFORE AND USE THEREOF

(71) Applicant: L'OREAL, Paris (FR)

(72) Inventors: Stephane Sabelle, Paris (FR); Madeleine Leduc, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/365,211

(22) PCT Filed: Dec. 11, 2012

(86) PCT No.: PCT/EP2012/075103
§ 371 (c)(1),
(2) Date: Jun. 13, 2014

(87) PCT Pub. No.: WO2013/087636
PCT Pub. Date: Jun. 20, 2013

(65) Prior Publication Data
US 2015/0000688 A1    Jan. 1, 2015

Related U.S. Application Data

(60) Provisional application No. 61/584,987, filed on Jan. 10, 2012.

(30) Foreign Application Priority Data

Dec. 13, 2011  (FR) ..................... 11 61573

(51) Int. Cl.
| | |
|---|---|
| A61Q 5/10 | (2006.01) |
| A61K 8/41 | (2006.01) |
| C09B 55/00 | (2006.01) |
| A61Q 5/06 | (2006.01) |
| A61K 8/34 | (2006.01) |
| A61K 8/35 | (2006.01) |
| A61K 8/42 | (2006.01) |
| A45D 19/00 | (2006.01) |
| A45D 34/00 | (2006.01) |
| A61K 8/368 | (2006.01) |

(52) U.S. Cl.
CPC .............. *A61K 8/415* (2013.01); *A45D 19/00* (2013.01); *A45D 34/00* (2013.01); *A61K 8/34* (2013.01); *A61K 8/342* (2013.01); *A61K 8/35* (2013.01); *A61K 8/368* (2013.01); *A61K 8/41* (2013.01); *A61K 8/411* (2013.01); *A61K 8/416* (2013.01); *A61K 8/42* (2013.01); *A61Q 5/06* (2013.01); *A61Q 5/065* (2013.01); *A61Q 5/10* (2013.01); *C09B 55/009* (2013.01); *A61K 2800/4322* (2013.01)

(58) Field of Classification Search
USPC ............................................... 8/405
See application file for complete search history.

(56) References Cited

U.S. PATENT DOCUMENTS

| | | | |
|---|---|---|---|
| 3,787,174 A | 1/1974 | Kalopissis et al. |
| 3,792,090 A | 2/1974 | Kalopissis et al. |
| 3,817,699 A | 6/1974 | Kalopissis et al. |
| 3,853,464 A | 12/1974 | Kalopissis et al. |
| 3,867,094 A | 2/1975 | Kalopissis et al. |
| 3,884,625 A | 5/1975 | Kalopissis et al. |
| 3,894,837 A | 7/1975 | Kalopissis et al. |
| 3,905,761 A | 9/1975 | Kalopissis et al. |
| 3,929,404 A | 12/1975 | Kalopissis et al. |
| 3,953,508 A | 4/1976 | Kalopissis et al. |
| 3,963,764 A | 6/1976 | Kalopissis et al. |
| 3,972,937 A | 8/1976 | Kalopissis et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

STIC Search Report dated Feb. 25, 2015.*
International Search Report for PCT/EP2012/075103, (Jan. 2013).
English language abstract for EP 0770375A1, (1997).
English language abstract for FR 2886136A1, (2006).
English language abstract for JP 02019576A, (1990).
English language abstract for JP 05163124A, (1993).

*Primary Examiner* — Eisa Elhilo
(74) *Attorney, Agent, or Firm* — The Marbury Law Group, PLLC

(57) ABSTRACT

The present invention relates to direct dyes of azomethine type of formula (I) below; and also to the use thereof for dyeing keratin fibers, in particular human keratin fibers such as the hair. The invention also relates to a composition for dyeing keratin fibers, comprising such direct dyes in a suitable dyeing medium. Similarly, a subject of the invention is a process for dyeing keratin fibers using the said dye composition, and also a device comprising the same. Finally, the present invention also relates to precursors of these direct dyes.

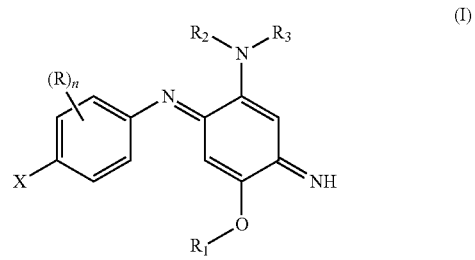

5 Claims, No Drawings

(56) References Cited

U.S. PATENT DOCUMENTS

| | | |
|---|---|---|
| 3,984,402 A | 10/1976 | Kalopissis et al. |
| 3,984,443 A * | 10/1976 | Kalopissis et al. ............ 552/301 |
| 4,003,699 A | 1/1977 | Rose et al. |
| 4,042,627 A * | 8/1977 | Kalopissis et al. ............ 564/434 |
| 4,045,170 A | 8/1977 | Kalopissis et al. |
| 4,046,786 A | 9/1977 | Kalopissis et al. |
| 4,054,147 A | 10/1977 | Kalopissis et al. |
| 4,093,806 A | 6/1978 | Kalopissis et al. |
| 4,112,229 A | 9/1978 | Kalopissis et al. |
| RE30,199 E | 1/1980 | Rose et al. |
| 4,222,958 A | 9/1980 | Kalopissis et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,730,789 B1 | 5/2004 | Birault et al. |
| 2002/0050013 A1 | 5/2002 | Vidal et al. |
| 2003/0019051 A9 | 1/2003 | Vidal et al. |

FOREIGN PATENT DOCUMENTS

| | | |
|---|---|---|
| DE | 4133957 A1 | 4/1993 |
| DE | 19543988 A1 | 5/1997 |
| EP | 0714954 A2 | 6/1996 |
| EP | 0770375 A1 | 5/1997 |
| FR | 2047932 A1 | 3/1971 |
| FR | 2056799 A5 | 5/1971 |
| FR | 2106661 A5 | 5/1972 |
| FR | 2121101 A5 | 8/1972 |
| FR | 2165965 A1 | 8/1973 |
| FR | 2234277 A1 | 1/1975 |
| FR | 2262023 A1 | 9/1975 |
| FR | 2733749 A1 | 11/1996 |
| FR | 2801308 A1 | 2/2001 |
| FR | 2886136 A1 | 12/2006 |
| GB | 1026978 A | 4/1966 |
| GB | 1153196 A | 5/1969 |
| GB | 1323805 A | 7/1973 |
| JP | 02019576 A | 1/1990 |
| JP | 5163124 | 6/1993 |
| WO | 9408969 A1 | 4/1994 |
| WO | 9408970 A1 | 4/1994 |
| WO | 9501772 A1 | 1/1995 |
| WO | 9615765 A1 | 5/1995 |
| WO | 9515144 A1 | 6/1995 |

* cited by examiner

PARTICULAR AZOMETHINE DIRECT DYES, DYE COMPOSITION COMPRISING AT LEAST ONE SUCH COMPOUND, IMPLEMENTATION PROCESS THEREFORE AND USE THEREOF

CROSS REFERENCE TO RELATED APPLICATIONS

This is a national stage application of PCT/EP2012/075103, filed internationally on Dec. 11, 2012, which claims priority to U.S. Provisional Application No. 61/584,987, filed on Jan. 10, 2012, as well as French Application No. FR 1161573, filed Dec. 13, 2011, all of which are incorporated herein by their entireties.

The present invention relates to particular direct dyes of azomethine type and also to the use thereof for dyeing keratin fibres, in particular human keratin fibres such as the hair. The present invention also relates to a composition for dyeing keratin fibres, comprising such direct dyes in a suitable dyeing medium.

Similarly, a subject of the invention is a process for dyeing keratin fibres using the said dye composition, and also a device comprising the same.

Finally, the present invention also relates to precursors of these direct dyes.

The present invention relates to the field of dyeing keratin fibres and more particularly to the field of hair dyeing.

It is known practice to dye keratin fibres, and in particular the hair, with dye compositions containing one or more direct dyes, according to a "direct dyeing" process.

The process conventionally used in direct dyeing consists in applying to keratin fibres one or more direct dyes, or colouring molecules, which have affinity for the said fibres, leaving them to stand on the fibres, and then rinsing the fibres. The direct dyes used hitherto are generally nitrobenzene dyes, anthraquinone dyes, nitropyridine dyes, dyes of azo, xanthene, acridine or azine type or triarylmethane-based dyes.

These direct dyes may also be applied to keratin fibres in the presence of an oxidizing agent if it is desired to obtain simultaneous lightening of the fibres.

However, the colorations resulting therefrom are temporary or semi-permanent since the nature of the interactions that bind the direct dyes to the keratin fibre and their desorption from the surface and/or the core of the fibre are responsible for their weak dyeing power and their poor fastness with respect to washing, inclement weather or perspiration.

Moreover, such direct dyes are generally sensitive to the action of oxidizing agents such as aqueous hydrogen peroxide solution, which makes them difficult to use in lightening direct dye compositions that are formulated with aqueous hydrogen peroxide solution and a basifying agent, these compositions resembling the compositions used for oxidation dyeing. In other words, direct dyes are generally sparingly compatible with dye compositions intended for lightening fibres, and, consequently, their use in a lightening dyeing process, as an alternative to oxidation dyeing, is unsatisfactory.

These dyes also have the drawback of lacking light-fastness, on account of the poor resistance of the chromophore to photochemical attack. This lack of stability may lead in certain cases to fading over time of the coloration of the keratin fibres.

There is thus a real need for direct dyes that can not only dye keratin fibres satisfactorily, but that are also light-fast, capable of giving colorations that are both resistant to the various attacking factors to which the fibres may be subjected, such as inclement weather, sunlight, washing and perspiration, and that are also sufficiently stable in the presence of oxidizing agents such as aqueous hydrogen peroxide solution in order to be able to obtain simultaneous lightening of the fibre with the advantages outlined above.

These aims are achieved with the present invention, one subject of which is especially direct dyes of azomethine type of formula (I) below, organic or mineral acid salts thereof, tautomeric forms, optical isomers or geometrical isomers thereof and solvates thereof:

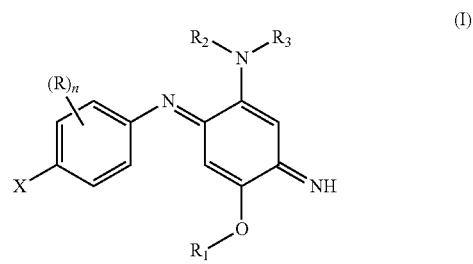

in which formula (I):

n represents an integer equal to 0, 1, 2, 3 or 4.

R represents:
  a linear or branched $C_1$-$C_4$ alkyl radical, optionally substituted with one or more identical or different radicals chosen from hydroxyl or imidazolium radicals, An$^-$; An$^-$ denoting a cosmetically acceptable anion or mixture of anions.
  a $C_1$-$C_4$ alkoxy radical.
  a halogen atom.

$R_1$ represents:
  a linear or branched $C_1$-$C_{10}$ alkyl radical, optionally substituted with one or more hydroxyl radicals, $R_2$ and $R_3$ represent, independently of each other:
  a hydrogen atom,
  a linear or branched $C_1$-$C_4$ alkyl radical, optionally substituted with one or more hydroxyl radicals, $R_2$ and $R_3$ can form, together with the nitrogen atom to which they are attached, a pyrrolidino, piperidino or morpholino ring, X represents:
  a hydroxyl radical,
  a radical —$NR_4R_5$ in which $R_4$ and $R_5$ represent, independently of each other:
    a hydrogen atom,
    a linear or branched $C_1$-$C_6$ alkyl radical, optionally substituted with one or more hydroxyl or $C_1$-$C_4$ alkoxy radicals, it being understood that the compounds of formula (I) cannot represent the following compounds (A), (B), (C), (D) or (E):

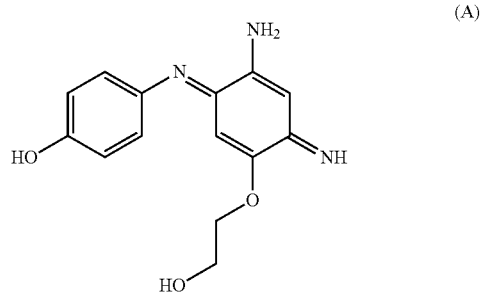

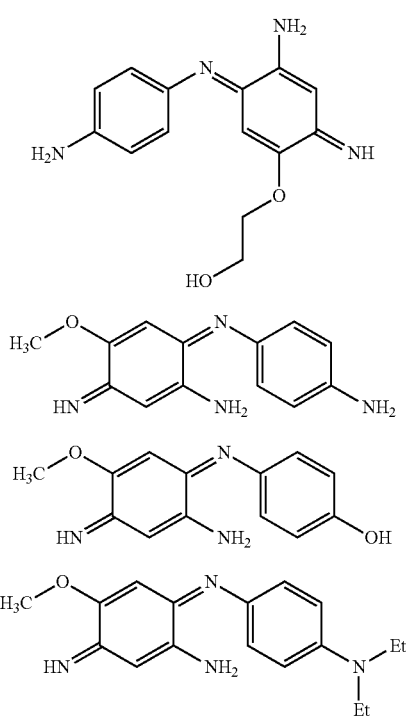

In a preferred embodiment according to the invention, direct dyes of azomethine type are of formula (I) below, organic or mineral acid salts thereof, tautomeric forms, optical isomers or geometrical isomers thereof and solvates thereof:

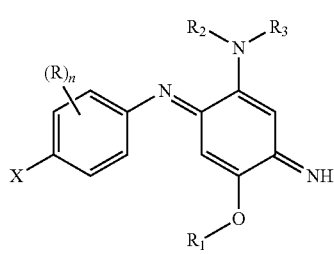

in which formula (I):
n represents an integer equal to 0, 1, 2, 3 or 4.
R represents:
- a linear or branched $C_1$-$C_4$ alkyl radical, optionally substituted with one or more identical or different radicals chosen from hydroxyl or imidazolium radicals, $An^-$; $An^-$ denoting a cosmetically acceptable anion or mixture of anions.
- a $C_1$-$C_4$ alkoxy radical.
- a halogen atom.

$R_1$ represents:
- a linear or branched $C_2$-$C_8$ alkyl radical, optionally substituted with one or more hydroxyl radicals, $R_2$ and $R_3$ represent, independently of each other:
- a hydrogen atom,
- a linear or branched $C_1$-$C_4$ alkyl radical, optionally substituted with one or more hydroxyl radicals, $R_2$ and $R_3$ can form, together with the nitrogen atom to which they are attached, a pyrrolidino, piperidino or morpholino ring, X represents:
- a hydroxyl radical,
- a radical —$NR_4R_5$ in which $R_4$ and $R_5$ represent, independently of each other:
  - a hydrogen atom,
  - a linear or branched $C_1$-$C_6$ alkyl radical, optionally substituted with one or more hydroxyl or $C_1$-$C_4$ alkoxy radicals, it being understood that the compounds of formula (I) cannot represent the following compounds (A) or (B):

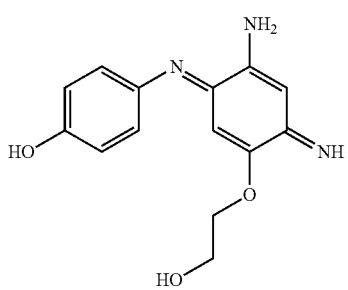

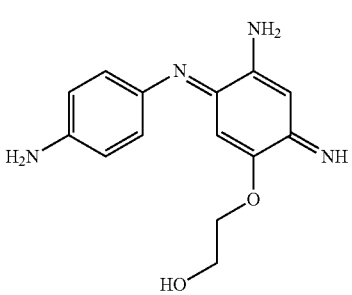

Another subject of the present invention concerns the use of one or more direct dyes of azomethine type of formula (I) as defined previously for the dyeing of keratin fibres, in particular human keratin fibres such as the hair.

The present invention also relates to a keratin fibre dye composition comprising, in a suitable dyeing medium, one or more direct dyes of azomethine type of formula (I) as defined previously.

In particular, the invention also relates to the use of the said dye composition for dyeing keratin fibres.

A subject of the invention is also a process for dyeing keratin fibres, in particular human keratin fibres such as the hair, in which the said dye composition according to the invention is applied to the said fibres for a time that is sufficient to obtain the desired coloration, after which the resulting fibres are rinsed, optionally washed with shampoo, rinsed again and dried or left to dry.

The present invention also relates to a process for lightening keratin fibres, in particular human keratin fibres such as the hair, in which the dye composition according to the invention, free of oxidizing agent, and an oxidizing composition are sequentially or simultaneously applied for a time that is sufficient to obtain the desired lightening, after which the resulting fibres are rinsed, optionally washed with shampoo, rinsed again and dried or left to dry.

The invention also relates to a multi-compartment device or kit using the said dye composition according to the invention.

Moreover, a subject of the invention is colourless or weakly coloured compounds of leuco type, which are the reduced form of the direct dyes of azomethine type according to the invention of formula (II) below, organic or mineral acid salts thereof, tautomeric forms, optical isomers or geometrical isomers thereof, and solvates thereof:

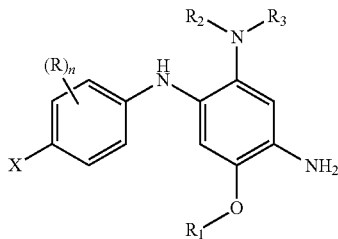

(II)

in which formula (II) n, R, $R_1$, $R_2$, $R_3$, X, $R_4$ and $R_5$ have the same meanings as those indicated in formula (I).

A subject of the invention is also the use of these compounds of leuco type as precursors of the direct dyes of azomethine type of formula (I).

Furthermore, a subject of the invention is the use of these compounds of leuco type for dyeing keratin fibres, such as human keratin fibres, especially the hair, in the presence of an oxidizing agent.

Finally, the invention relates to a multi-compartment device or kit using a dye composition comprising one or more compounds of leuco type of formula (II).

The direct dyes of azomethine type of formula (I) according to the invention can give colorations that are very resistant to the various attacking factors to which keratin fibres may be subjected, such as inclement weather, light, washing and perspiration.

Furthermore, the direct dyes according to the invention can satisfactorily dye keratin fibres, especially producing powerful, chromatic and sparingly selective colorations.

The direct dyes according to the invention are also lightfast and can be used in the presence of an oxidizing agent, which facilitates their use in lightening direct dyeing compositions based on oxidizing agents.

In other words, the direct dyes according to the present invention lead to fast colorations that are compatible with dye compositions intended for lightening keratin fibres.

Other characteristics, aspects, subjects and advantages of the present invention will emerge even more clearly on reading the description and the example that follows.

Direct Dyes of Azomethine Type

The direct dyes according to the invention comprise in their structure two aromatic rings and an azomethine bond.

Preferably, in formula (I), direct dyes of azomethine type according to the invention are such that, taken together or separately:

n represents an integer equal to 0, 1 or 2,

R represents:
  a linear or branched $C_1$-$C_4$ alkyl radical, preferably methyl,
  a $C_1$-$C_4$ alkoxy radical, preferably a methoxy radical,
  a halogen atom, preferably chlorine;
  when n is equal to 2, the groups R are identical or different, $R_1$ represents:
  a linear or branched $C_2$-$C_6$ alkyl radical, optionally substituted with one or more hydroxyl radicals, $R_2$ and $R_3$ represent, independently of each other:
  a hydrogen atom,
  a linear or branched $C_1$-$C_4$ alkyl radical, preferably methyl, ethyl or propyl radical, $R_2$ and $R_3$ may form, together with the nitrogen atom to which they are attached, a pyrrolidino, piperidino or morpholino ring, X represents:
  a hydroxyl radical,
  a radical —$NR_4R_5$ in which $R_4$ and $R_5$ represent, independently of each other:
    a hydrogen atom,
    a linear or branched $C_1$-$C_6$ alkyl radical, optionally substituted with one or more hydroxyl radicals.

Preferably, $An^-$ is an anionic counterion chosen from perchlorate, bromide, iodide, chloride and methosulfate ions or a mixture of these ions.

$An^-$ denotes a cosmetically acceptable anion or mixture of anions, for instance halides, such as chloride, methosulfates, nitrates; alkylsulfonates: $Alk-S(O)_2O^-$ such as methanesulfonate or mesylate, and ethanesulfonate; arylsulfonates: $Ar—S(O)_2O^-$ such as benzenesulfonate and toluenesulfonate or tosylate; citrate; succinate; tartrate; lactate; alkyl sulfates: $Alk-O—S(O)_2O^-$ such as methylsulfate; arylsulfates such as benzenesulfate and toluenesulfate; phosphate; acetate; triflate; and borates such as tetrafluoroborate.

Preferably, $An^-$ is an anionic counterion chosen from bromide, chloride, and methylsulfate and toluenesulfonate ions or a mixture of these ions.

Preferably, n represents an integer equal to 0, 1 or 2, and more preferentially n is equal to 0 or 2.

Preferably, R represents a halogen atom, in particular chlorine, or a linear $C_1$-$C_4$ alkyl radical, in particular a methyl radical.

Preferably, $R_1$ represents a linear or branched $C_2$-$C_6$ alkyl radical, in particular a methyl, ethyl or butyl radical or a linear $C_1$-$C_4$ alkyl radical substituted with a hydroxyl radical, in particular a 2-hydroxyethyl radical.

Preferably, $R_1$ is chosen from a methyl radical; a butyl radical and a 2-hydroxyethyl radical.

Preferably, $R_2$ represents a hydrogen atom or a linear $C_1$-$C_4$ alkyl radical, preferably a butyl, methyl or ethyl radical.

More preferentially, $R_2$ represents a hydrogen atom or a methyl radical.

Even more preferentially, $R_2$ represents a hydrogen atom.

Preferably, $R_3$ represents a hydrogen atom or a linear $C_1$-$C_4$ alkyl radical, preferably a butyl, methyl or ethyl radical.

More preferentially, $R_3$ represents a hydrogen atom or a methyl radical.

Even more preferentially, $R_3$ represents a hydrogen atom.

According to one embodiment, $R_3$ and $R_4$ represent a hydrogen atom.

Preferably, X represents a hydroxyl radical or a radical —$NR_4R_5$ in which $R_4$ and $R_5$ represent, independently of each other, a hydrogen atom or a linear or branched $C_1$-$C_6$ alkyl radical, optionally substituted with one or more hydroxyl radicals.

Preferentially, X represents a hydroxyl radical or a radical —$NR_4R_5$ in which $R_4$ and $R_5$ represent, independently of each other, a linear or branched $C_1$-$C_4$ alkyl radical, optionally substituted with one or more hydroxyl radicals.

Even more preferentially, X represents a radical —$NR_4R_5$ in which $R_4$ and $R_5$ represent, independently of each other, a linear or branched $C_1$-$C_4$ alkyl radical, optionally substituted with one or more hydroxyl radicals.

Preferably, $R_4$ and $R_5$ represent, independently of each other, a hydrogen atom or a methyl, ethyl, isopropyl or 2-hydroxyethyl radical.

According to one embodiment, n represents an integer equal to 0 or 2, $R_1$ is other than a hydrogen atom, $R_2$ represents a hydrogen atom and $R_3$ represents a hydrogen atom.

According to one particular embodiment, n represents an integer equal to 0, $R_1$ is other than a hydrogen atom, $R_2$ represents a hydrogen atom, $R_3$ represents a hydrogen atom and X represents a radical —$NR_4R_5$ in which $R_4$ and $R_5$ represent, independently of each other, a linear or branched $C_2$-$C_3$ alkyl radical, optionally substituted with one or more hydroxyl radicals.

According to another particular embodiment, n represents an integer equal to 2, $R_1$ is other than a hydrogen atom, $R_2$ represents a hydrogen atom, $R_3$ represents a hydrogen atom and X represents a hydroxyl radical.

Preferably, the direct dyes of azomethine type of formula (I) according to the invention are chosen from the following compounds and the geometrical or optical isomer forms thereof, the tautomers thereof, the organic or mineral acid salts thereof or the solvates thereof such as hydrates:

Compound 1

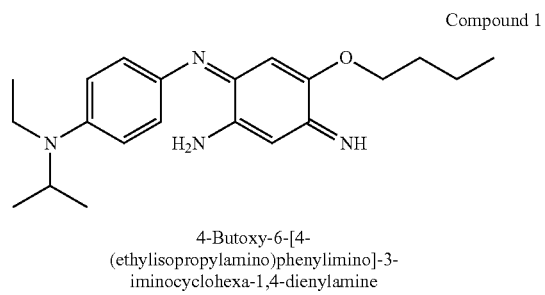

4-Butoxy-6-[4-(ethylisopropylamino)phenylimino]-3-iminocyclohexa-1,4-dienylamine Compound 2

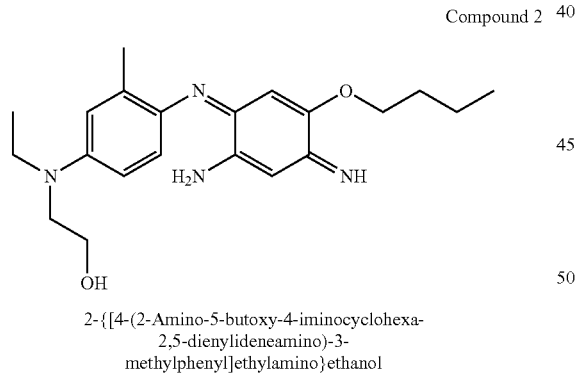

2-{[4-(2-Amino-5-butoxy-4-iminocyclohexa-2,5-dienylideneamino)-3-methylphenyl]ethylamino}ethanol Compound 3

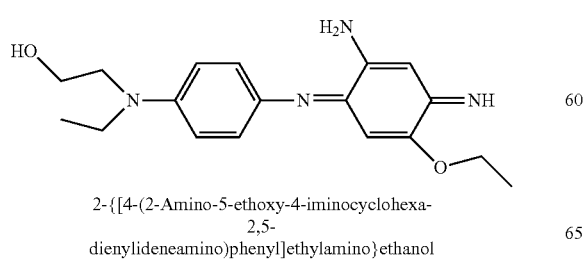

2-{[4-(2-Amino-5-ethoxy-4-iminocyclohexa-2,5-dienylideneamino)phenyl]ethylamino}ethanol Compound 4

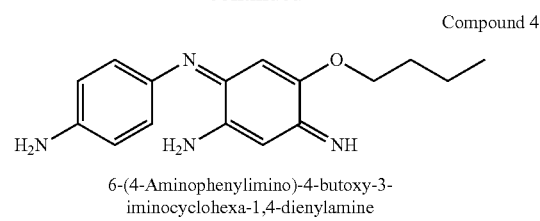

6-(4-Aminophenylimino)-4-butoxy-3-iminocyclohexa-1,4-dienylamine

Compound 5

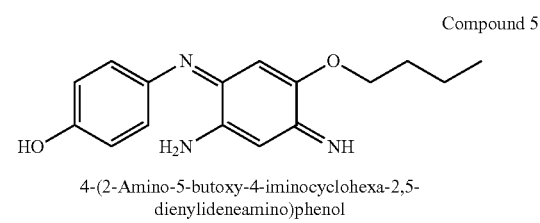

4-(2-Amino-5-butoxy-4-iminocyclohexa-2,5-dienylideneamino)phenol

Compound 6

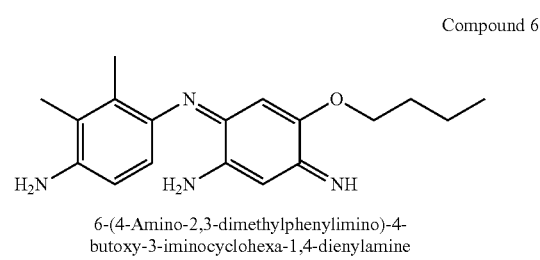

6-(4-Amino-2,3-dimethylphenylimino)-4-butoxy-3-iminocyclohexa-1,4-dienylamine

Compound 7

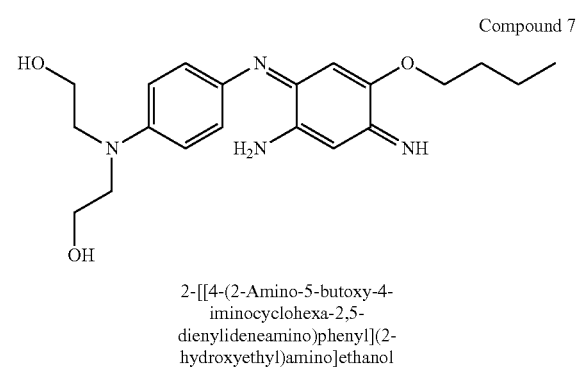

2-[[4-(2-Amino-5-butoxy-4-iminocyclohexa-2,5-dienylideneamino)phenyl](2-hydroxyethyl)amino]ethanol Compound 8

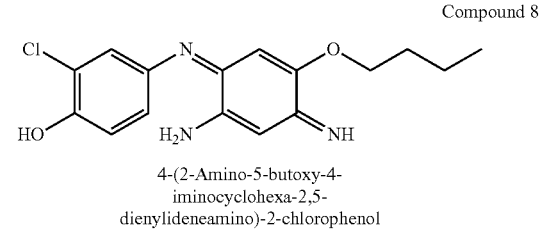

4-(2-Amino-5-butoxy-4-iminocyclohexa-2,5-dienylideneamino)-2-chlorophenol

Compound 9

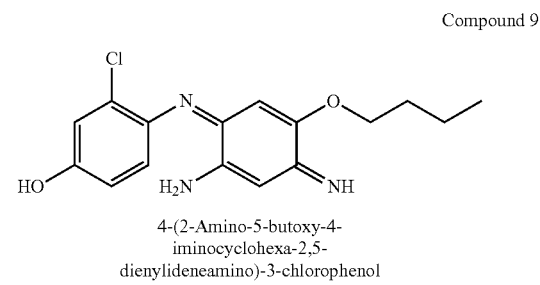

4-(2-Amino-5-butoxy-4-iminocyclohexa-2,5-dienylideneamino)-3-chlorophenol

-continued

Compound 10

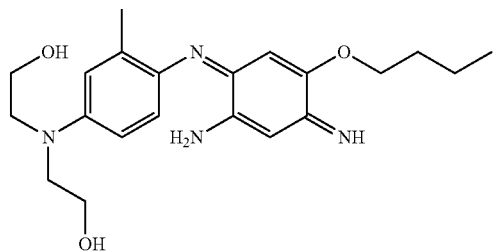

2-[[4-(2-Amino-5-butoxy-4-iminocyclohexa-2,5-dienylideneamino)-3-methylphenyl](2-hydroxyethyl)amino]ethanol Compound 11

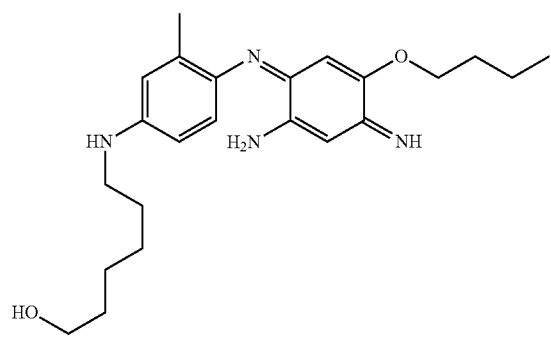

6-[4-(2-Amino-5-butoxy-4-iminocyclohexa-2,5-dienylideneamino)-3-methylphenylamino]hexan-1-ol Compound 12

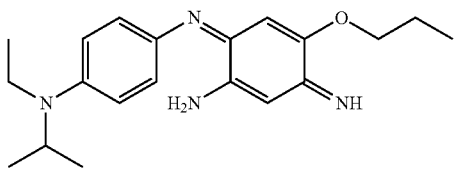

4-propoxy-6-[4-(ethylisipropylamino)phenylimino]-3-iminocyclohexa-1,4-dienylamine Compound 13

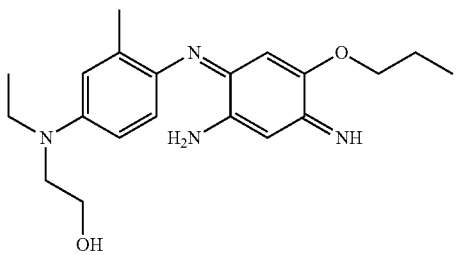

2-{[4-(2-Amino-5-propoxy-4-iminocyclohexa-2,5-dienylideneamino)-3-methylphenyl]ethylamino}ethanol Compound 14

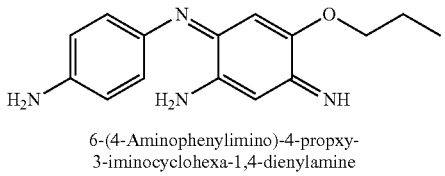

6-(4-Aminophenylimino)-4-propoxy-3-iminocyclohexa-1,4-dienylamine

Compound 15

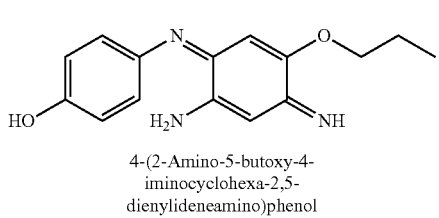

4-(2-Amino-5-butoxy-4-iminocyclohexa-2,5-dienylideneamino)phenol

Compound 16

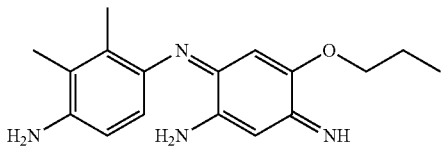

6-(2-Amino-2,3-dimethylphenylimino)-4-propoxy-3-iminocyclohexa-1,4-dienylamine

Compound 17

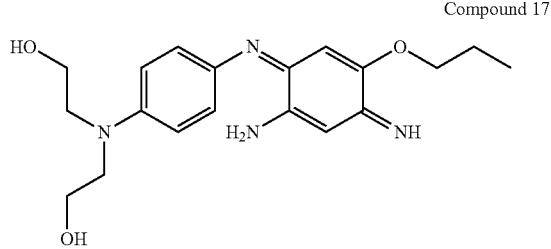

2-[[4-(2-Amino-5-propoxy-4-iminocyclohexa-2,5-dienylideneamino)phenyl](2-hydroxyethyl)amino]ethanol Compound 18

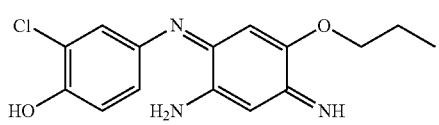

4-(2-Amino-5-propoxy-4-iminocyclohexa-2,5-dienylideneamino)-2-chlorophenol

Compound 19

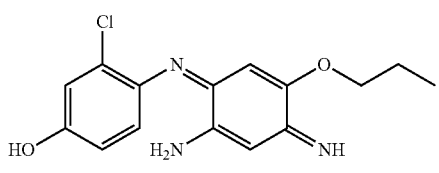

4-(2-Amino-5-propoxy-4-iminocyclohexa-2,5-dienylideneamino)-3-chlorophenol

Compound 20

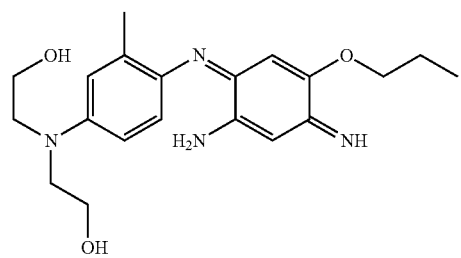

2-[[4-(2-Amino-5-propoxy-4-iminocyclohexa-2,5-dienylideneamino)-3-methylphenyl](2-hydroxyethyl)amino]ethanol Compound 21

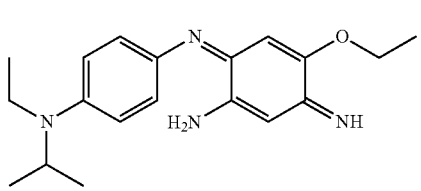

4-ethoxy-6-[4-(ethylisopropylamino)phenylimino]-3-iminocyclohexa-1,4-dienylamine Compound 22

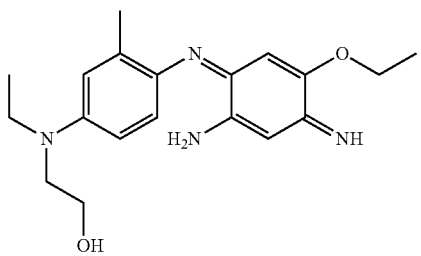

2-{[4-(2-Amino-5-ethoxy-4-iminocyclohexa-2,5-dienylideneamino)-3-methylphenyl]ethylamino}ethanol Compound 23

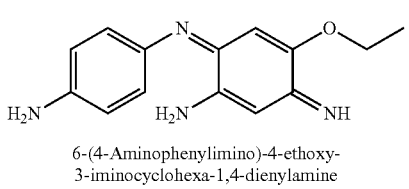

6-(4-Aminophenylimino)-4-ethoxy-3-iminocyclohexa-1,4-dienylamine

Compound 24

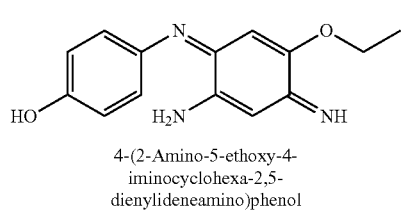

4-(2-Amino-5-ethoxy-4-iminocyclohexa-2,5-dienylideneamino)phenol

Compound 25

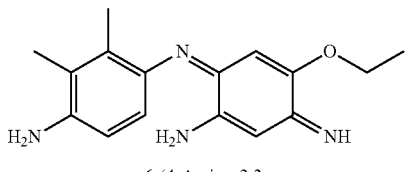

6-(4-Amino-2,3-dimethylphenylimino)-4-ethoxy-3-iminocyclohexa-1,4-dienylamine

Compound 26

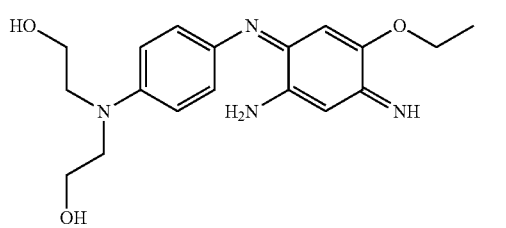

2-[[4-(2-Amino-5-ethoxy-4-iminocyclohexa-2,5-dienylideneamino)phenyl](2-hydroxyethyl)amino]ethanol Compound 27

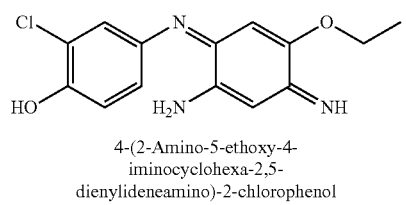

4-(2-Amino-5-ethoxy-4-iminocyclohexa-2,5-dienylideneamino)-2-chlorophenol

Compound 28

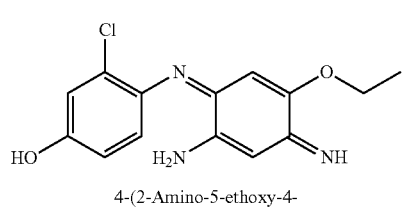

4-(2-Amino-5-ethoxy-4-iminocyclohexa-2,5-dienylideneamino)-3-chlorophenol

Compound 29

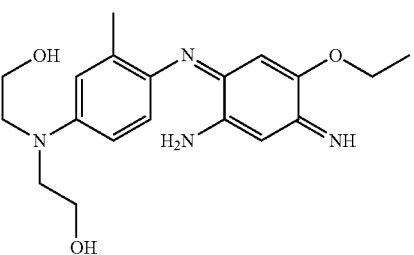
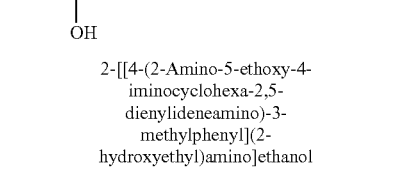

2-[[4-(2-Amino-5-ethoxy-4-iminocyclohexa-2,5-dienylideneamino)-3-methylphenyl](2-hydroxyethyl)amino]ethanol -continued Compound 30

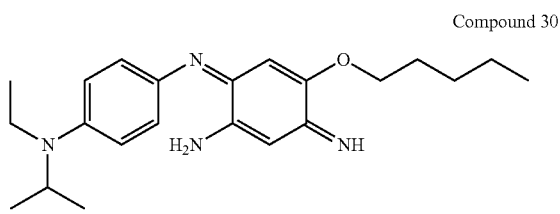

4-pentyloxy-6-[4-
(ethylisopropylamino)phenylimino]-
3-iminocyclohexa-1,4-dienylamine Compound 31

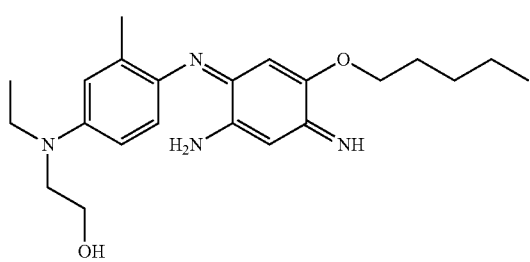

2-{[4-(2-Amino-5-pentyloxy-4-
iminocyclohexa-2,5-
dienylideneamino)-3-
methylphenyl]ethylamino}ethanol Compound 32

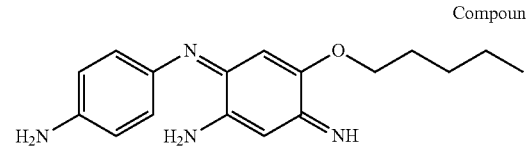

6-(4-Aminophenylimino)-4-
pentyloxy-3-iminocyclohexa-1,4-
dienylamine

Compound 33

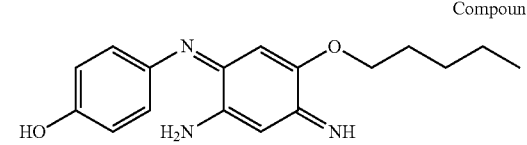

4-(2-Amino-5-pentyloxy-4-
iminocyclohexa-2,5-
dienylideneamino)phenol

Compound 34

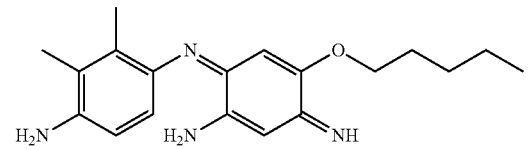

6-(4-Amino-2,3-
dimethylphenylimino)-4-pentyloxy-3-
iminocyclohexa-1,4-dienylamine Compound 35

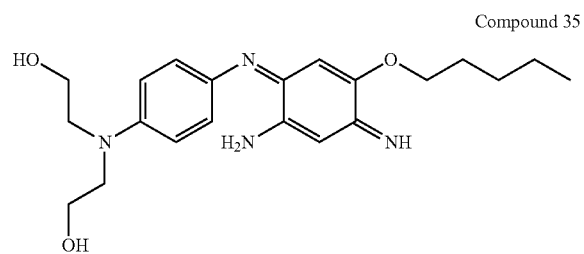

2-[[4-(2-Amino-5-pentyloxy-4-
iminocyclohexa-2,5-
dienylideneamino)phenyl(2-
hydroxyethyl)amino]ethanol Compound 36

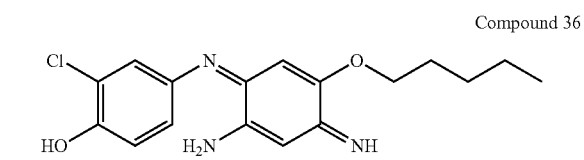

4-(2-Amino-5-pentyloxy-4-
iminocyclohexa-2,5-
dienylideneamino)-2-chlorophenol

Compound 37

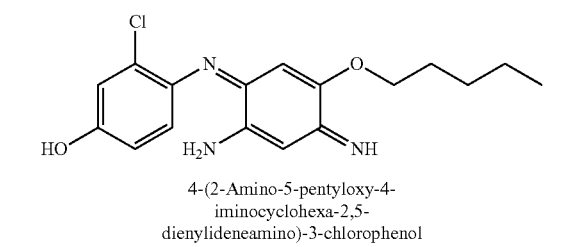

4-(2-Amino-5-pentyloxy-4-
iminocyclohexa-2,5-
dienylideneamino)-3-chlorophenol

Compound 38

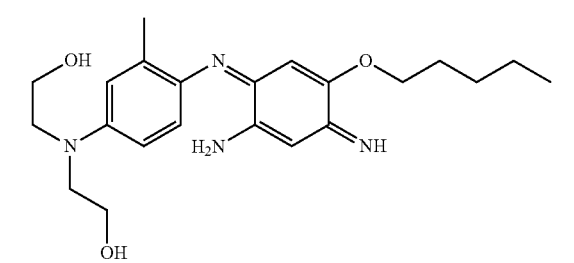

2-[[4-(2-Amino-5-pentyloxy-4-
iminocyclohexa-2,5-
dienylideneamino)-3-
methylphenyl](2-
hydroxyethyl)amino]ethanol Compound 39

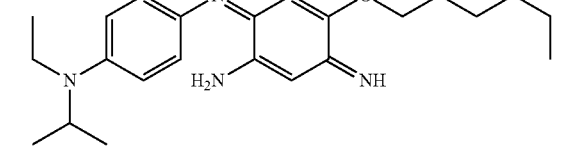

4-hexyloxy-6-[4-
(ethylisopropylamino)phenylimino]-3-
iminocyclohexa-1,4-dienylamine -continued Compound 40

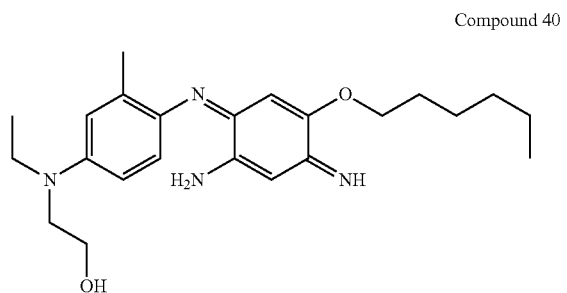

2-{[4-(2-Amino-5-hexyloxy-4-iminocyclohexa-2,5-dienylideneamino)-3-methylphenyl]ethylamino}ethanol Compound 41

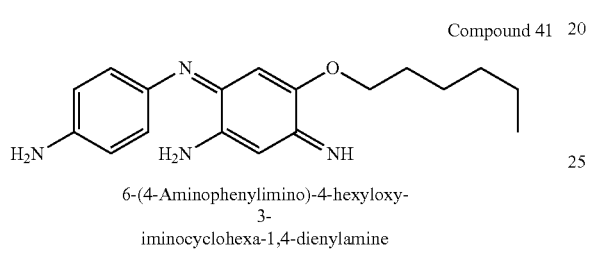

6-(4-Aminophenylimino)-4-hexyloxy-3-iminocyclohexa-1,4-dienylamine

Compound 42

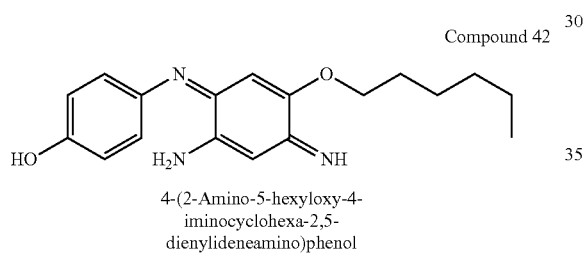

4-(2-Amino-5-hexyloxy-4-iminocyclohexa-2,5-dienylideneamino)phenol

Compound 43

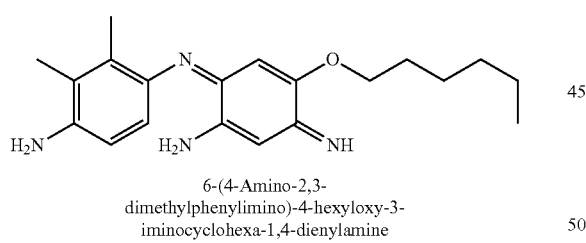

6-(4-Amino-2,3-dimethylphenylimino)-4-hexyloxy-3-iminocyclohexa-1,4-dienylamine

Compound 44

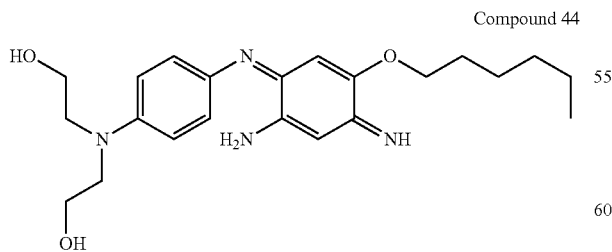

2-[[4-(2-Amino-5-hexyloxy-4-iminocyclohexa-2,5-dienylideneamino)phenyl(2-hydroxyethyl)amino]ethanol Compound 45

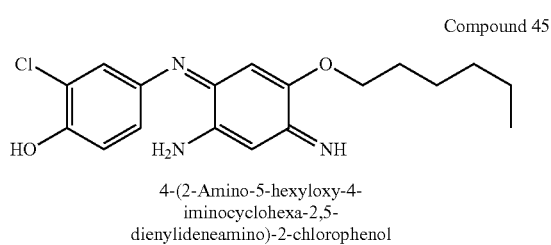

4-(2-Amino-5-hexyloxy-4-iminocyclohexa-2,5-dienylideneamino)-2-chlorophenol

Compound 46

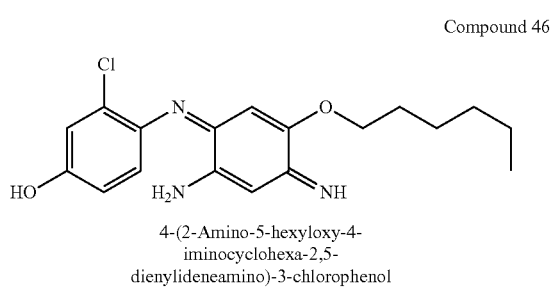

4-(2-Amino-5-hexyloxy-4-iminocyclohexa-2,5-dienylideneamino)-3-chlorophenol

Compound 47

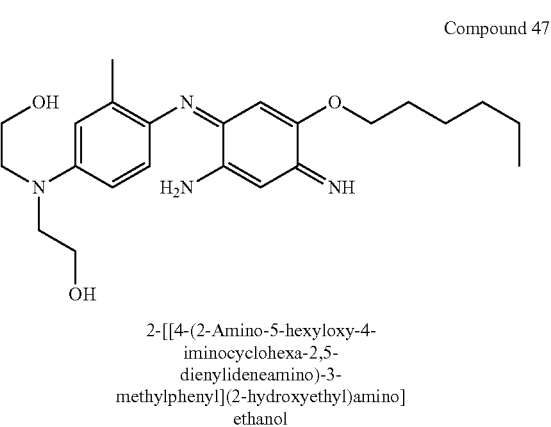

2-[[4-(2-Amino-5-hexyloxy-4-iminocyclohexa-2,5-dienylideneamino)-3-methylphenyl](2-hydroxyethyl)amino]ethanol Compound 48

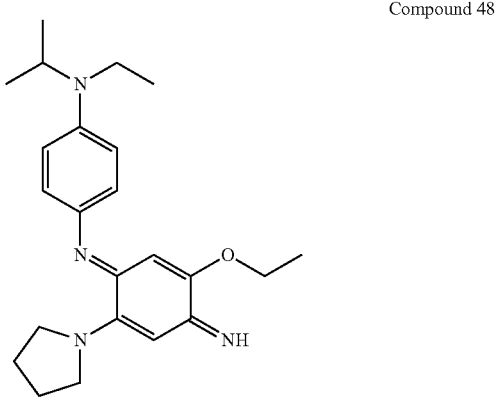

N-(5-Ethoxy-4-imino-2-pyrrolidin-1-ylcyclohexa-2,5-dienylidene)-N'-ethyl-N'-isopropylbenzene-1,4-diamine Compound 49

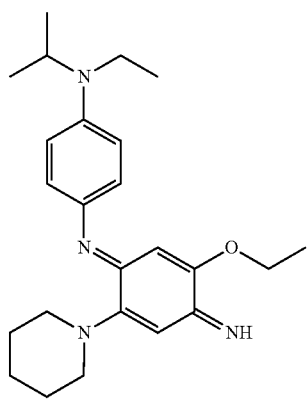

N-(5-Ethoxy-4-imino-2-piperidin-1-ylcyclohexa-2,5-dienylidene)-N'-ethyl-N'-isopropylbenzene-1,4-diamine Compound 50

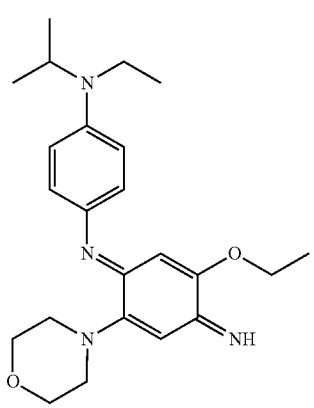

N-(5-Ethoxy-4-imino-2-morpholin-4-ylcyclohexa-2,5-dienylidene)-N'-ethyl-N'-isopropylbenzene-1,4-diamine Compound 51

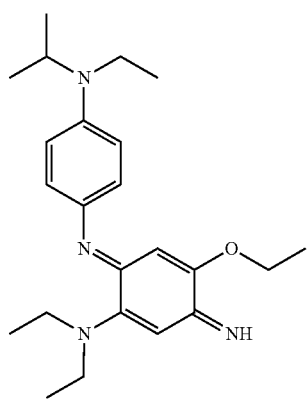

N-(2-Diethylamino-5-ethoxy-4-iminocyclohexa-2,5-dienylidene)-N'-ethyl-N'-isopropylbenzene-1,4-diamine Compound 52

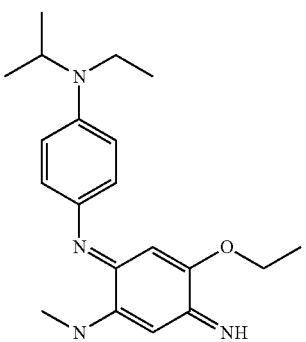

N-(2-methylamino-5-ethoxy-4-iminocyclohexa-2,5-dienylidene)-N'-ethyl-N'-isopropylbenzene-1,4-diamine Compound 53

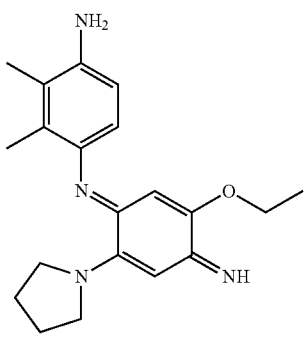

N-(5-Ethoxy-4-imino-2-pyrrolidin-1-ylcyclohexa-2,5-dienylidene)-2,3-dimethylbenzene-1,4-diamine Compound 54

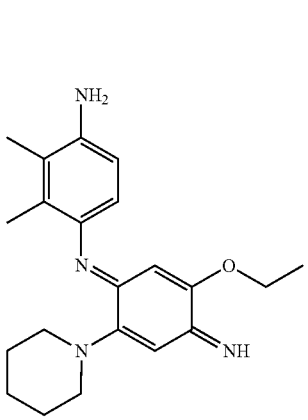

N-(5-Ethoxy-4-imino-2-piperidin-1-ylcyclohexa-2,5-dienylidene)-2,3-dimethylbenzene-1,4-diamine Compound 55

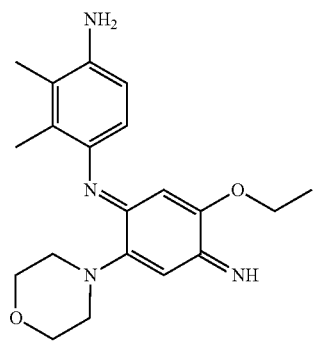

N-(5-Ethoxy-4-imino-2-
morpholin-4-ylcyclohexa-2,5-
dienylidene)-2,3-
dimethylbenzene-1,4-
diamine Compound 56

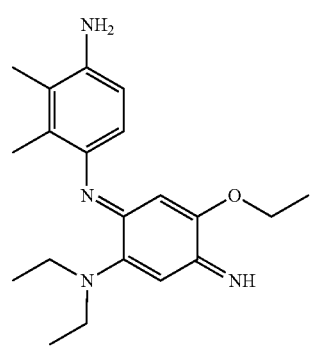

N-(2-Diethylamino-5-ethoxy-4-
iminocyclohexa-2,5-dienylidene)-
2,3-dimethylbenzene-1,4-
diamine Compound 57

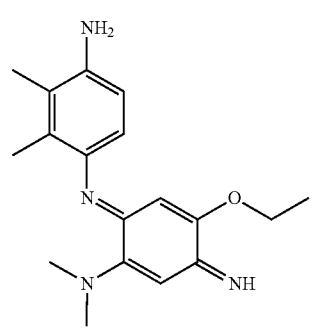

N-(2-Dimethylamino-5-ethoxy-4-imino
cyclohexa-2,5-dienylidene)-
2,3-dimethylbenzene-1,4-
diamine Compound 58

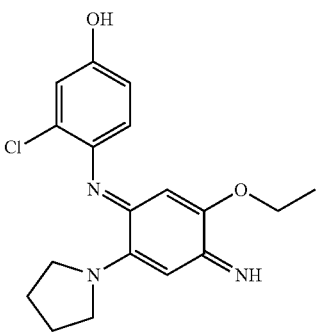

3-Chloro-4-(5-ethoxy-4-imino-2-
pyrrolidin-1-ylcyclohexa-2,5-
dienylideneamino)phenol Compound 59

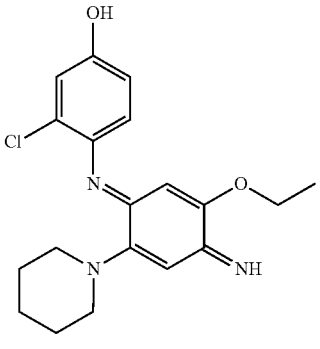

3-Chloro-4-(5-ethoxy-4-imino-2-
piperidin-1-ylcyclohexa-2,5-
dienylideneamino)phenol Compound 60

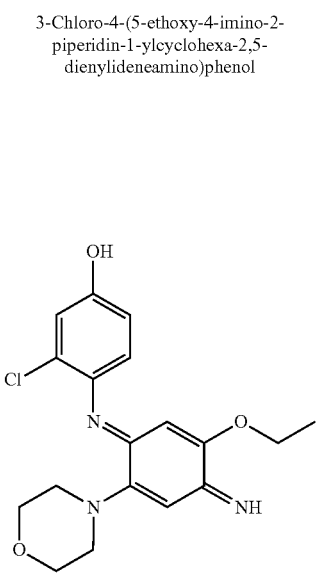

3-Chloro-4-(5-ethoxy-4-imino-2-
morpholin-4-ylcyclohexa-2,5-
dienylideneamino)phenol -continued Compound 61

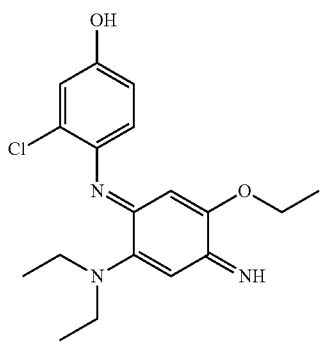

3-Chloro-4-(2-diethylamino-5-
ethoxy-4-iminocyclohexa-2,5-
dienylideneamino)phenol Compound 62

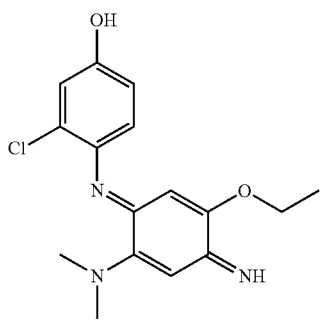

3-Chloro-4-(2-diethylamino-5-
ethoxy-4-iminocyclohexa-2,5-
dienylideneamino)phenol Compound 63

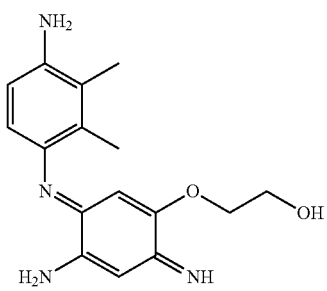

2-{4-Amino-3-[4-amino-2,3-
dimethylphenylimino]-6-iminocyclohexa-1,4-
dienyloxy}ethanol Compound 64

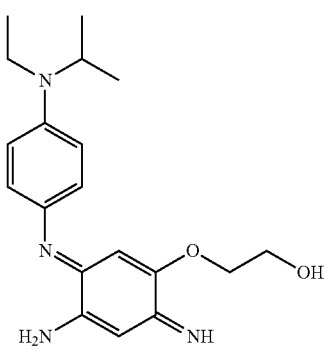

2-{4-Amino-3-[4-
(ethylisopropylamino)phenylimino]-6-
iminocyclohexa-1,4-dienyloxy}ethanol -continued Compound 65

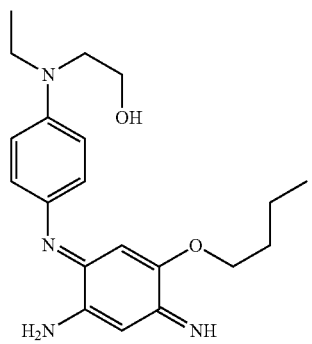

2-({4-[2-Amino-5-butoxy-4-
iminocyclohexa-2,5-
dienylideneamino]phenyl}ethylamino)ethanol Compound 66

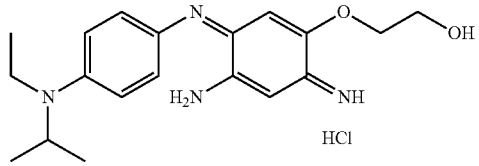

2-{4-amino-3-[4-
(ethylisopropylamino)phenylimino]-6-
iminocyclohexa-1,4-dienyloxy}ethanol Compound 67

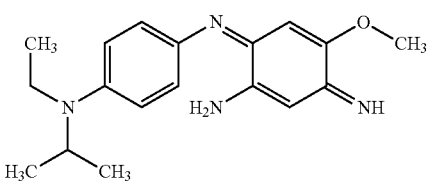

4-methoxy-6-[4-(N-ethyl-N-
isopropylamino)phenylimino]-3-
iminocyclohexa-1,4-dienyl-1-amine Preferably, the direct dyes of formula (I) according to the present invention are chosen from the direct dyes 1, 2, 3, 4, 5, 6, 7, 8, 9, 10, 11, 65 and 66, and more preferentially 1, 2, 3, 8, 10, 65 and 66.

The direct dyes of formula (I) may be obtained according to the procedure below:

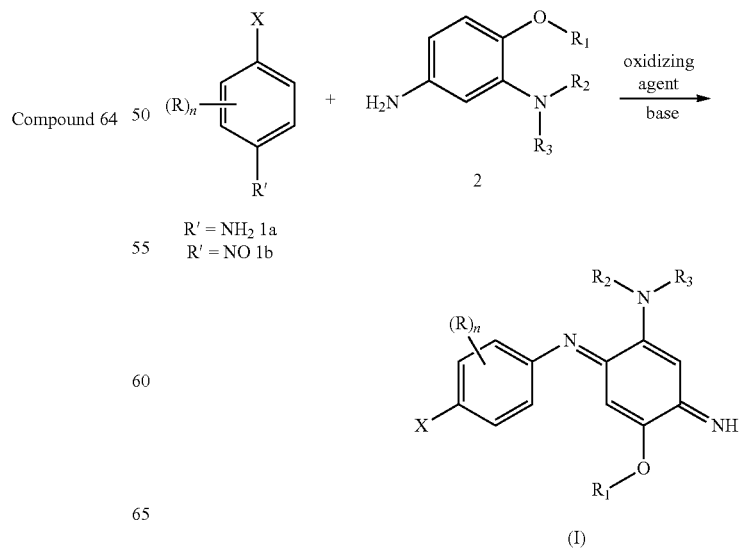

The compounds of formula (I) are generally obtained by reacting the derivatives 1a or 1b with the meta-phenylenediamines 2 in basic medium in the presence of an oxidizing agent. The base used is preferentially an aqueous solution of ammonia or of sodium hydroxide and the oxidizing agent is preferentially chosen from aqueous hydrogen peroxide solution, potassium ferricyanide, air, ammonium persulfate and manganese oxide.

Synthetic approaches similar to this reaction scheme are described in patents FR 2 234 277, FR 2 047 932, FR 2 106 661 and FR 2 121 101.

Use of the Direct Dye

The present invention also relates to the use of one or more compounds of azomethine type of formula (I) as defined previously for dyeing keratin fibres, in particular human keratin fibres such as the hair.

Composition

A subject of the invention is also the composition in particular for dyeing keratin fibres, in particular human keratin fibres such as the hair, comprising one or more azomethine compounds of formula (I) as defined previously.

The direct dye(s) as defined previously may be present in the dye composition in a content ranging from 0.001% to 10% by weight and preferably in a content ranging from 0.005% to 6% by weight, relative to the total weight of the dye composition.

The dye composition according to the invention may also comprise one or more oxidation dyes.

The oxidation dyes are generally chosen from oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and addition salts thereof with an acid.

Preference is particularly given, among the abovementioned para-phenylenediamines, to para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and their addition salts with an acid.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Mention may be made, among para-aminophenols, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and their addition salts with an acid.

Mention may be made, among ortho-aminophenols, by way of example, of 2-aminophenol, 2-amino-5-methylphenol, 2-amino-6-methylphenol, 5-acetamido-2-aminophenol and their addition salts.

Mention may be made, among heterocyclic bases, by way of example, of pyridine derivatives, pyrimidine derivatives and pyrazole derivatives.

Mention may be made, among pyridine derivatives, of the compounds described, for example, in patents GB 1 026 978 and GB 1 153 196, such as 2,5-diaminopyridine, 2-(4-methoxyphenyl)amino-3-aminopyridine, 3,4-diaminopyridine and their addition salts.

Other pyridine oxidation bases of use in the present invention are the 3-aminopyrazolo[1,5-a]pyridine oxidation bases or their addition salts described, for example, in Patent Application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(β-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and their addition salts.

Mention may be made, among pyrimidine derivatives, of the compounds described, for example, in patents DE 2359399, JP 63-169571, JP 05-163124, and EP 0 770 375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

4,5-Diamino-1-(β-methoxyethyl)pyrazole may also be used.

Use will preferably be made of a 4,5-diaminopyrazole and even more preferentially of 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or one of their salts.

The dye composition may optionally comprise one or more couplers advantageously chosen from those conventionally used for the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that can be used within the context of the invention are especially chosen from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight and preferably from 0.005% to 6% by weight relative to the total weight of the composition.

The content of coupler(s), if they are present, each advantageously represent from 0.001% to 10% by weight relative to the total weight of the composition, and preferably from 0.005% to 6% by weight relative to the total weight of the dye composition.

The dye composition may also comprise one or more additional direct dyes other than the direct dyes of azomethine type defined previously.

The additional direct dye(s) according to the invention are chosen from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, azomethine direct dyes and natural direct dyes.

Among the benzenic direct dyes that may be used according to the invention, mention may be made in a non-limiting manner of the following compounds:
1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;

1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene; and
1-hydroxy-4-β-hydroxyethylamino-3-nitrobenzene.

Among the azo direct dyes that may be used according to the invention, mention may be made of the cationic azo dyes described in patent applications WO 95/15144, WO-95/01772 and EP-714954, the content of which forms an integral part of the invention.

Among these compounds, the ones that may be mentioned most particularly are the following dyes:
1,3-dimethyl-2-[[4-(dimethylamino)-phenyl]-azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes, described in the Colour Index International, 3rd edition: Disperse Red 17, Acid Yellow 9, Acid Black 1, Basic Red 22, Basic Red 76, Basic Red 51, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
1-N-methylmorpholiniumpropylamino-4-hydroxyanthraquinone
1-aminopropylamino-4-methylamino anthraquinone
1-aminopropylaminoanthraquinone
5-β-hydroxyethyl-1,4-diamino anthraquinone
2-amino ethylamino anthraquinone
1,4-bis(β,γ-dihydroxypropylamino)anthraquinone.

Among the azine dyes, mention may be made of the following compounds: Basic Blue 17, Basic Red 2.

Among the triarylmethane dyes that may be used according to the invention, mention may be made of the following compounds: Basic Green 1, Acid Blue 9, Basic Violet 3, Basic Violet 14, Basic Blue 7, Acid Violet 49, Basic Blue 26, Acid Blue 7.

Among the azomethine dyes that may be used according to the invention, mention may be made of the following compounds:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinoneimine;
3-N-(3'-chloro-4'-methylamino)phenylureido-6-methyl-1,4-benzoquinoneimine; and
3-[4'-N-(ethyl,carbamylmethyl)amino]phenylureido-6-methyl-1,4-benzoquinoneimine.

Preferably, the composition according to the invention comprises at least one azomethine compound of formula (I) and at least one azomethine dye other than those of formula (I).

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular poultices or henna-based extracts may also be used.

The additional direct dye(s) may be present in the dye composition in a content ranging from 0.001% to 10% by weight and preferably in a content ranging from 0.005% to 6% by weight, relative to the total weight of the composition.

The medium that is suitable for dyeing, also known as the dye support, is a cosmetic medium generally formed from water or a mixture of water and of at least one organic solvent. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

When they are present, the solvents are present in proportions preferably of between 1% and 99% by weight approximately and even more preferentially between 5% and 95% by weight approximately relative to the total weight of the dye composition.

The dye composition may also contain various adjuvants conventionally used in hair dye compositions, such as anionic, cationic, nonionic or amphoteric surfactants or mixtures thereof, anionic, cationic, nonionic or amphoteric polymers or mixtures thereof, mineral or organic thickeners, and in particular anionic, cationic, nonionic and amphoteric polymeric associative thickeners, antioxidants, penetrants, solubilizers, sequestrants, fragrances, buffers, dispersants, conditioning agents, for instance volatile or nonvolatile, modified or unmodified silicones such as amino silicones, film-forming agents, ceramides, preserving agents, opacifiers and conductive polymers.

The above adjuvants are generally present in an amount for each of them of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents commonly used in the dyeing of keratin fibres, or alternatively using standard buffer systems.

Among the acidifying agents, mention may be made, by way of example, of mineral or organic acids other than dicarboxylic acids, such as hydrochloric acid, ortho-phosphoric acid, sulfuric acid, carboxylic acids such as acetic acid, tartaric acid, citric acid or lactic acid, and sulfonic acids.

Among the basifying agents, mention may be made, by way of example, of aqueous ammonia, alkali metal carbonates, alkanolamines such as mono-, di- and triethanolamines and their derivatives, sodium hydroxide or potassium hydroxide, and the compounds of formula:

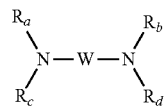

in which W is a propylene residue optionally substituted with a hydroxyl group or a $C_1$-$C_4$ alkyl radical; and $R_a$, $R_b$, $R_c$ and $R_d$, which may be identical or different, represent a hydrogen atom or a $C_1$-$C_4$ alkyl or $C_1$-$C_4$ hydroxyalkyl radical.

The cosmetic composition according to the invention may be present in a variety of forms, such as in the form of liquids, creams, gels, or any other form which is appropriate for carrying out dyeing of keratin fibres, and in particular of human hair.

As indicated previously, the invention also relates to the use of the dye composition as defined previously for dyeing keratin fibres, in particular human keratin fibres such as the hair.

Process

The dyeing process according to the present invention consists in applying to wet or dry keratin fibres a dye composition as defined previously for a time that is sufficient to obtain the desired coloration, and the fibres are then rinsed, optionally washed with shampoo and rinsed again, and the resulting fibres are dried or left to dry.

Preferably, the leave-on time for the dye composition is between 1 and 60 minutes, preferably between 5 and 40 minutes and even more preferably between 10 and 30 minutes.

The dye composition is generally applied to the keratin fibres at room temperature, preferably between 25 and 55° C.

According to one embodiment, the dye composition according to the invention is applied to the keratin fibres in the presence of one or more oxidizing agents for a time that is sufficient to obtain the desired lightening.

The oxidizing agent may be present in the dye composition or may be used separately in a cosmetic composition.

Preferably, the oxidizing agent is used separately in a cosmetic composition.

Thus, the present invention also relates to a process for lightening keratin fibres, in particular human keratin fibres such as the hair, in which (i) the dye composition as defined previously, free of oxidizing agent, and (ii) a cosmetic composition comprising one or more oxidizing agents are applied to the said fibres; compositions (i) and (ii) being applied to the said keratin fibres sequentially or simultaneously for a time that is sufficient to obtain the desired lightening, and the fibres are then rinsed, optionally washed with shampoo and rinsed again, and the resulting fibres are dried or left to dry.

For the purposes of the present invention, the term "sequentially" means that the oxidizing composition is applied before or after the dye composition, i.e. as a pretreatment or a post-treatment.

The oxidizing agents used are chosen from hydrogen peroxide, urea peroxide, alkali metal bromates, persalts such as perborates and persulfates, peracids, and oxidase enzymes (with the possible cofactors thereof), among which mention may be made of peroxidases, 2-electron oxidoreductases such as uricases, and 4-electron oxygenases, for instance laccases.

The oxidizing agent is preferably hydrogen peroxide.

The oxidizing composition may also contain various adjuvants conventionally used in compositions for dyeing the hair and as defined previously.

The pH of the oxidizing composition containing the oxidizing agent is such that, after mixing with the dye composition, the pH of the resulting composition applied to the keratin fibres preferably ranges between 3 and 12 approximately, even more preferentially between 5 and 11 and even more particularly between 6 and 8.5. It may be adjusted to the desired value by means of acidifying or basifying agents usually used in the dyeing of keratin fibres and as defined previously.

Kit

The present invention also relates to a multi-compartment device or "kit" comprising a first compartment containing a cosmetic composition comprising one or more compounds of formula (I) as defined previously, free of oxidizing agent, and a second compartment comprising one or more oxidizing agents.

According to one particular embodiment, the device may comprise at least one compartment comprising a cosmetic composition comprising one or more compounds of the abovementioned formula (I).

Leuco Compounds

Moreover, a subject of the invention is compounds of leuco type, which are the reduced form of the direct dyes of azomethine type according to the invention of formula (II) below, organic or mineral acid salts thereof, tautomeric forms, optical isomers or geometrical isomers thereof, and solvates thereof:

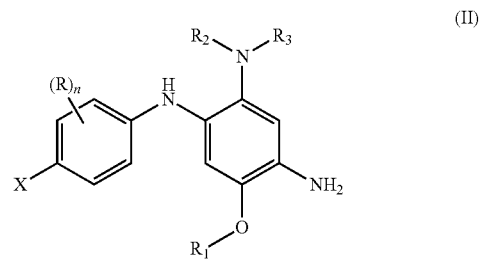

(II)

in which n, R, $R_1$, $R_2$, $R_3$, X, $R_4$ and $R_5$ have the same meanings as those indicated in formula (I).

Preferably, the compounds of formula (II) are chosen from the precursors of compounds 1 to 65 mentioned above.

Even more preferentially, the compounds of leuco type of formula (II) are chosen from precursors of the direct dyes 1, 2, 3, 4, 5, 6, 7, 8, 9, 10, 11 and 65 and more preferentially 1, 2, 3, 8, 10 and 65.

The compounds of formula (II) are generally obtained by reacting the compounds of formula (I) with a reducing agent. This reducing agent may be preferentially chosen from sodium hydrosulfite, zinc powder and ascorbic acid. This reducing agent is preferentially sodium hydrosulfite or zinc.

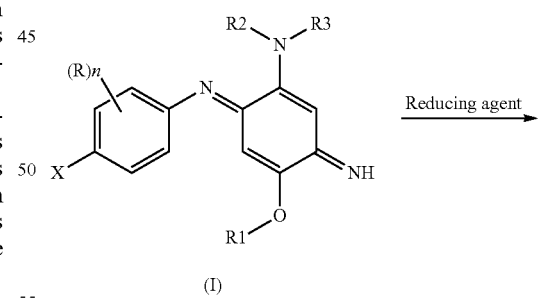

(I)

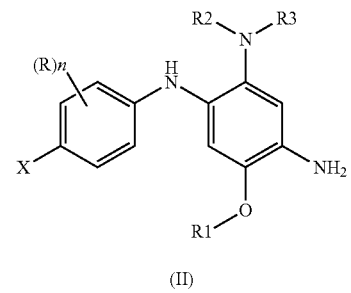

(II)

Synthetic approaches are described in patents FR 2 056 799, FR 2 047 932, FR 2 165 965 and FR 2 262 023.

The invention also relates to the use of one or more compounds of formula (II) as defined above for dyeing keratin fibres, in particular human keratin fibres such as the hair, in the presence of one or more oxidizing agents.

In particular, the invention relates to a cosmetic composition comprising one or more compounds of leuco type of formula (II) as defined previously, and optionally comprising one or more oxidizing agents.

Process

The present invention also relates to a dyeing process in which a cosmetic composition comprising one or more compounds of leuco type of the abovementioned formula (II) is applied to keratin fibres in the presence of one or more oxidizing agents for a time that is sufficient to develop the desired coloration, after which the fibres are rinsed, optionally washed with shampoo and rinsed again, and the resulting fibres are dried or left to dry.

The oxidizing agent may be atmospheric oxygen or may be chosen from the oxidizing agents mentioned previously.

In particular, when the oxidizing agent is atmospheric oxygen, simple exposure to air of the keratin fibres treated with the composition comprising the compound(s) of leuco type makes it possible to generate the colouring species and, consequently, to colour the fibres.

According to one variant, the oxidizing agent(s) may be applied simultaneously or sequentially to the cosmetic composition comprising the compounds of leuco type.

Thus, the cosmetic composition comprising the oxidizing agent(s) may be applied to the keratin fibres before, simultaneously with or after the cosmetic composition comprising the compounds of leuco type of formula (II) according to the invention.

According to another variant, a ready-to-use composition which results from the mixing of a cosmetic composition comprising one or more compounds of leuco type of the abovementioned formula (II) and of a cosmetic composition comprising one or more oxidizing agents is applied to the keratin fibres.

The ready-to-use composition that is thus applied to the keratin fibres may be in various forms, such as in the form of liquids, creams or gels or in any other form that is suitable for dyeing keratin fibres, and especially human hair.

The leave-on time for the composition(s) ranges from 1 to 60 minutes, preferably from 5 to 40 minutes and even more preferentially from 10 to 30 minutes.

The cosmetic composition comprising such compounds of leuco type is generally applied to the keratin fibres at room temperature, preferably between 25 and 55° C.

Kit

The present invention also relates to a multi-compartment device or "kit" comprising a first compartment containing a cosmetic composition comprising one or more compounds of leuco type of formula (II) as defined previously, free of oxidizing agent, and a second compartment comprising one or more oxidizing agents.

According to one particular embodiment, the device may comprise at least one compartment comprising a cosmetic composition comprising one or more compounds of leuco type of the abovementioned formula (II).

In this case, the composition comprising the compound(s) of leuco type as defined above is applied to the keratin fibres, which become coloured due to their exposure to atmospheric oxygen, as oxidizing agent.

The devices mentioned above are suitable for dyeing keratin fibres.

The examples that follow serve to illustrate the invention without, however, being limiting in nature.

EXAMPLES

1/Synthesis Examples

Example 1

Synthesis of 4-butoxy-6-[4-(ethylisopropylamino) phenylimino]-3-iminocyclohexa-1,4-dienylamine hydrochloride 1

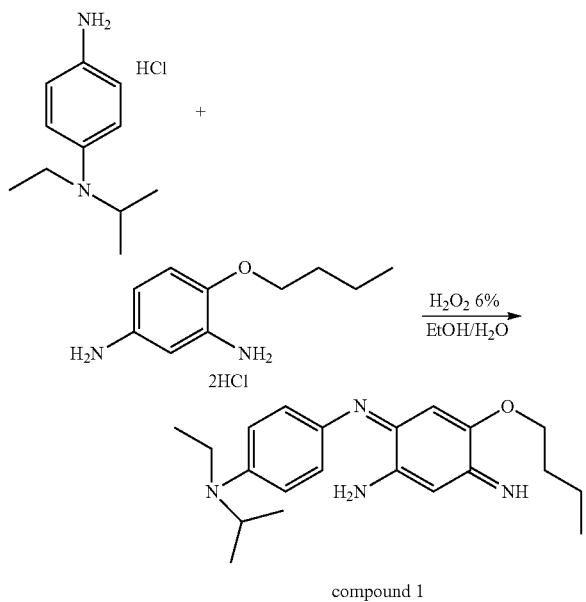

compound 1

To a solution of 0.003 mol of N-methyl-N-isopropyl-4-aminoaniline hydrochloride and 0.003 mol of 4-butoxybenzene-1,3-diamine dihydrochloride in 2 ml of water and 6 ml of ethanol, brought to pH 9.5 with 20% aqueous ammonia solution, are added 10.2 ml of 20-V 6% aqueous hydrogen peroxide solution; after stirring for 24 hours at room temperature, a gum forms. The supernatant is removed and the gum is washed with three times 50 ml of water, 4 ml of ethyl acetate and then with isopropyl ether. After drying, 260 mg of 4-butoxy-6-[4-(ethylisopropylamino)phenylamino]-3-iminocyclohexa-1,4-dienylamine hydrochloride 1 are obtained in the form of a black powder.

The molecular ion 355 (ES+) is detected by mass spectrometry.

Example 2

Synthesis of 2-{[4-(2-amino-5-butoxy-4-iminocyclohexa-2,5-dienylideneamino)-3-methylphenyl] ethylamino}ethanol 2

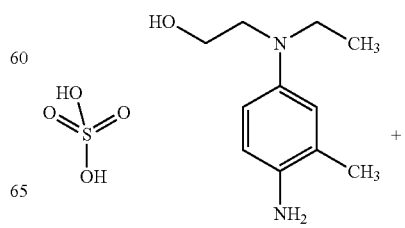

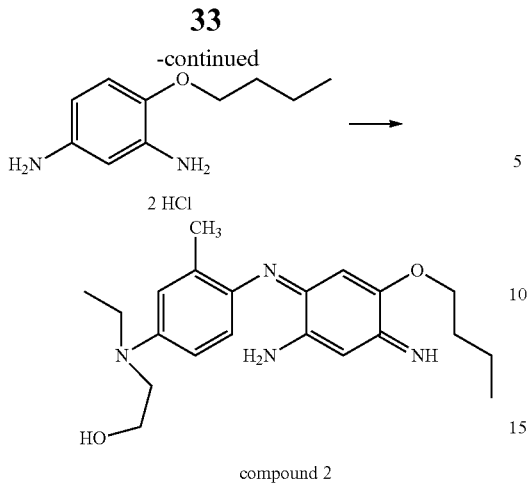

compound 2

To a solution of 4.39 g (0.015 mol) of 2-[(4-amino-3-methylphenyl)(ethyl)amino]ethanol sulfate in 5 ml of water and 10 ml of ethanol is added a solution of 4-butoxybenzene-1,3-diamine dihydrochloride in 5 ml of water and 10 ml of ethanol. The pH is adjusted to 9.5 with 15 ml of 20% aqueous ammonia. 51 ml of 6% aqueous hydrogen peroxide solution are added and the mixture is stirred for 12 hours. The resulting mixture is extracted with butanol. The organic phase is washed with water brought to pH 10.5 with 20% aqueous ammonia. The organic phase is dried with disodium sulfate and filtered, and the butanol is then evaporated off. The product is washed with isopropyl ether and filtered off. 2.81 g of 2-{[4-(2-amino-5-butoxy-4-imino cyclo hexa-2,5-dienylideneamino)-3-methylphenyl]ethylamino}ethanol 2 are obtained in the form of a black product.

The molecular ion 371 (ES+) is detected by mass spectrometry.

Example 3

Synthesis of 2-chloro-4-[(2,4-diamino-5-butoxyphenyl)imino]cyclohexa-2,5-dien-1-one 8

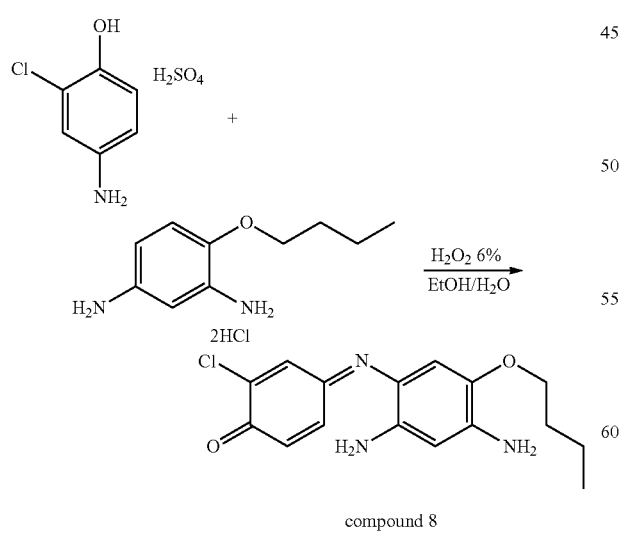

compound 8

26 ml of 6% aqueous hydrogen peroxide solution are added to a solution of 180 mg (0.001 mol) of 4-amino-2-chlorophenol sulfate and 253 mg (0.001 mol) of 4-butoxybenzene-1,3-diamine dihydrochloride in 2 ml of water and 2 ml of ethanol, and the solution is adjusted to pH 9.5 with 20% aqueous ammonia. After stirring for 5 hours at room temperature, the precipitate formed is filtered off, washed with water and dried. A brown powder is obtained.

The molecular ion 320 (ES+) is detected by mass spectrometry.

Example 4

Synthesis of 2-{[4-(2-amino-5-ethoxy-4-iminocyclohexa-2,5-dienylideneamino)phenyl]ethylamino}ethanol 3

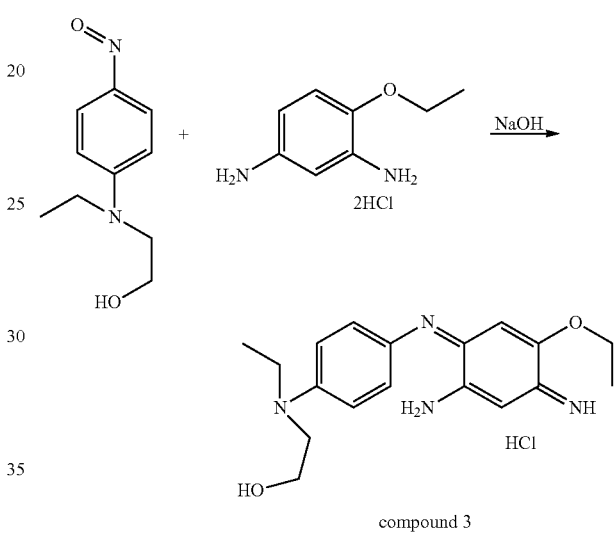

compound 3

A solution of 4-ethoxybenzene-1,3-diamine dihydrochloride in 4 ml of 0.25N sodium hydroxide is added to a solution of 2-[ethyl(4-nitrosophenyl)amino]ethanol in 2 ml of water, and the mixture is heated to 50° C. After concentrating the reaction medium, taking up the residue in isopropyl ether and filtering off and drying the precipitate formed, 360 mg of 2-{[4-(2-amino-5-ethoxy-4-imino cyclohexa-2,5-dienylideneamino)phenyl]ethylamino}ethanol dihydrochloride 3 are obtained as a black powder.

The molecular ion 329 (ES+) is mainly detected.

Example 5

Synthesis of 2-[[4-(2-amino-5-butoxy-4-iminocyclohexa-2,5-dienylideneamino)phenyl](2-hydroxyethyl)amino]ethanol 10

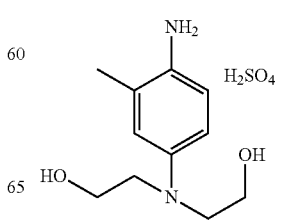

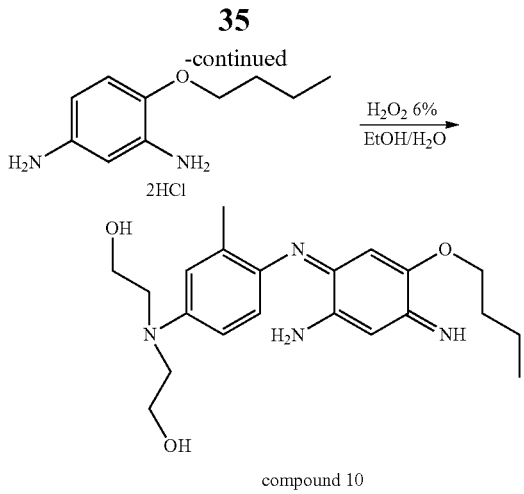

compound 10

To a solution of 0.925 g (0.003 mol) of N-ethyl-N-isopropyl-4-aminoaniline hydrochloride and 0.76 g (0.003 mol) of 4-butoxybenzene-1,3-diamine dihydrochloride in 2 ml of water and 6 ml of ethanol, brought to pH 9.5 with 20% aqueous ammonia, are added 10.2 ml of 6% aqueous hydrogen peroxide solution. After stirring for 24 hours at room temperature, the ethanol is removed and the coupling product formed is extracted with butanol. After removal of the butanol under vacuum, the gummy residue is taken up in ethyl acetate and then in ether. 0.470 g of 2-[[4-(2-amino-5-butoxy-4-iminocyclohexa-2,5-dienylideneamino)phenyl](2-hydroxyethyl)amino]ethanol 10 is obtained in the form of a blue-black powder after drying.

FIA/MS analysis: the molecular ion 387 (ES+) is mainly detected.

Example 6

Synthesis of 2-{[4-(2-amino-5-ethoxy-4-imino cyclohexa-2,5-dienylideneamino)phenyl]ethylamino}ethanol hydrochloride 65

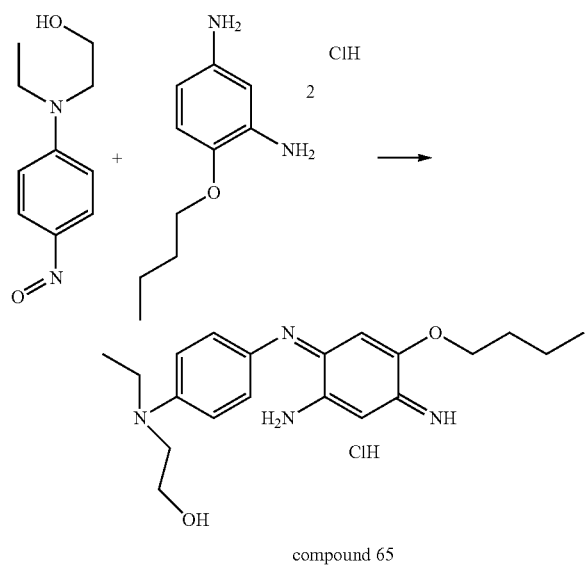

compound 65

A solution of 4-butoxybenzene-1,3-diamine dihydrochloride in 4.2 ml of 0.25N sodium hydroxide is added to a solution of 2-[ethyl(4-nitrosophenyl)amino]ethanol in 4.2 ml of water at 50° C. After 3 hours at 50° C., the supernatant is removed and the residual gum is washed with water and then taken up in isopropyl ether. The solid formed is filtered off and dried. 360 mg of 2-{[4-(2-amino-5-ethoxy-4-imino cyclohexa-2,5-dienylideneamino)phenyl]-ethylamino}ethanol hydrochloride 65 are thus obtained in the form of a black powder.

FIA/MS analysis: the molecular ion 357 (ES+) is detected.

Example 7

Synthesis of 2-{4-amino-3-[4-(ethylisopropylamino)phenylimino]-6-imino-cyclohexan-1,4-dienyloxy}ethanol hydrochloride 66

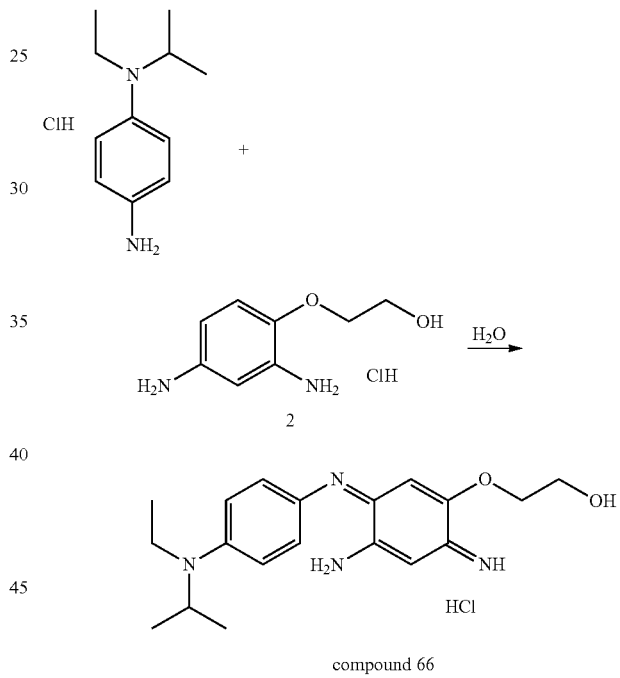

compound 66

To a solution of 2.14 g (0.01 mol) of N-ethyl-N-isopropyl-4-aminoaniline hydrochloride and 2.41 g (0.01 mol) of 2-(2,4-diaminophenoxy)ethanol dihydrochloride in 10 ml of water and 10 ml of ethanol, brought to pH 9.5 with 20% aqueous ammonia, are added dropwise 5.7 g of 30% aqueous peroxide hydrogen solution (0.05 mol). After stirring for 6 hours at room temperature, a gum forms. The supernatant is removed and the residual gum is washed with four times of water and then taken up in dichloromethane in order to perform a chromatography (eluent: dichloromethane/methanol 98/2 v/v). 510 mg of 2-{4-amino-3-[4-(ethylisopropylamino)phenylimino]-6-iminocyclohexa-1,4-dienyloxy}ethanol hydrochloride 66 are thus obtained in the form of a black powder.

FIA/MS analysis: the molecular ion 343 (ES+) is detected.

Example 8

Synthesis of 4-methoxy-6-[4-(N-ethyl-N-isopropylamino)phenylimino]-3-iminocyclohexa-1,4-dienyl-1-amine 67

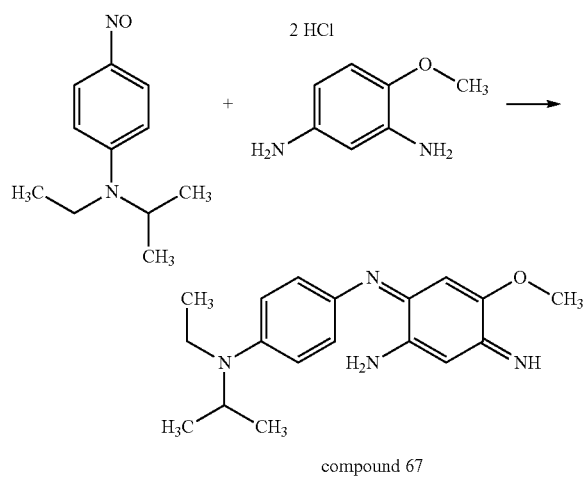

compound 67

To a solution of 191.5 mg (0.001 mol) of N-ethyl-N-(propan-2-yl)-4-nitrosoaniline and 312.4 mg of 4-methoxy-1,3-metaphenylenediamine dihydrochloride (0.0015 mol) in 2 ml of water and 2 ml of ethanol, is added 1 ml of 2 N sodium hydroxide. After stirring for 4 hours, the mixture is cooled to 0° C. then 2 ml of 20% aqueous ammonia is added and the mixture is stirred for 1 hour. The formed precipitate is filtrated and is washed with water.

258 mg of 4-methoxy-6-[4-(N-ethyl-N-isopropylamino) phenylimino]-3-iminocyclohexa-1,4-dienyl-1-amine are thus obtained in the form of a black powder.

LC/MS analysis: the molecular ion 313 (ES+) is detected.

2/Dyeing Evaluations of the Molecules 1, 2, 3, 8, 10, 65 Synthesized

The following dye compositions were prepared:
1 g of illustrated compound
79.5 g of water
15 g of ethanol
5 g of benzyl alcohol
0.5 g of benzoic acid
1 g of the resulting mixture is applied to a lock of 0.25 g of grey hair containing 90% white hairs. After a leave-on time of 30 minutes, the lock is rinsed, washed with a standard shampoo, rinsed again and then dried.

| Compound 1 | Very dark violet-blue |
| Compound 2 | Very dark violet-blue |
| Compound 3 | Very dark violet-blue |
| Compound 8 | Dark orange-brown |
| Compound 10 | Very dark blue-green |
| Compound 65 | Very dark violet-blue |

3/Dyeing Evaluations of the Molecules 66 and 67 Synthesized

The following dye composition was prepared:
0.5 g of illustrated compound
74.5 g of water
15 g of ethanol
5 g of benzyl alcohol
5 g of 30% aqueous hydroxyethyldimonium chloride solution 1.25 g of the resulting mixture is applied to a lock of 0.25 g of grey hair containing 90% white hairs. After a leave-on time of 30 minutes, the lock is rinsed, washed with a standard shampoo, rinsed again and then dried.

| Compound 66 | Very dark blue |
| Compound 67 | Very dark blue |

The invention claimed is:

1. An azomethine compound chosen from the following compounds, organic or mineral acid salts thereof, tautomeric forms, optical isomers or geometrical isomers thereof, or solvates thereof:

Compound 1

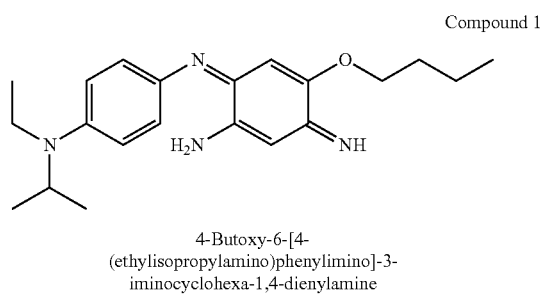

4-Butoxy-6-[4-(ethylisopropylamino)phenylimino]-3-iminocyclohexa-1,4-dienylamine Compound 2

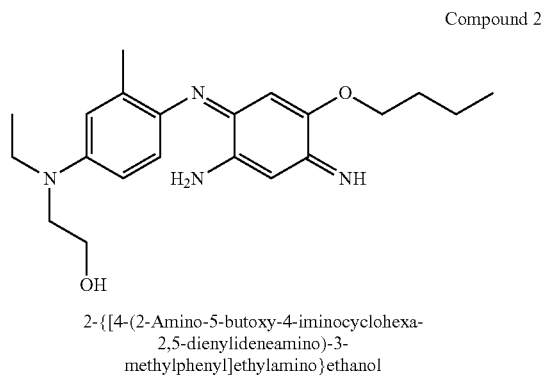

2-{[4-(2-Amino-5-butoxy-4-iminocyclohexa-2,5-dienylideneamino)-3-methylphenyl]ethylamino}ethanol Compound 3

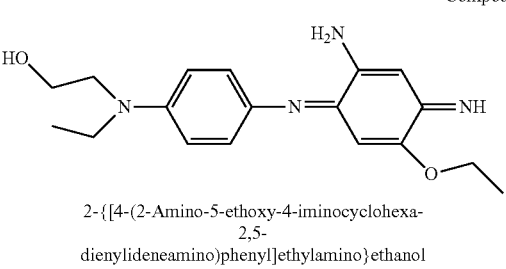

2-{[4-(2-Amino-5-ethoxy-4-iminocyclohexa-2,5-dienylideneamino)phenyl]ethylamino}ethanol Compound 4

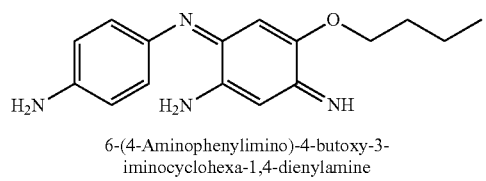

6-(4-Aminophenylimino)-4-butoxy-3-iminocyclohexa-1,4-dienylamine

Compound 5

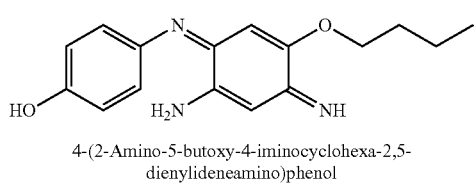

4-(2-Amino-5-butoxy-4-iminocyclohexa-2,5-dienylideneamino)phenol

Compound 6

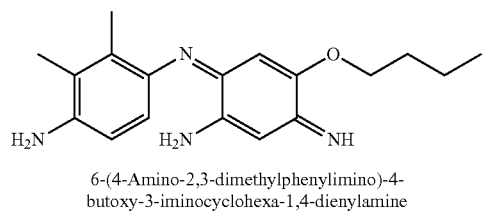

6-(4-Amino-2,3-dimethylphenylimino)-4-butoxy-3-iminocyclohexa-1,4-dienylamine

Compound 7

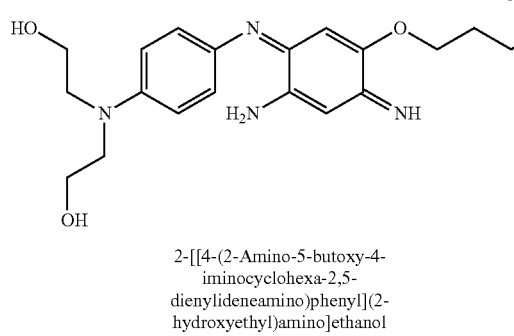

2-[[4-(2-Amino-5-butoxy-4-iminocyclohexa-2,5-dienylideneamino)phenyl](2-hydroxyethyl)amino]ethanol Compound 8

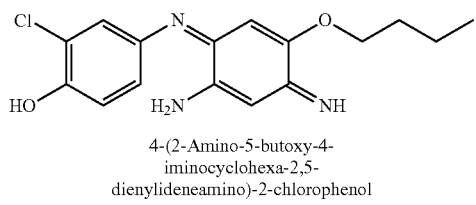

4-(2-Amino-5-butoxy-4-iminocyclohexa-2,5-dienylideneamino)-2-chlorophenol

Compound 9

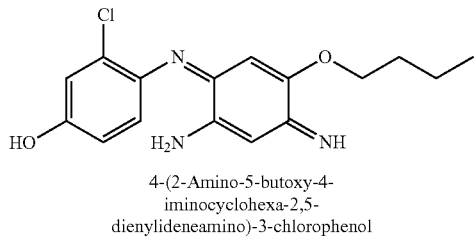

4-(2-Amino-5-butoxy-4-iminocyclohexa-2,5-dienylideneamino)-3-chlorophenol

Compound 10

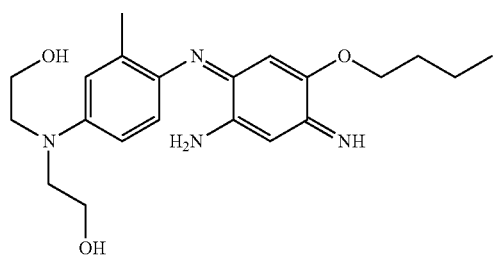

2-[[4-(2-Amino-5-butoxy-4-iminocyclohexa-2,5-dienylideneamino)-3-methylphenyl](2-hydroxyethyl)amino]ethanol Compound 11

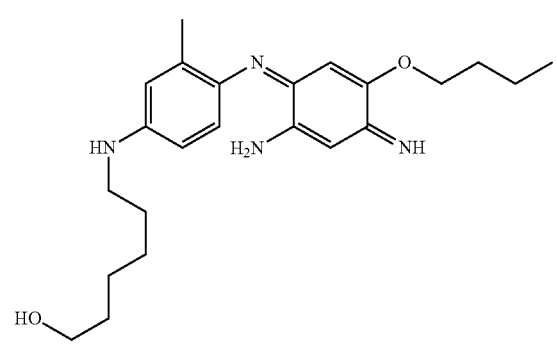

6-[4-(2-Amino-5-butoxy-4-iminocyclohexa-2,5-dienylideneamino)-3-methylphenylamino]hexan-1-ol Compound 12

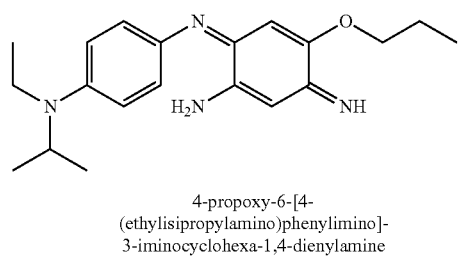

4-propoxy-6-[4-(ethylisipropylamino)phenylimino]-3-iminocyclohexa-1,4-dienylamine Compound 13

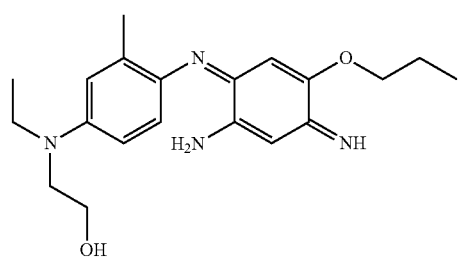

2-{[4-(2-Amino-5-propoxy-4-iminocyclohexa-2,5-dienylideneamino)-3-methylphenyl]ethylamino}ethanol Compound 14

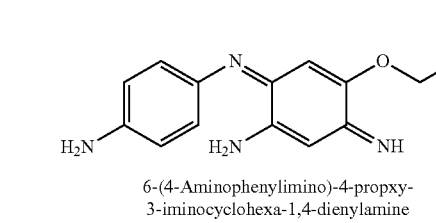

6-(4-Aminophenylimino)-4-propxy-
3-iminocyclohexa-1,4-dienylamine

Compound 15

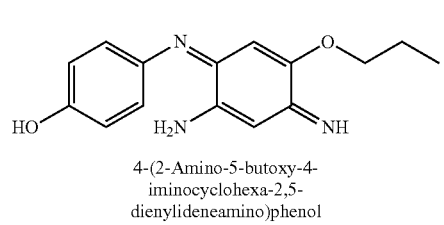

4-(2-Amino-5-butoxy-4-
iminocyclohexa-2,5-
dienylideneamino)phenol

Compound 16

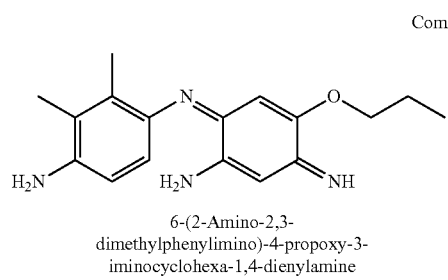

6-(2-Amino-2,3-
dimethylphenylimino)-4-propoxy-3-
iminocyclohexa-1,4-dienylamine Compound 17

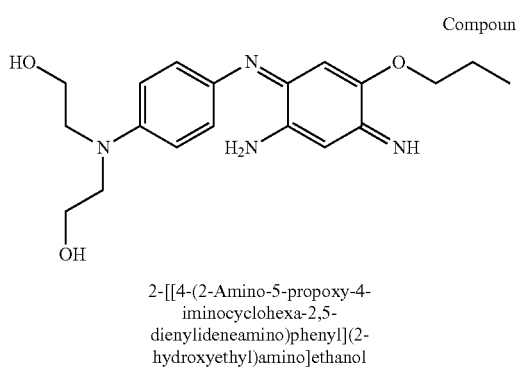

2-[[4-(2-Amino-5-propoxy-4-
iminocyclohexa-2,5-
dienylideneamino)phenyl](2-
hydroxyethyl)amino]ethanol Compound 18

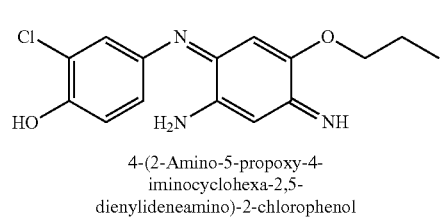

4-(2-Amino-5-propoxy-4-
iminocyclohexa-2,5-
dienylideneamino)-2-chlorophenol

Compound 19

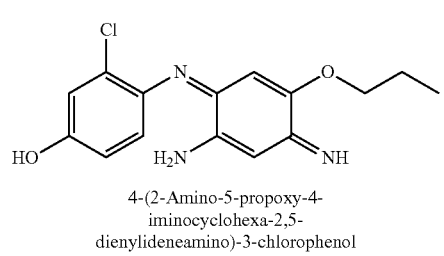

4-(2-Amino-5-propoxy-4-
iminocyclohexa-2,5-
dienylideneamino)-3-chlorophenol

Compound 20

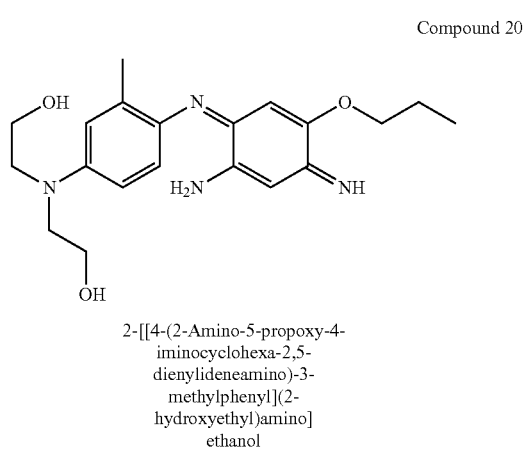

2-[[4-(2-Amino-5-propoxy-4-
iminocyclohexa-2,5-
dienylideneamino)-3-
methylphenyl](2-
hydroxyethyl)amino]
ethanol Compound 21

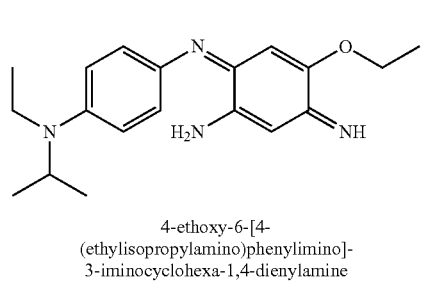

4-ethoxy-6-[4-
(ethylisopropylamino)phenylimino]-
3-iminocyclohexa-1,4-dienylamine Compound 22

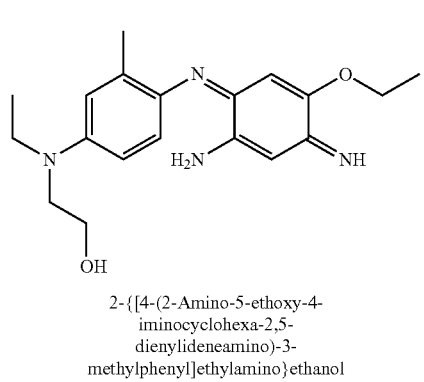

2-{[4-(2-Amino-5-ethoxy-4-
iminocyclohexa-2,5-
dienylideneamino)-3-
methylphenyl]ethylamino}ethanol Compound 23

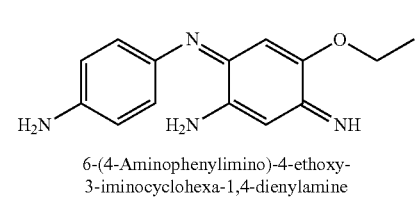

6-(4-Aminophenylimino)-4-ethoxy-
3-iminocyclohexa-1,4-dienylamine

Compound 24

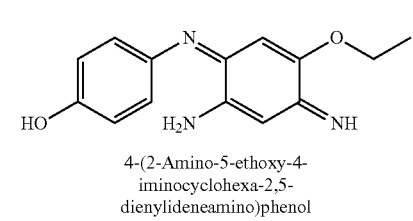

4-(2-Amino-5-ethoxy-4-
iminocyclohexa-2,5-
dienylideneamino)phenol

-continued

Compound 25

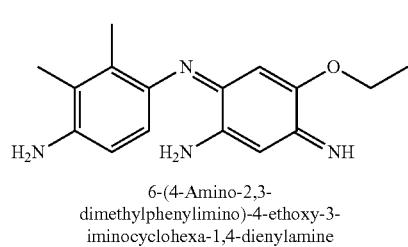

6-(4-Amino-2,3-dimethylphenylimino)-4-ethoxy-3-iminocyclohexa-1,4-dienylamine

Compound 26

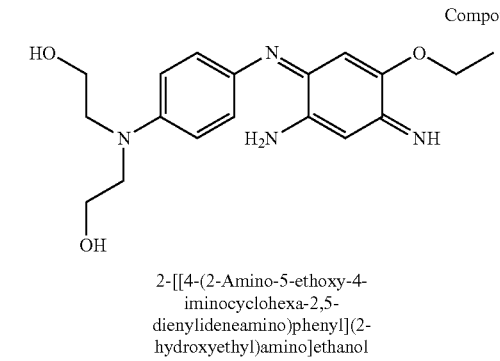

2-[[4-(2-Amino-5-ethoxy-4-iminocyclohexa-2,5-dienylideneamino)phenyl](2-hydroxyethyl)amino]ethanol Compound 27

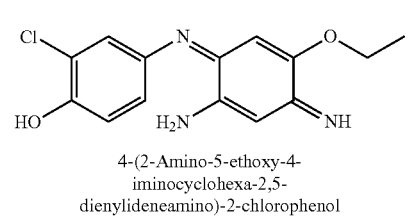

4-(2-Amino-5-ethoxy-4-iminocyclohexa-2,5-dienylideneamino)-2-chlorophenol

Compound 28

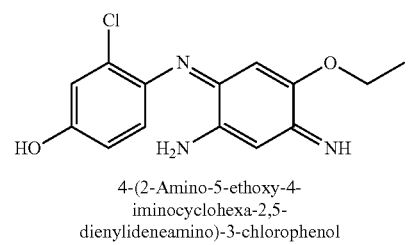

4-(2-Amino-5-ethoxy-4-iminocyclohexa-2,5-dienylideneamino)-3-chlorophenol

Compound 29

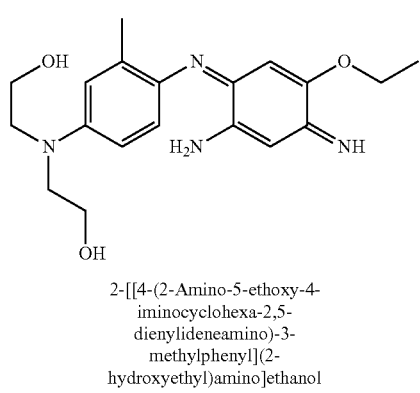

2-[[4-(2-Amino-5-ethoxy-4-iminocyclohexa-2,5-dienylideneamino)-3-methylphenyl](2-hydroxyethyl)amino]ethanol -continued Compound 30

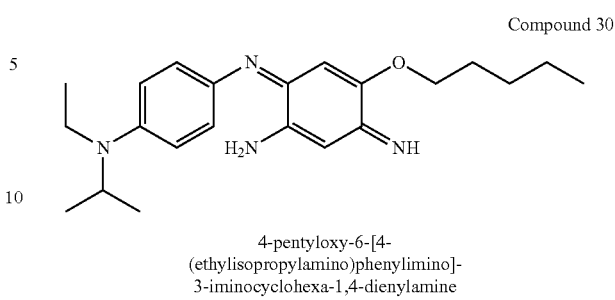

4-pentyloxy-6-[4-(ethylisopropylamino)phenylimino]-3-iminocyclohexa-1,4-dienylamine Compound 31

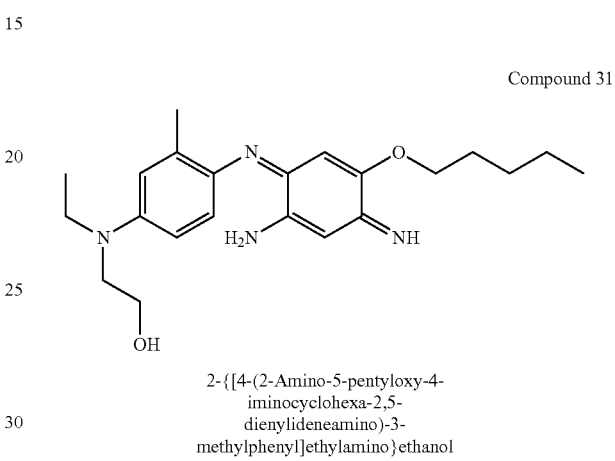

2-{[4-(2-Amino-5-pentyloxy-4-iminocyclohexa-2,5-dienylideneamino)-3-methylphenyl]ethylamino}ethanol Compound 32

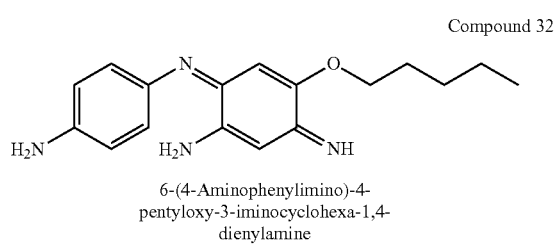

6-(4-Aminophenylimino)-4-pentyloxy-3-iminocyclohexa-1,4-dienylamine

Compound 33

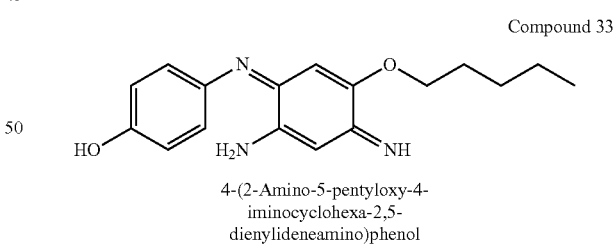

4-(2-Amino-5-pentyloxy-4-iminocyclohexa-2,5-dienylideneamino)phenol

Compound 34

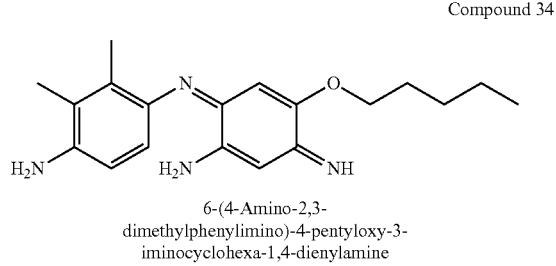

6-(4-Amino-2,3-dimethylphenylimino)-4-pentyloxy-3-iminocyclohexa-1,4-dienylamine Compound 35

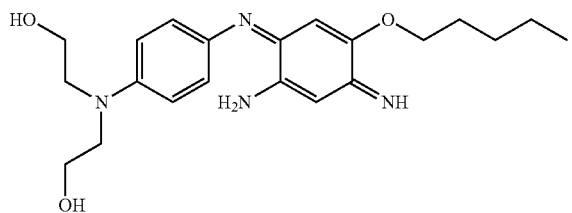

2-[[4-(2-Amino-5-pentyloxy-4-iminocyclohexa-2,5-dienylideneamino)phenyl(2-hydroxyethyl)amino]ethanol Compound 36

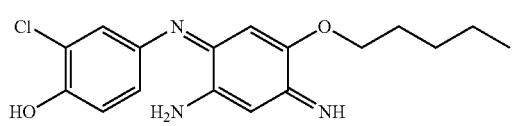

4-(2-Amino-5-pentyloxy-4-iminocyclohexa-2,5-dienylideneamino)-2-chlorophenol

Compound 37

4-(2-Amino-5-pentyloxy-4-iminocyclohexa-2,5-dienylideneamino)-3-chlorophenol

Compound 38

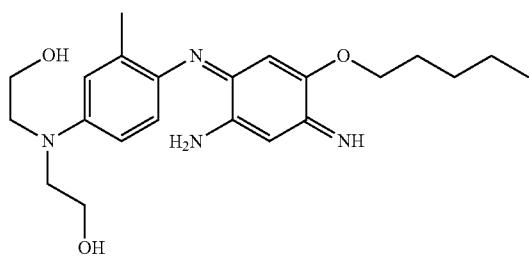

2-[[4-(2-Amino-5-pentyloxy-4-iminocyclohexa-2,5-dienylideneamino)-3-methylphenyl](2-hydroxyethyl)amino]ethanol Compound 39

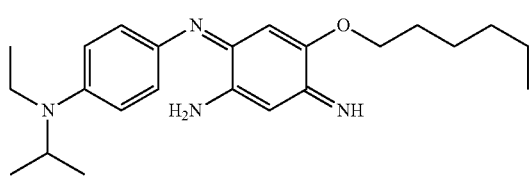

4-hexyloxy-6-[4-(ethylisopropylamino)phenylimino]-3-iminocyclohexa-1,4-dienylamine Compound 40

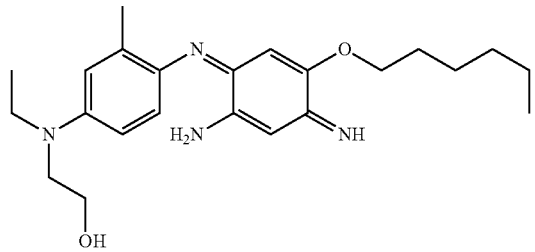

2-{[4-(2-Amino-5-hexyloxy-4-iminocyclohexa-2,5-dienylideneamino)-3-methylphenyl]ethylamino}ethanol Compound 41

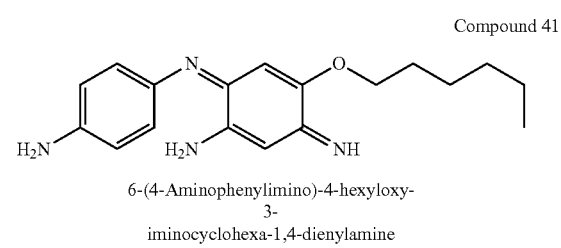

6-(4-Aminophenylimino)-4-hexyloxy-3-iminocyclohexa-1,4-dienylamine

Compound 42

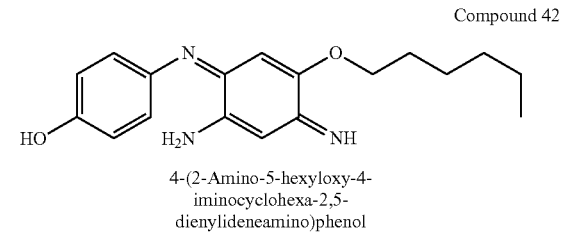

4-(2-Amino-5-hexyloxy-4-iminocyclohexa-2,5-dienylideneamino)phenol

Compound 43

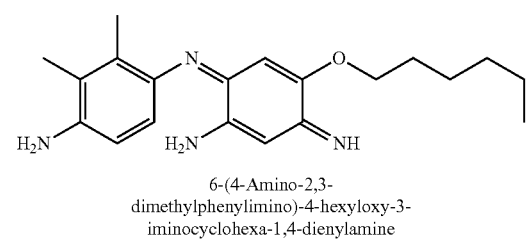

6-(4-Amino-2,3-dimethylphenylimino)-4-hexyloxy-3-iminocyclohexa-1,4-dienylamine

Compound 44

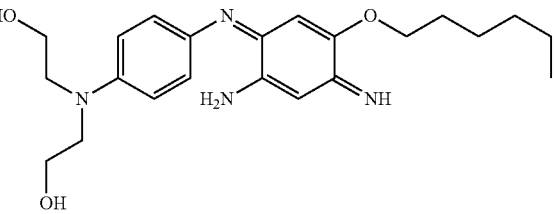

2-[[4-(2-Amino-5-hexyloxy-4-iminocyclohexa-2,5-dienylideneamino)phenyl(2-hydroxyethyl)amino]ethanol -continued Compound 45

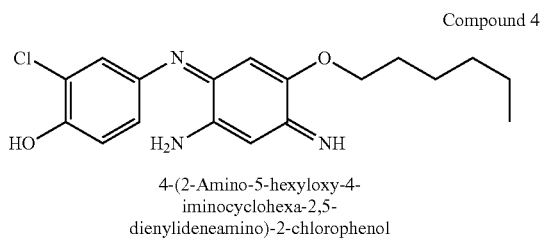

4-(2-Amino-5-hexyloxy-4-iminocyclohexa-2,5-dienylideneamino)-2-chlorophenol

Compound 46

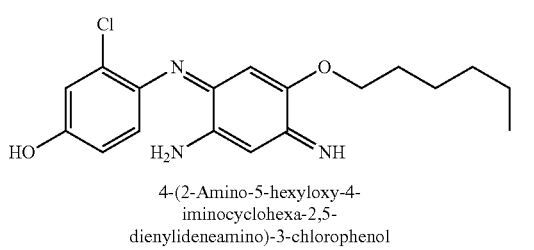

4-(2-Amino-5-hexyloxy-4-iminocyclohexa-2,5-dienylideneamino)-3-chlorophenol

Compound 47

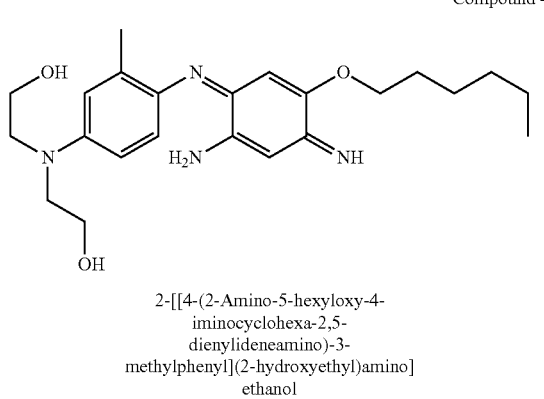

2-[[4-(2-Amino-5-hexyloxy-4-iminocyclohexa-2,5-dienylideneamino)-3-methylphenyl](2-hydroxyethyl)amino]ethanol Compound 48

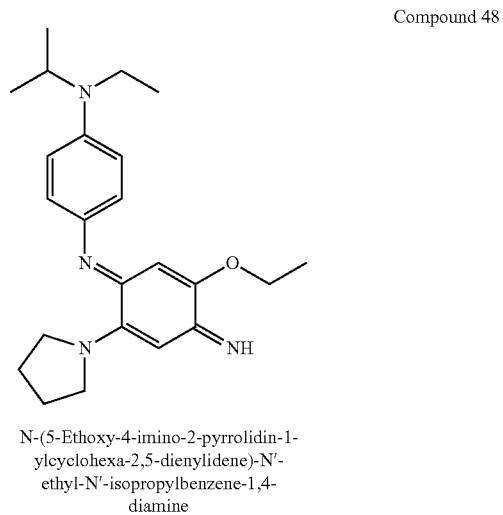

N-(5-Ethoxy-4-imino-2-pyrrolidin-1-ylcyclohexa-2,5-dienylidene)-N'-ethyl-N'-isopropylbenzene-1,4-diamine Compound 49

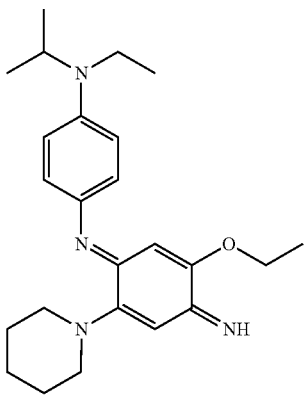

N-(5-Ethoxy-4-imino-2-piperidin-1-ylcyclohexa-2,5-dienylidene)-N'-ethyl-N'-isopropylbenzene-1,4-diamine Compound 50

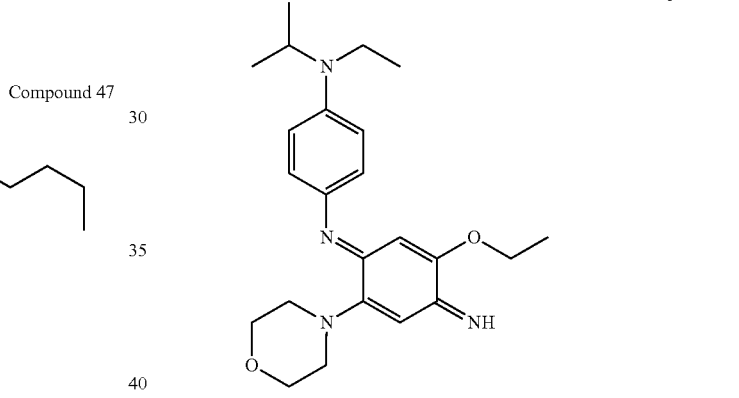

N-(5-Ethoxy-4-imino-2-morpholin-4-ylcyclohexa-2,5-dienylidene)-N'-ethyl-N'-isopropylbenzene-1,4-diamine Compound 51

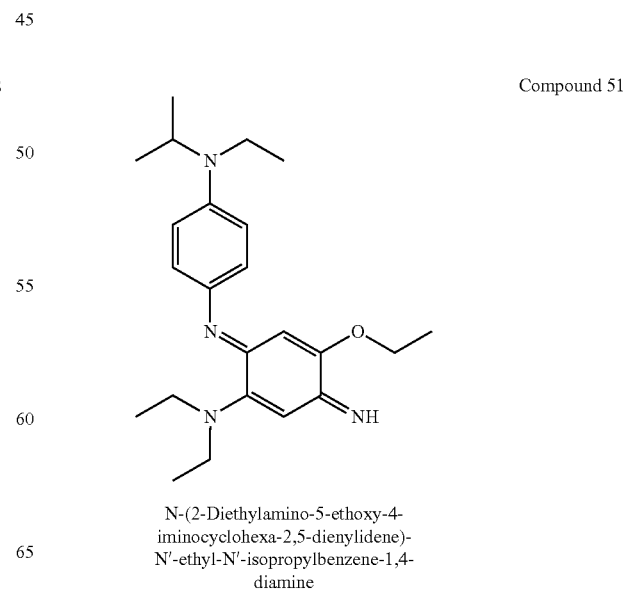

N-(2-Diethylamino-5-ethoxy-4-iminocyclohexa-2,5-dienylidene)-N'-ethyl-N'-isopropylbenzene-1,4-diamine Compound 52

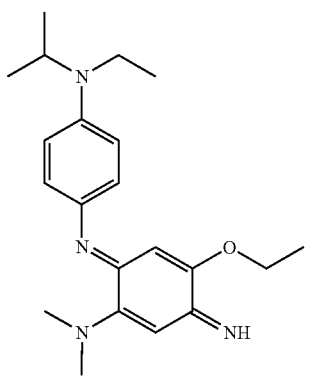

N-(2-methylamino-5-ethoxy-4-
iminocyclohexa-2,5-dienylidene)-
N'-ethyl-N'-isopropylbenzene-1,4-
diamine Compound 53

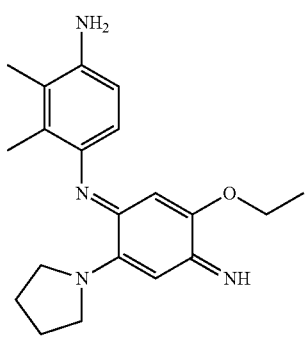

N-(5-Ethoxy-4-imino-2-pyrrolidin-
1-ylcyclohexa-2,5-dienylidene)-
2,3-dimethylbenzene-1,4-diamine Compound 54

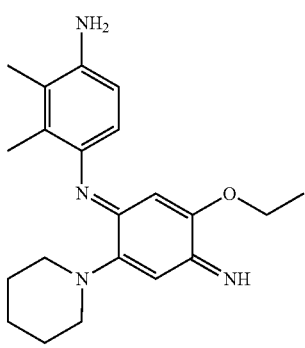

N-(5-Ethoxy-4-imino-2-piperidin-1-
ylcyclohexa-2,5-dienylidene)-2,3-
dimethylbenzene-1,4-
diamine Compound 55

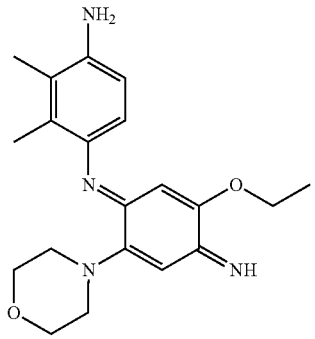

N-(5-Ethoxy-4-imino-2-
morpholin-4-ylcyclohexa-2,5-
dienylidene)-2,3-
dimethylbenzene-1,4-
diamine Compound 56

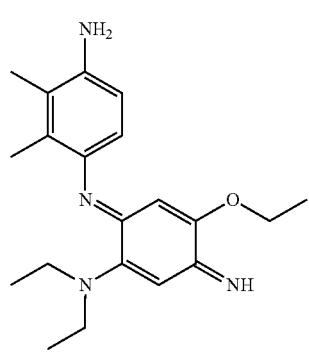

N-(2-Diethylamino-5-ethoxy-4-
iminocyclohexa-2,5-dienylidene)-
2,3-dimethylbenzene-1,4-
diamine Compound 57

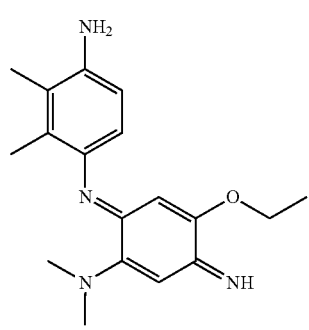

N-(2-Dimethylamino-5-ethoxy-4-
iminocyclohexa-2,5-dienylidene)-
2,3-dimethylbenzene-1,4-
diamine Compound 58

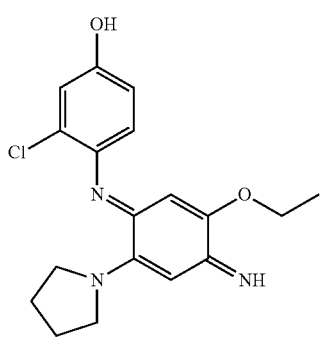

3-Chloro-4-(5-ethoxy-4-imino-2-pyrrolidin-1-ylcyclohexa-2,5-dienylideneamino)phenol Compound 59

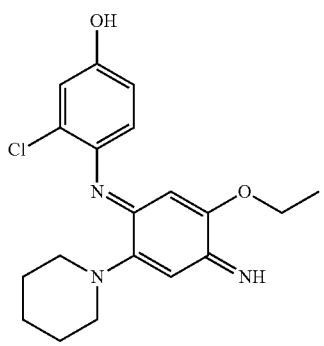

3-Chloro-4-(5-ethoxy-4-imino-2-piperidin-1-ylcyclohexa-2,5-dienylideneamino)phenol Compound 60

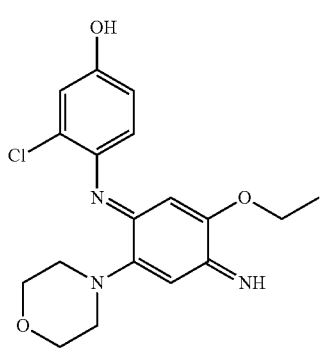

3-Chloro-4-(5-ethoxy-4-imino-2-morpholin-4-ylcyclohexa-2,5-dienylideneamino)phenol Compound 61

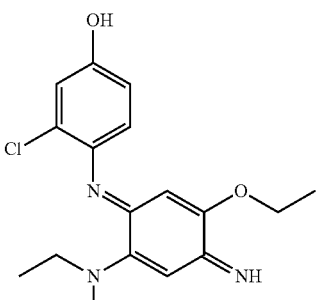

3-Chloro-4-(2-diethylamino-5-ethoxy-4-iminocyclohexa-2,5-dienylideneamino)phenol Compound 62

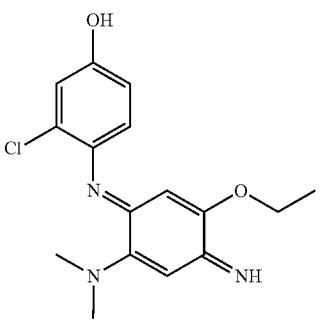

3-Chloro-4-(2-diethylamino-5-ethoxy-4-iminocyclohexa-2,5-dienylideneamino)phenol Compound 63

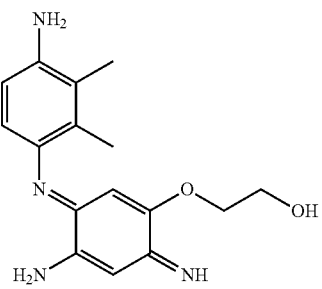

2-{4-Amino-3-[4-amino-2,3-dimethylphenylimino]-6-iminocyclohexa-1,4-dienyloxy}ethanol Compound 64

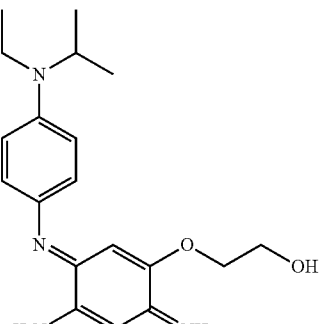

2-{4-Amino-3-[4-(ethylisopropylamino)phenylimino]-6-iminocyclohexa-1,4-dienyloxy}ethanol Compound 65

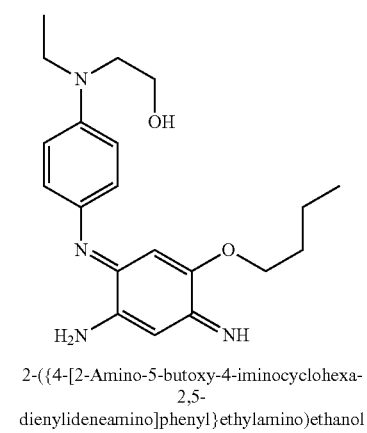

2-({4-[2-Amino-5-butoxy-4-iminocyclohexa-2,5-dienylideneamino]phenyl}ethylamino)ethanol Compound 66

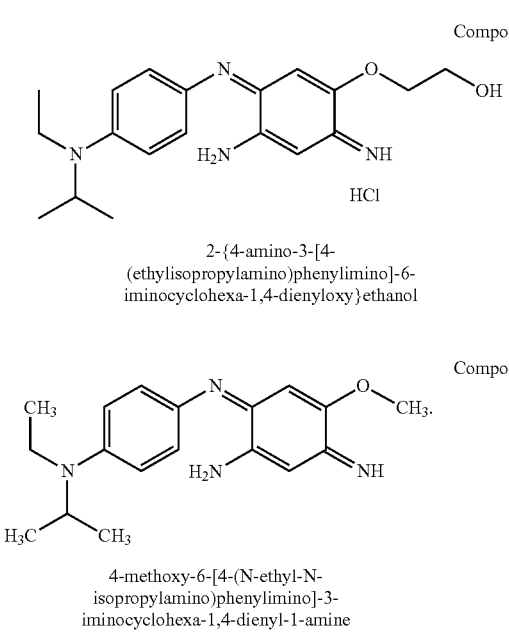

2-{4-amino-3-[4-(ethylisopropylamino)phenylimino]-6-iminocyclohexa-1,4-dienyloxy}ethanol Compound 67

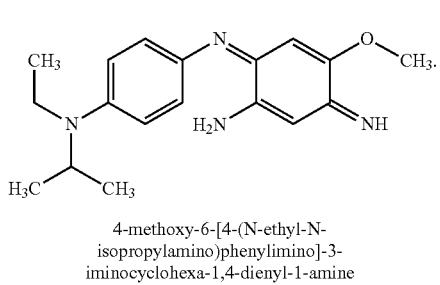

4-methoxy-6-[4-(N-ethyl-N-isopropylamino)phenylimino]-3-iminocyclohexa-1,4-dienyl-1-amine 2. Composition for dyeing keratin fibers, comprising at least one azomethine compound chosen from the following compounds, organic or mineral acid salts thereof, tautomeric forms, optical isomers or geometrical isomers thereof, or solvates thereof:

Compound 1

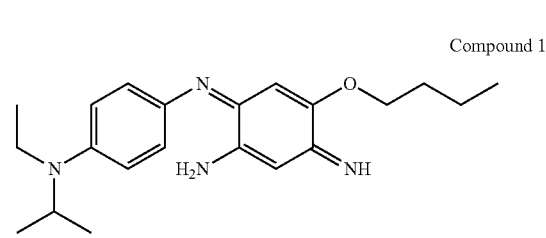

4-Butoxy-6-[4-(ethylisopropylamino)phenylimino]-3-iminocyclohexa-1,4-dienylamine Compound 2

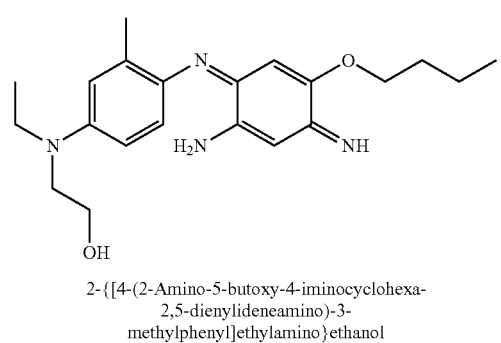

2-{[4-(2-Amino-5-butoxy-4-iminocyclohexa-2,5-dienylideneamino)-3-methylphenyl]ethylamino}ethanol Compound 3

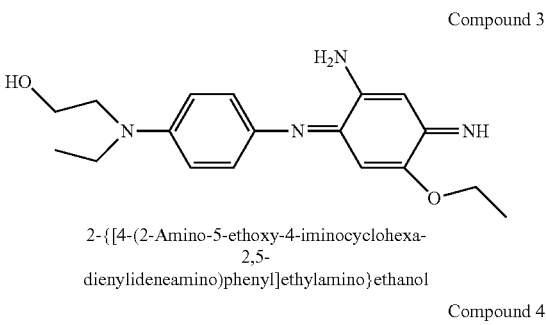

2-{[4-(2-Amino-5-ethoxy-4-iminocyclohexa-2,5-dienylideneamino)phenyl]ethylamino}ethanol Compound 4

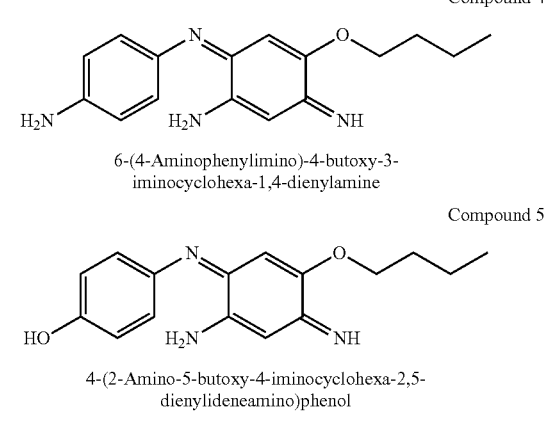

6-(4-Aminophenylimino)-4-butoxy-3-iminocyclohexa-1,4-dienylamine

Compound 5

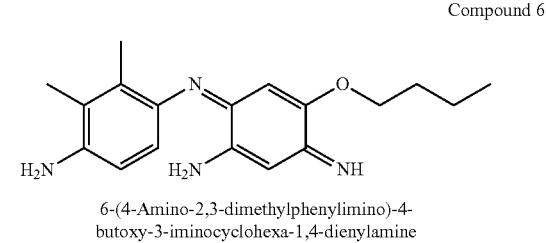

4-(2-Amino-5-butoxy-4-iminocyclohexa-2,5-dienylideneamino)phenol

Compound 6

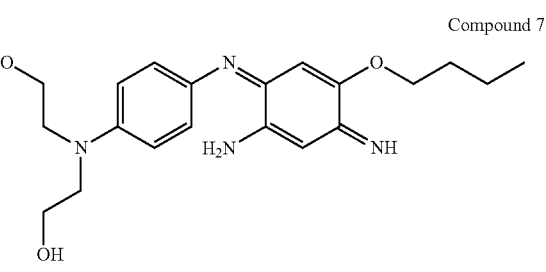

6-(4-Amino-2,3-dimethylphenylimino)-4-butoxy-3-iminocyclohexa-1,4-dienylamine

Compound 7

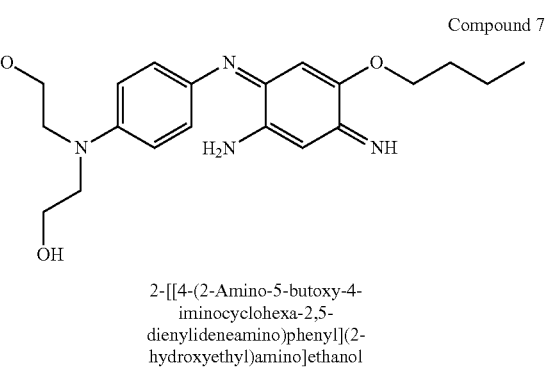

2-[[4-(2-Amino-5-butoxy-4-iminocyclohexa-2,5-dienylideneamino)phenyl](2-hydroxyethyl)amino]ethanol Compound 8

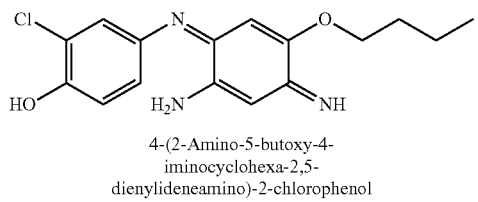

4-(2-Amino-5-butoxy-4-iminocyclohexa-2,5-dienylideneamino)-2-chlorophenol

Compound 9

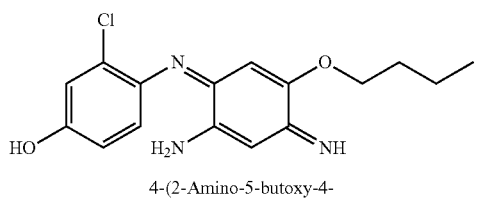

4-(2-Amino-5-butoxy-4-iminocyclohexa-2,5-dienylideneamino)-3-chlorophenol

Compound 10

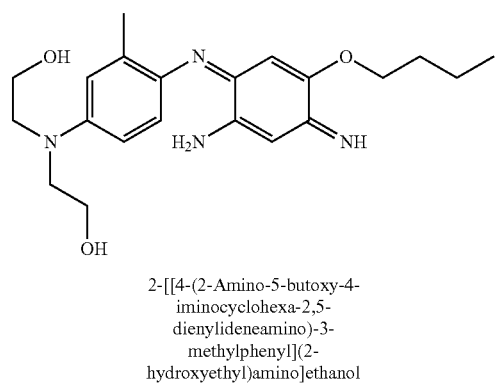

2-[[4-(2-Amino-5-butoxy-4-iminocyclohexa-2,5-dienylideneamino)-3-methylphenyl](2-hydroxyethyl)amino]ethanol Compound 11

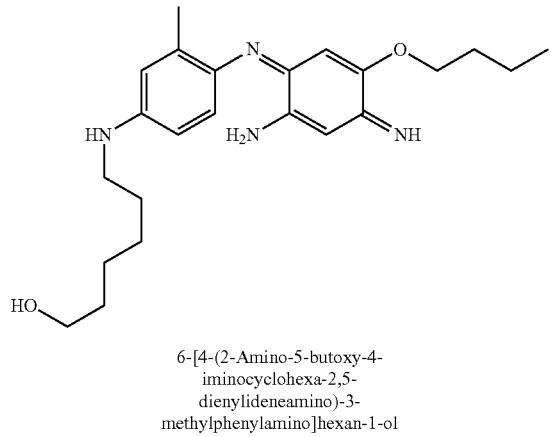

6-[4-(2-Amino-5-butoxy-4-iminocyclohexa-2,5-dienylideneamino)-3-methylphenylamino]hexan-1-ol Compound 12

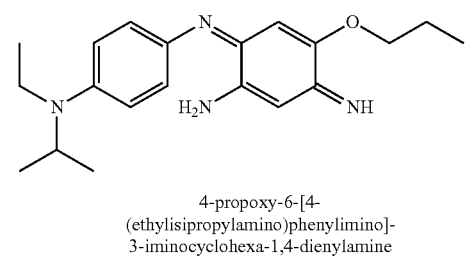

4-propoxy-6-[4-(ethylisipropylamino)phenylimino]-3-iminocyclohexa-1,4-dienylamine Compound 13

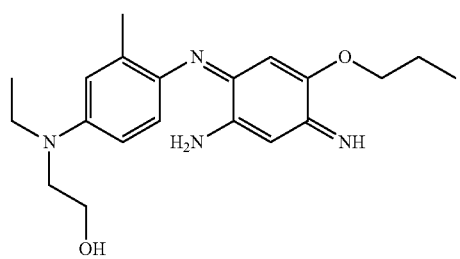

2-{[4-(2-Amino-5-propoxy-4-iminocyclohexa-2,5-dienylideneamino)-3-methylphenyl]ethylamino}ethanol Compound 14

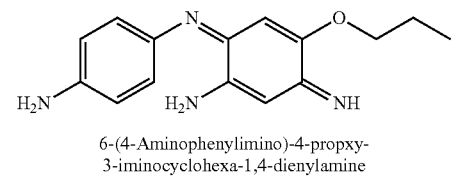

6-(4-Aminophenylimino)-4-propxy-3-iminocyclohexa-1,4-dienylamine

Compound 15

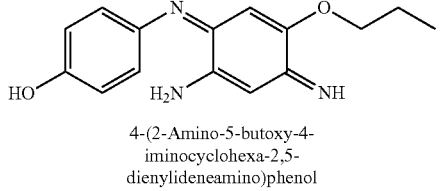

4-(2-Amino-5-butoxy-4-iminocyclohexa-2,5-dienylideneamino)phenol

Compound 16

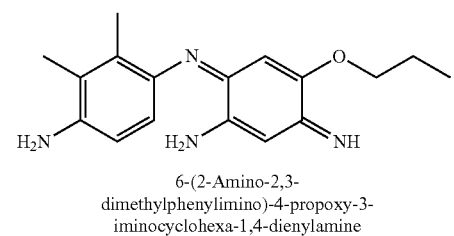

6-(2-Amino-2,3-dimethylphenylimino)-4-propoxy-3-iminocyclohexa-1,4-dienylamine

Compound 17

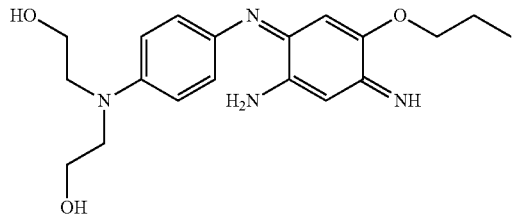

2-[[4-(2-Amino-5-propoxy-4-iminocyclohexa-2,5-dienylideneamino)phenyl](2-hydroxyethyl)amino]ethanol Compound 18

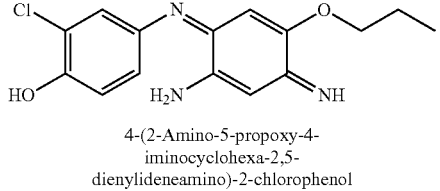

4-(2-Amino-5-propoxy-4-iminocyclohexa-2,5-dienylideneamino)-2-chlorophenol

Compound 19

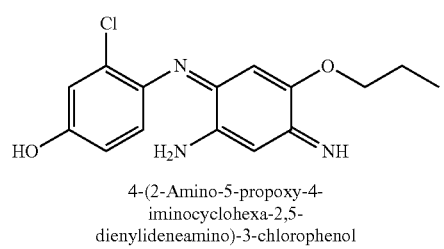

4-(2-Amino-5-propoxy-4-
iminocyclohexa-2,5-
dienylideneamino)-3-chlorophenol

Compound 20

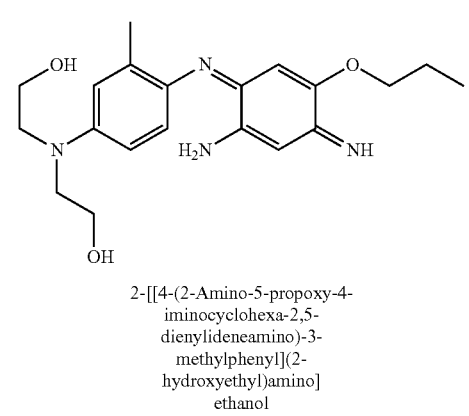

2-[[4-(2-Amino-5-propoxy-4-
iminocyclohexa-2,5-
dienylideneamino)-3-
methylphenyl](2-
hydroxyethyl)amino]
ethanol Compound 21

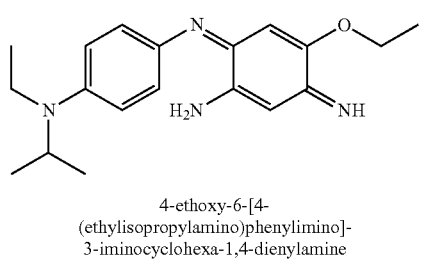

4-ethoxy-6-[4-
(ethylisopropylamino)phenylimino]-
3-iminocyclohexa-1,4-dienylamine Compound 22

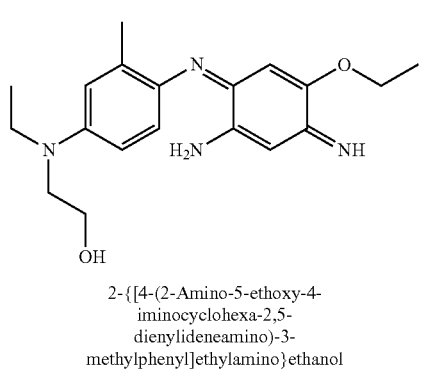

2-{[4-(2-Amino-5-ethoxy-4-
iminocyclohexa-2,5-
dienylideneamino)-3-
methylphenyl]ethylamino}ethanol Compound 23

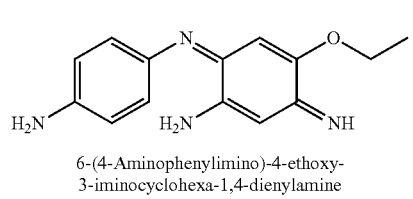

6-(4-Aminophenylimino)-4-ethoxy-
3-iminocyclohexa-1,4-dienylamine

Compound 24

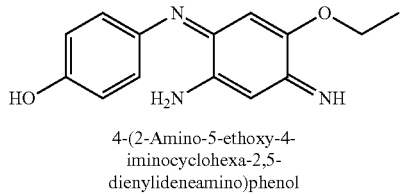

4-(2-Amino-5-ethoxy-4-
iminocyclohexa-2,5-
dienylideneamino)phenol

Compound 25

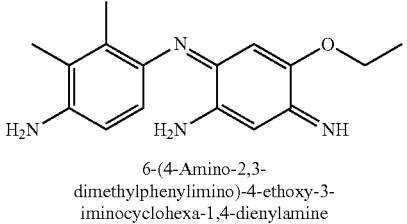

6-(4-Amino-2,3-
dimethylphenylimino)-4-ethoxy-3-
iminocyclohexa-1,4-dienylamine

Compound 26

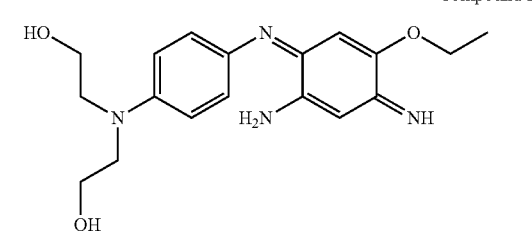

2-[[4-(2-Amino-5-ethoxy-4-
iminocyclohexa-2,5-
dienylideneamino)phenyl](2-
hydroxyethyl)amino]ethanol Compound 27

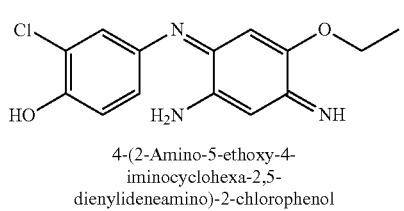

4-(2-Amino-5-ethoxy-4-
iminocyclohexa-2,5-
dienylideneamino)-2-chlorophenol

Compound 28

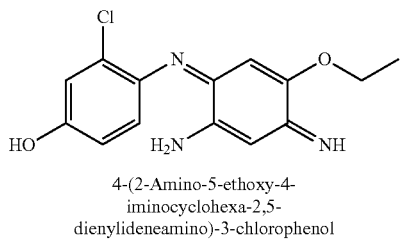

4-(2-Amino-5-ethoxy-4-
iminocyclohexa-2,5-
dienylideneamino)-3-chlorophenol

Compound 29

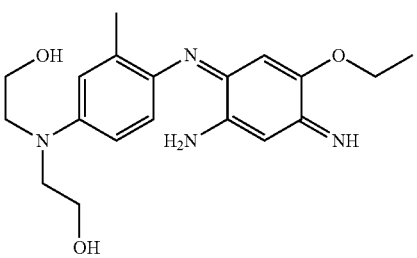

2-[[4-(2-Amino-5-ethoxy-4-
iminocyclohexa-2,5-
dienylideneamino)-3-
methylphenyl](2-
hydroxyethyl)amino]ethanol Compound 30

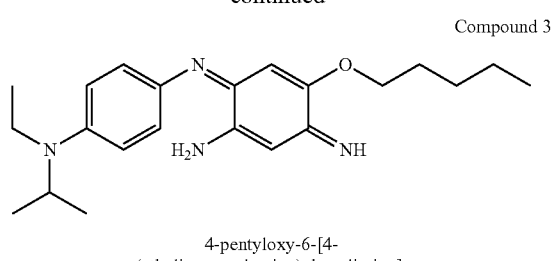

4-pentyloxy-6-[4-
(ethylisopropylamino)phenylimino]-
3-iminocyclohexa-1,4-dienylamine Compound 31

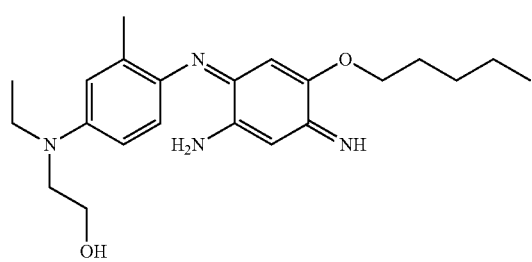

2-{[4-(2-Amino-5-pentyloxy-4-
iminocyclohexa-2,5-
dienylideneamino)-3-
methylphenyl]ethylamino}ethanol Compound 32

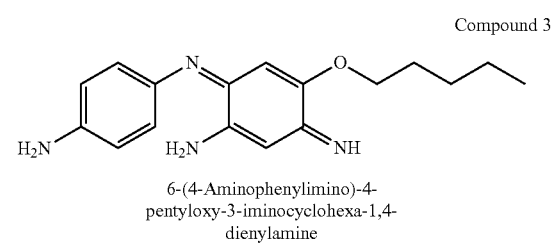

6-(4-Aminophenylimino)-4-
pentyloxy-3-iminocyclohexa-1,4-
dienylamine

Compound 33

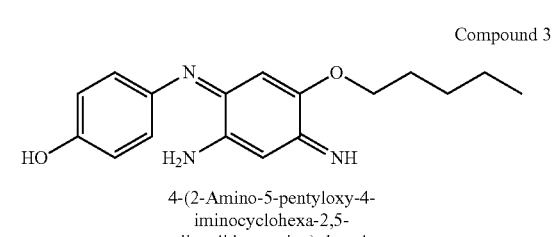

4-(2-Amino-5-pentyloxy-4-
iminocyclohexa-2,5-
dienylideneamino)phenol

Compound 34

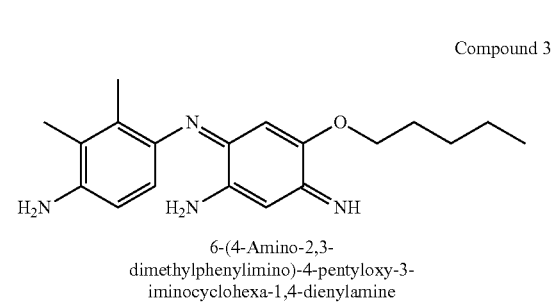

6-(4-Amino-2,3-
dimethylphenylimino)-4-pentyloxy-3-
iminocyclohexa-1,4-dienylamine Compound 35

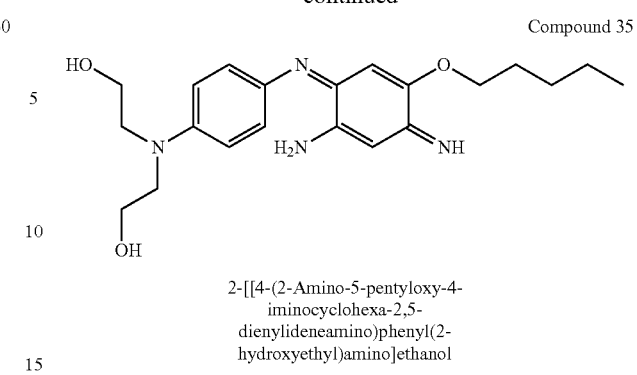

2-[[4-(2-Amino-5-pentyloxy-4-
iminocyclohexa-2,5-
dienylideneamino)phenyl(2-
hydroxyethyl)amino]ethanol Compound 36

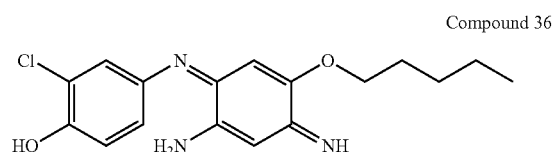

4-(2-Amino-5-pentyloxy-4-
iminocyclohexa-2,5-
dienylideneamino)-2-chlorophenol

Compound 37

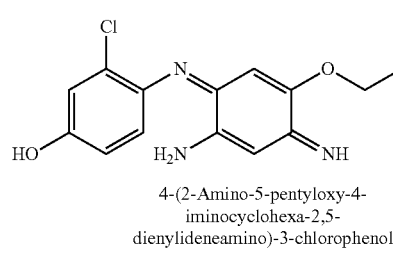

4-(2-Amino-5-pentyloxy-4-
iminocyclohexa-2,5-
dienylideneamino)-3-chlorophenol

Compound 38

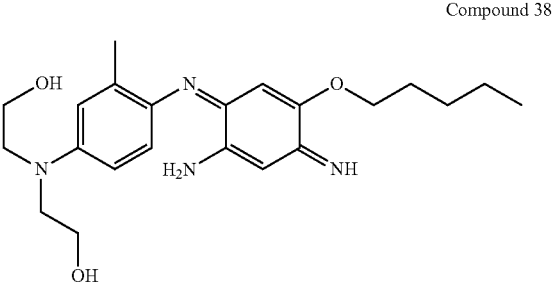

2-[[4-(2-Amino-5-pentyloxy-4-
iminocyclohexa-2,5-
dienylideneamino)-3-
methylphenyl](2-
hydroxyethyl)amino]ethanol Compound 39

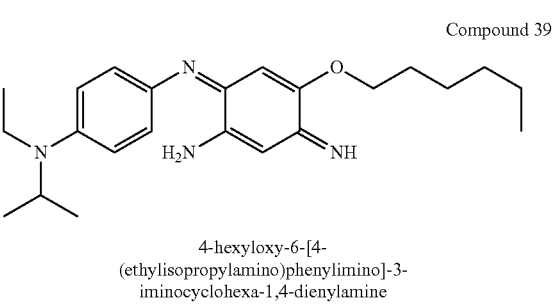

4-hexyloxy-6-[4-
(ethylisopropylamino)phenylimino]-3-
iminocyclohexa-1,4-dienylamine Compound 40

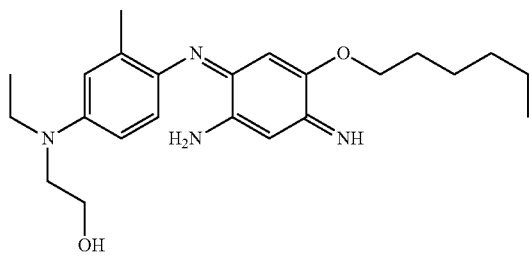

2-{[4-(2-Amino-5-hexyloxy-4-iminocyclohexa-2,5-dienylideneamino)-3-methylphenyl]ethylamino}ethanol Compound 41

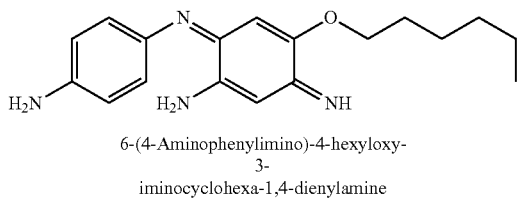

6-(4-Aminophenylimino)-4-hexyloxy-3-iminocyclohexa-1,4-dienylamine

Compound 42

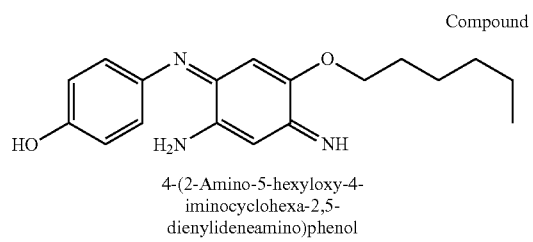

4-(2-Amino-5-hexyloxy-4-iminocyclohexa-2,5-dienylideneamino)phenol

Compound 43

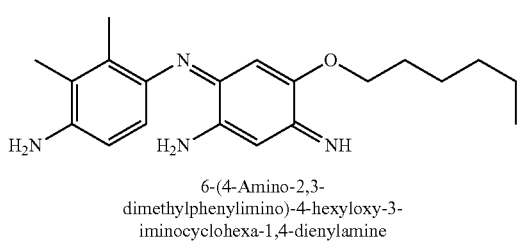

6-(4-Amino-2,3-dimethylphenylimino)-4-hexyloxy-3-iminocyclohexa-1,4-dienylamine

Compound 44

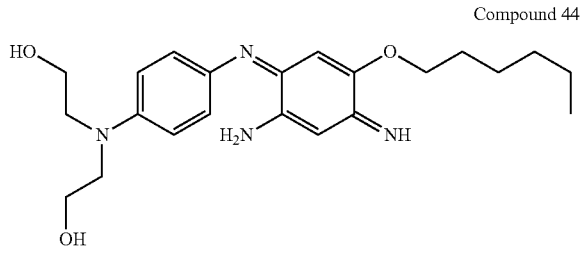

2-[[4-(2-Amino-5-hexyloxy-4-iminocyclohexa-2,5-dienylideneamino)phenyl(2-hydroxyethyl)amino]ethanol Compound 45

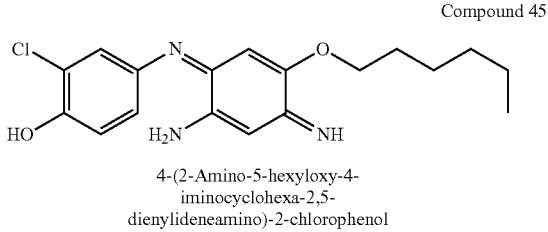

4-(2-Amino-5-hexyloxy-4-iminocyclohexa-2,5-dienylideneamino)-2-chlorophenol

Compound 46

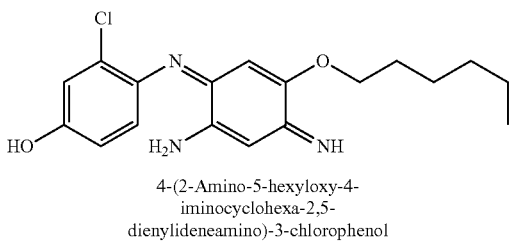

4-(2-Amino-5-hexyloxy-4-iminocyclohexa-2,5-dienylideneamino)-3-chlorophenol

Compound 47

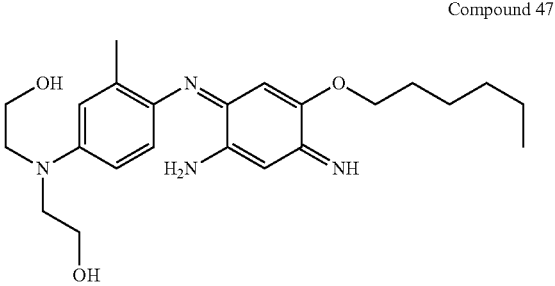

2-[[4-(2-Amino-5-hexyloxy-4-iminocyclohexa-2,5-dienylideneamino)-3-methylphenyl](2-hydroxyethyl)amino]ethanol Compound 48

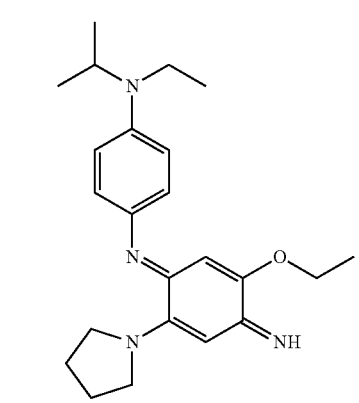

N-(5-Ethoxy-4-imino-2-pyrrolidin-1-ylcyclohexa-2,5-dienylidene)-N'-ethyl-N'-isopropylbenzene-1,4-diamine Compound 49

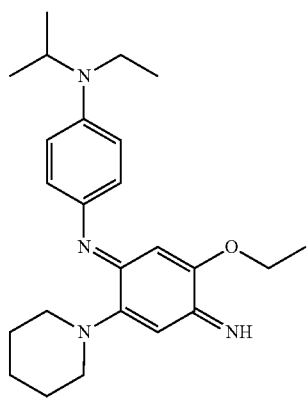

N-(5-Ethoxy-4-imino-2-piperidin-1-
ylcyclohexa-2,5-dienylidene)-N'-
ethyl-N'-isopropylbenzene-1,4-
diamine Compound 50

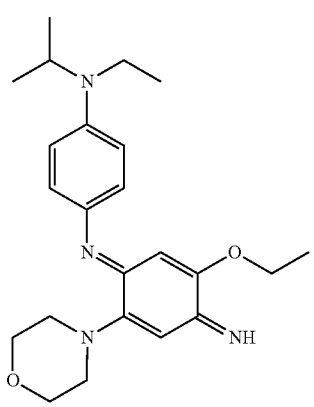

N-(5-Ethoxy-4-imino-2-morpholin-
4-ylcyclohexa-2,5-dienylidene)-N'-
ethyl-N'-isopropylbenzene-1,4-
diamine Compound 51

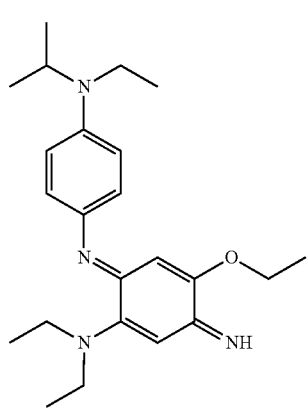

N-(2-Diethylamino-5-ethoxy-4-
iminocyclohexa-2,5-dienylidene)-
N'-ethyl-N'-isopropylbenzene-1,4-
diamine Compound 52

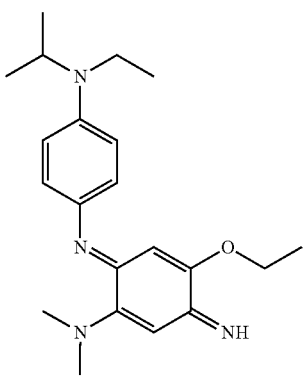

N-(2-methylamino-5-ethoxy-4-
iminocyclohexa-2,5-dienylidene)-
N'-ethyl-N'-isopropylbenzene-1,4-
diamine Compound 53

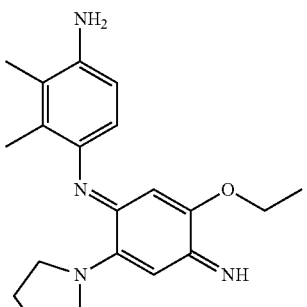

N-(5-Ethoxy-4-imino-2-pyrrolidin-
1-ylcyclohexa-2,5-dienylidene)-
2,3-dimethylbenzene-1,4-diamine Compound 54

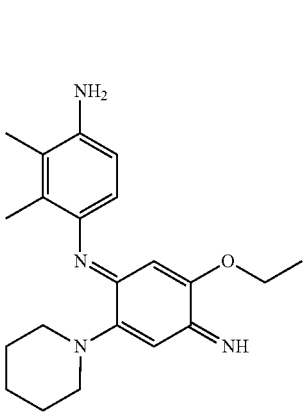

N-(5-Ethoxy-4-imino-2-piperidin-1-
ylcyclohexa-2,5-dienylidene)-2,3-
dimethylbenzene-1,4-
diamine Compound 55

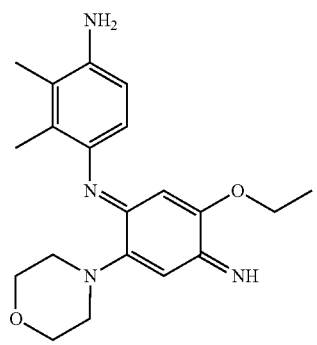

N-(5-Ethoxy-4-imino-2-morpholin-4-ylcyclohexa-2,5-dienylidene)-2,3-dimethylbenzene-1,4-diamine Compound 56

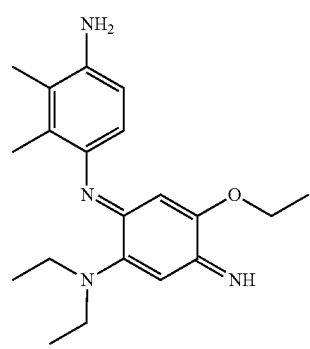

N-(2-Diethylamino-5-ethoxy-4-iminocyclohexa-2,5-dienylidene)-2,3-dimethylbenzene-1,4-diamine Compound 57

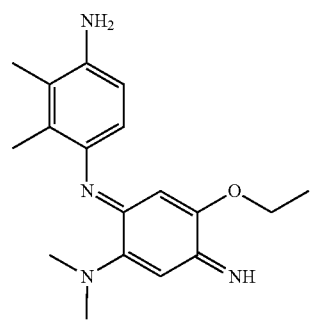

N-(2-Dimethylamino-5-ethoxy-4-iminocyclohexa-2,5-dienylidene)-2,3-dimethylbenzene-1,4-diamine Compound 58

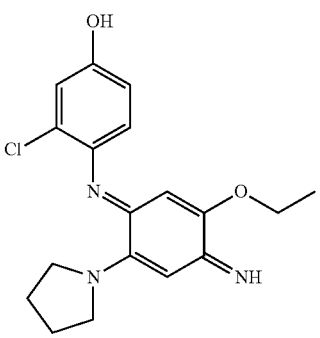

3-Chloro-4-(5-ethoxy-4-imino-2-pyrrolidin-1-ylcyclohexa-2,5-dienylideneamino)phenol Compound 59

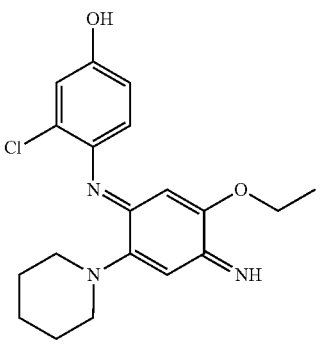

3-Chloro-4-(5-ethoxy-4-imino-2-piperidin-1-ylcyclohexa-2,5-dienylideneamino)phenol Compound 60

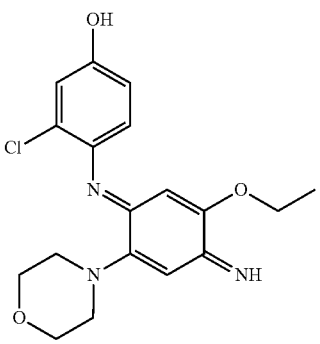

3-Chloro-4-(5-ethoxy-4-imino-2-morpholin-4-ylcyclohexa-2,5-dienylideneamino)phenol -continued

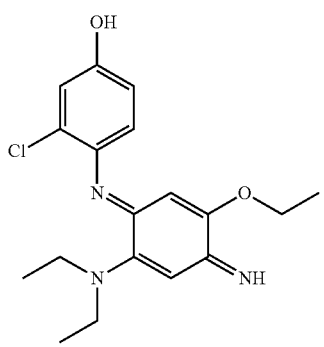

3-Chloro-4-(2-diethylamino-5-ethoxy-4-iminocyclohexa-2,5-dienylideneamino)phenol

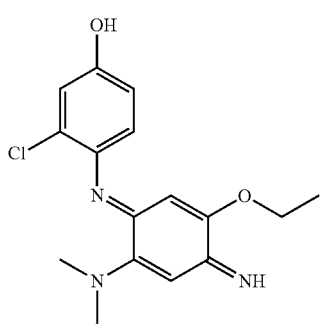

3-Chloro-4-(2-diethylamino-5-ethoxy-4-iminocyclohexa-2,5-dienylideneamino)phenol

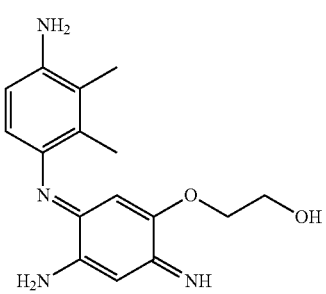

2-{4-Amino-3-[4-amino-2,3-dimethylphenylimino]-6-iminocyclohexa-1,4-dienyloxy}ethanol

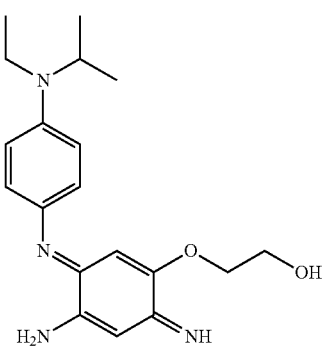

2-{4-Amino-3-[4-(ethylisopropylamino)phenylimino]-6-iminocyclohexa-1,4-dienyloxy}ethanol -continued Compound 61

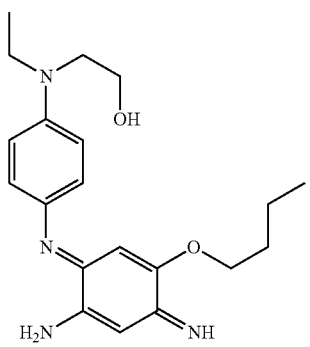

2-({4-[2-Amino-5-butoxy-4-iminocyclohexa-2,5-dienylideneamino]phenyl}ethylamino)ethanol Compound 62

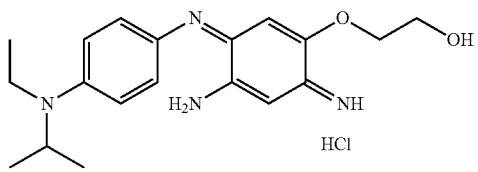

2-{4-amino-3-[4-(ethylisopropylamino)phenylimino]-6-iminocyclohexa-1,4-dienyloxy}ethanol Compound 63

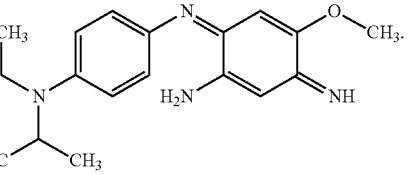

4-methoxy-6-[4-(N-ethyl-N-isopropylamino)phenylimino]-3-iminocyclohexa-1,4-dienyl-1-amine 3. A process for lightening keratin fibers, the process comprising:
applying to the keratin fibers:
(i) a dye composition comprising at least one azomethine compound of formula (I) to the fibers, which may be wet or dry, wherein the dye composition is free of oxidizing agent, and
(ii) a cosmetic composition comprising one or more oxidizing agents;
wherein compositions (i) and (ii) are applied to the said keratin fibers sequentially or simultaneously for a time that is sufficient to obtain a desired lightening:

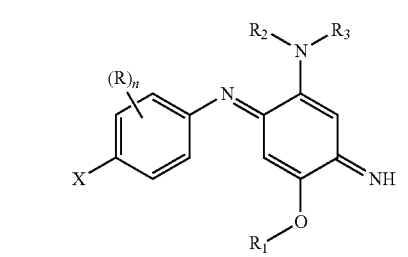

(I)

wherein:
n represents an integer equal to 0, 1, 2, 3 or 4,
R represents:
a linear or branched $C_1$-$C_4$ alkyl radical, optionally substituted with one or more identical or different radicals chosen from hydroxyl or imidazolium radicals, An⁻; An⁻ denoting a cosmetically acceptable anion or mixture of anions, a $C_1$-$C_4$ alkoxy radical, a halogen atom, $R_1$ represents:

a linear or branched $C_1$-$C_{10}$ alkyl radical, optionally substituted with one or more hydroxyl radicals, $R_2$ and $R_3$ represent independently of each other:

a hydrogen atom, a linear or branched $C_1$-$C_4$ alkyl radical, optionally substituted with one or more hydroxyl radicals, $R_2$ and $R_3$ may form, together with the nitrogen atom to which they are attached, a pyrrolidino, piperidino or morpholino ring, X represents:

a hydroxyl radical, a radical —$NR_4R_5$ in which $R_4$ and $R_5$ represent, independently of each other:

a hydrogen atom, a linear or branched $C_1$-$C_6$ alkyl radical, optionally substituted with one or more hydroxyl $C_1$-$C_4$ alkoxy radicals, it being understood that the compounds of formula (I) cannot represent the following compounds (A), (B), (C), (D) or (E):

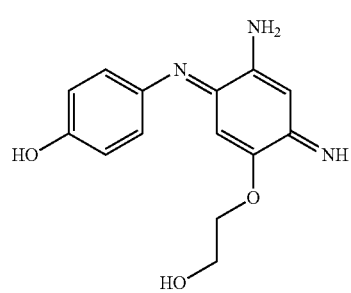

(A)

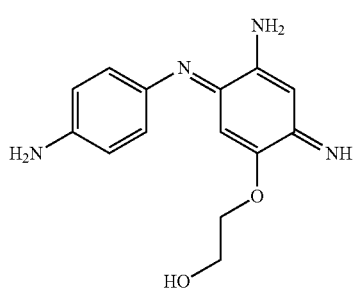

(B)

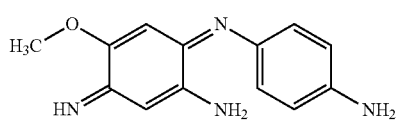

(C)

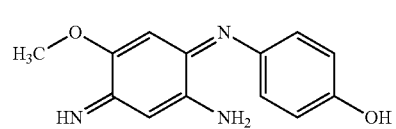

(D)

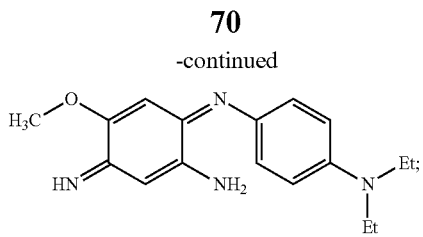

(E)

rinsing the keratin fibers, optionally washing the keratin fibers with shampoo;

optionally rinsing the keratin fibers again, and drying the keratin fibers or leaving the keratin fibers to dry.

4. A process for lightening keratin fibers, the process comprising:

applying to the keratin fibers:
(i) a dye composition comprising at least one azomethine compound of formula (II) to the fibers, which may be wet or dry, wherein (i) the dye composition is free of oxidizing agent, and
(ii) an oxidizing composition comprising one or more oxidizing agents, wherein compositions (i) and (ii) are applied to the keratin fibers sequentially or simultaneously for a time that is sufficient to obtain a desired lightening:

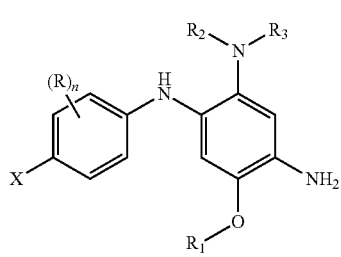

(II)

wherein:

n represents an integer equal to 0, 1, 2, 3 or 4,

R represents:

a linear or branched $C_1$-$C_4$ alkyl radical, optionally substituted with one or more identical or different radicals chosen from hydroxyl or imidazolium radicals, An⁻; An⁻ denoting a cosmetically acceptable anion or mixture of anions, a $C_1$-$C_4$ alkoxy radical, a halogen atom, $R_1$ represents:

a linear or branched $C_1$-$C_{10}$ alkyl radical, optionally substituted with one or more hydroxyl radicals, $R_2$ and $R_3$ represent, independently of each other:

a hydrogen atom, a linear or branched $C_1$-$C_4$ alkyl radical, optionally substituted with one or more hydroxyl radicals, $R_2$ and $R_3$ may form, together with the nitrogen atom to which they are attached, a pyrrolidino, piperidino or morpholino ring, X represents:

a hydroxyl radical, a radical —$NR_4R_5$ in which $R_4$ and $R_5$ represent, independently of each other:

a hydrogen atom, a linear or branched $C_1$-$C_6$ alkyl radical, optionally substituted with one or more hydroxyl $C_1$-$C_4$ alkoxy radicals;

rinsing the keratin fibers,
optionally washing the keratin fibers with shampoo;
optionally rinsing the keratin fibers again, and
drying the keratin fibers or leaving the keratin fibers to dry.

5. A multi-compartment device or dyeing kit comprising:
a first compartment containing a composition comprising at least one compound chosen from the following compounds, organic or mineral acid salts thereof, tautomeric forms, optical isomers or geometrical isomers thereof, or solvates thereof, wherein the composition is free of oxidizing agent:

Compound 1

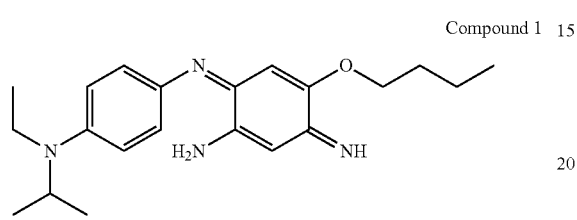

4-Butoxy-6-[4-(ethylisopropylamino)phenylimino]-3-iminocyclohexa-1,4-dienylamine Compound 2

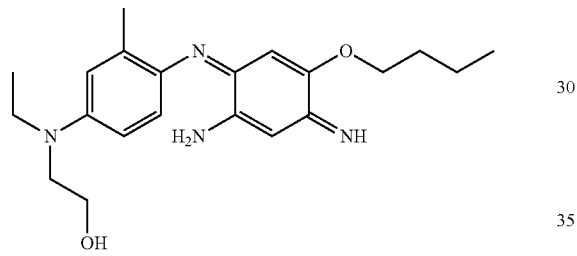

2-{[4-(2-Amino-5-butoxy-4-iminocyclohexa-2,5-dienylideneamino)-3-methylphenyl]ethylamino}ethanol Compound 3

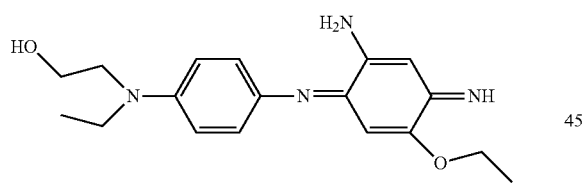

2-{[4-(2-Amino-5-ethoxy-4-iminocyclohexa-2,5-dienylideneamino)phenyl]ethylamino}ethanol Compound 4

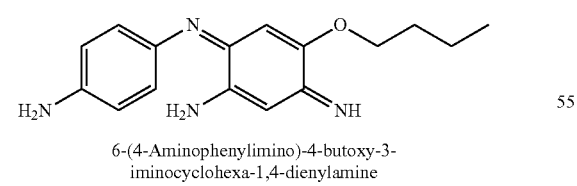

6-(4-Aminophenylimino)-4-butoxy-3-iminocyclohexa-1,4-dienylamine

Compound 5

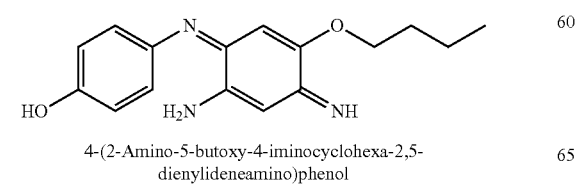

4-(2-Amino-5-butoxy-4-iminocyclohexa-2,5-dienylideneamino)phenol

Compound 6

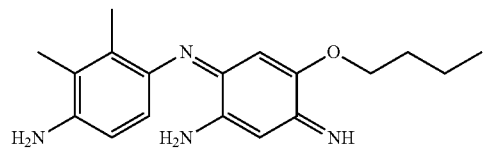

6-(4-Amino-2,3-dimethylphenylimino)-4-butoxy-3-iminocyclohexa-1,4-dienylamine

Compound 7

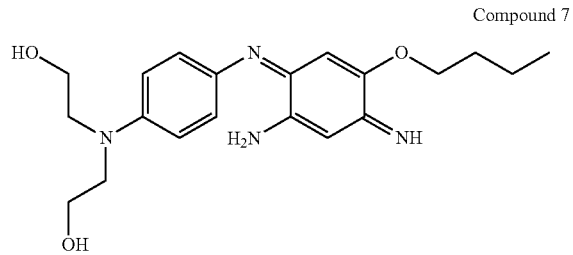

2-[[4-(2-Amino-5-butoxy-4-iminocyclohexa-2,5-dienylideneamino)phenyl](2-hydroxyethyl)amino]ethanol Compound 8

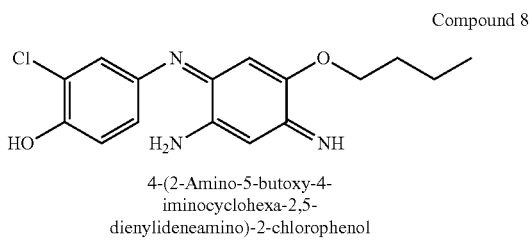

4-(2-Amino-5-butoxy-4-iminocyclohexa-2,5-dienylideneamino)-2-chlorophenol

Compound 9

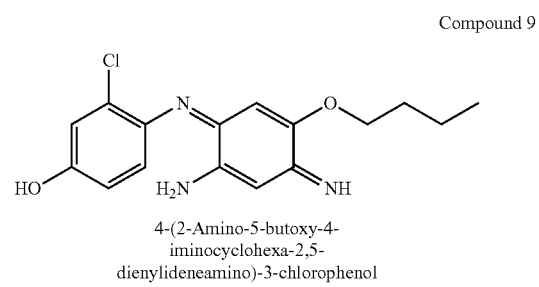

4-(2-Amino-5-butoxy-4-iminocyclohexa-2,5-dienylideneamino)-3-chlorophenol

Compound 10

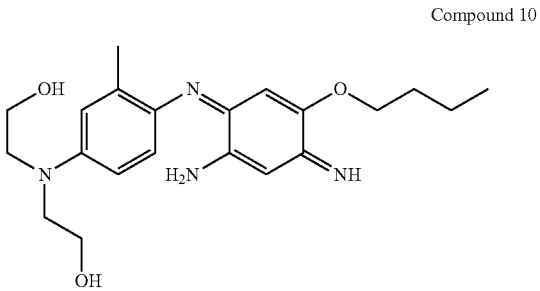

2-[[4-(2-Amino-5-butoxy-4-iminocyclohexa-2,5-dienylideneamino)-3-methylphenyl](2-hydroxyethyl)amino]ethanol Compound 11

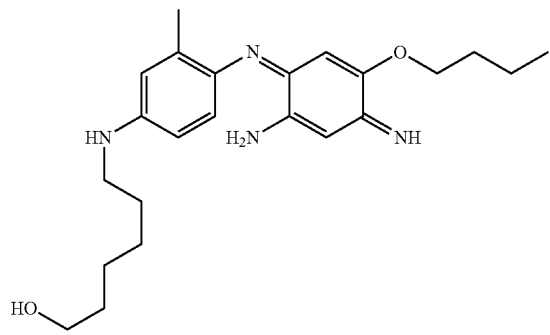

6-[4-(2-Amino-5-butoxy-4-
iminocyclohexa-2,5-
dienylideneamino)-3-
methylphenylamino]hexan-1-ol Compound 12

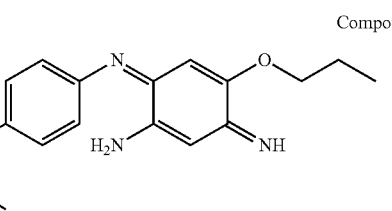

4-propoxy-6-[4-
(ethylisipropylamino)phenylimino]-
3-iminocyclohexa-1,4-dienylamine Compound 13

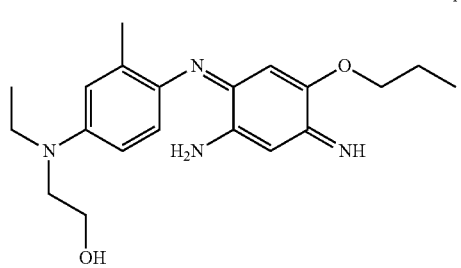

2-{[4-(2-Amino-5-propoxy-4-
iminocyclohexa-2,5-
dienylideneamino)-3-
methylphenyl]ethylamino}ethanol Compound 14

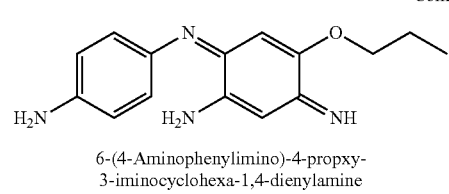

6-(4-Aminophenylimino)-4-propxy-
3-iminocyclohexa-1,4-dienylamine

Compound 15

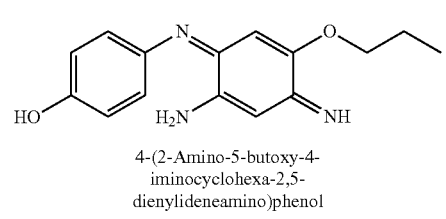

4-(2-Amino-5-butoxy-4-
iminocyclohexa-2,5-
dienylideneamino)phenol

Compound 16

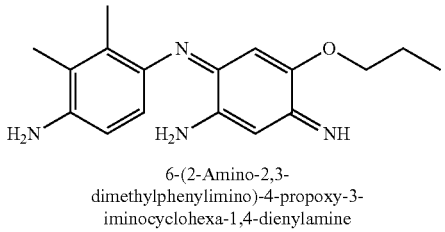

6-(2-Amino-2,3-
dimethylphenylimino)-4-propoxy-3-
iminocyclohexa-1,4-dienylamine Compound 17

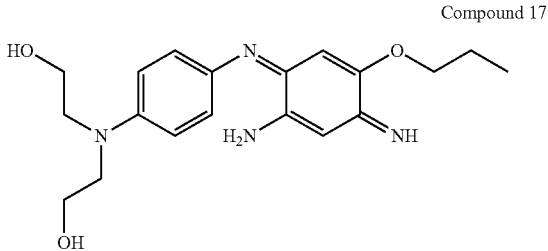

2-[[4-(2-Amino-5-propoxy-4-
iminocyclohexa-2,5-
dienylideneamino)phenyl](2-
hydroxyethyl)amino]ethanol Compound 18

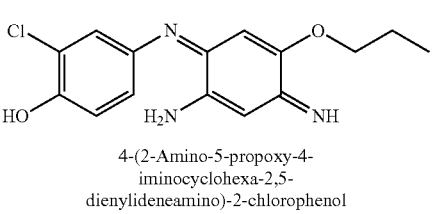

4-(2-Amino-5-propoxy-4-
iminocyclohexa-2,5-
dienylideneamino)-2-chlorophenol

Compound 19

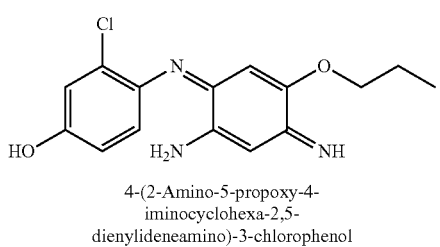

4-(2-Amino-5-propoxy-4-
iminocyclohexa-2,5-
dienylideneamino)-3-chlorophenol

Compound 20

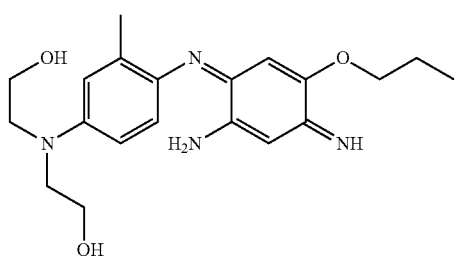

2-[[4-(2-Amino-5-propoxy-4-
iminocyclohexa-2,5-
dienylideneamino)-3-
methylphenyl](2-
hydroxyethyl)amino]
ethanol Compound 21

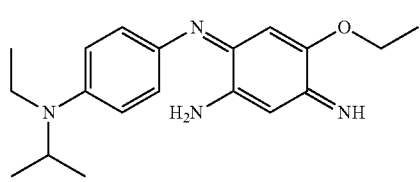

4-ethoxy-6-[4-(ethylisopropylamino)phenylimino]-3-iminocyclohexa-1,4-dienylamine Compound 22

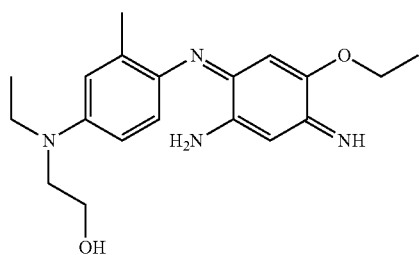

2-{[4-(2-Amino-5-ethoxy-4-iminocyclohexa-2,5-dienylideneamino)-3-methylphenyl]ethylamino}ethanol Compound 23

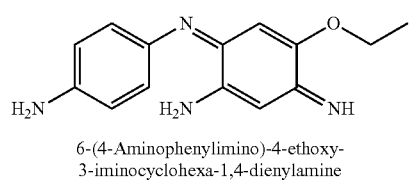

6-(4-Aminophenylimino)-4-ethoxy-3-iminocyclohexa-1,4-dienylamine

Compound 24

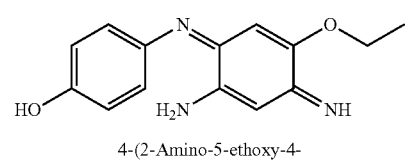

4-(2-Amino-5-ethoxy-4-iminocyclohexa-2,5-dienylideneamino)phenol

Compound 25

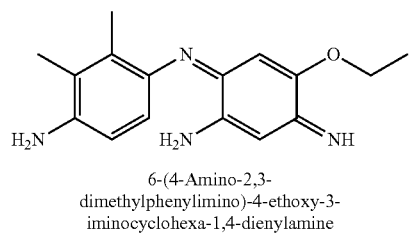

6-(4-Amino-2,3-dimethylphenylimino)-4-ethoxy-3-iminocyclohexa-1,4-dienylamine

Compound 26

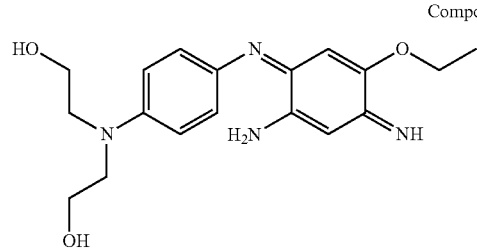

2-[[4-(2-Amino-5-ethoxy-4-iminocyclohexa-2,5-dienylideneamino)phenyl](2-hydroxyethyl)amino]ethanol Compound 27

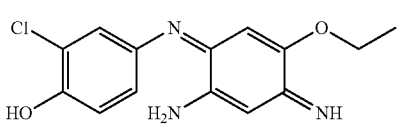

4-(2-Amino-5-ethoxy-4-iminocyclohexa-2,5-dienylideneamino)-2-chlorophenol

Compound 28

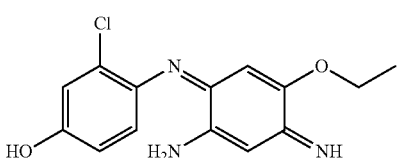

4-(2-Amino-5-ethoxy-4-iminocyclohexa-2,5-dienylideneamino)-3-chlorophenol

Compound 29

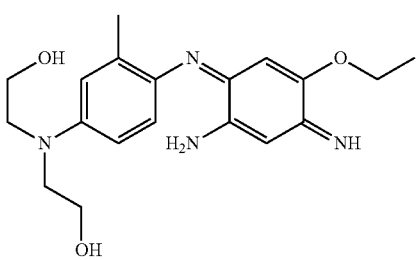

2-[[4-(2-Amino-5-ethoxy-4-iminocyclohexa-2,5-dienylideneamino)-3-methylphenyl](2-hydroxyethyl)amino]ethanol Compound 30

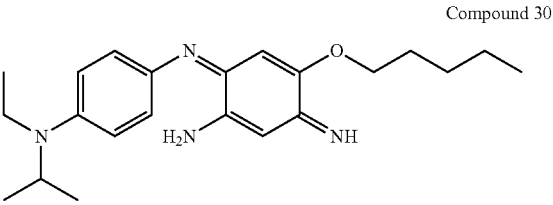

4-pentyloxy-6-[4-(ethylisopropylamino)phenylimino]-3-iminocyclohexa-1,4-dienylamine Compound 31

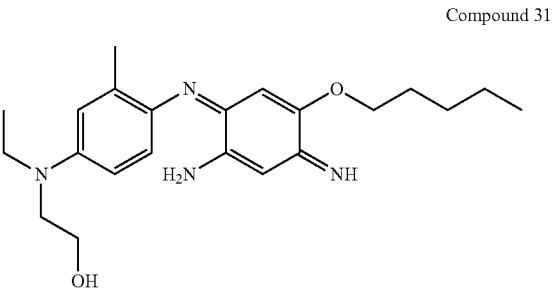

2-{[4-(2-Amino-5-pentyloxy-4-iminocyclohexa-2,5-dienylideneamino)-3-methylphenyl]ethylamino}ethanol Compound 32

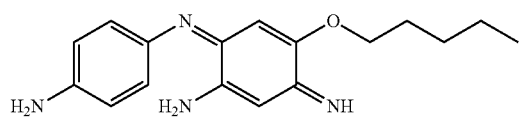

6-(4-Aminophenylimino)-4-
pentyloxy-3-iminocyclohexa-1,4-
dienylamine

Compound 33

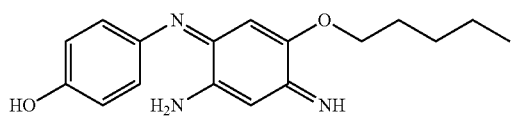

4-(2-Amino-5-pentyloxy-4-
iminocyclohexa-2,5-
dienylideneamino)phenol

Compound 34

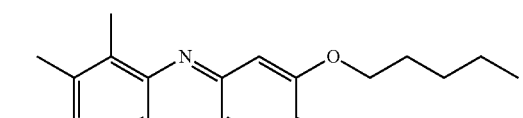

6-(4-Amino-2,3-
dimethylphenylimino)-4-pentyloxy-3-
iminocyclohexa-1,4-dienylamine Compound 35

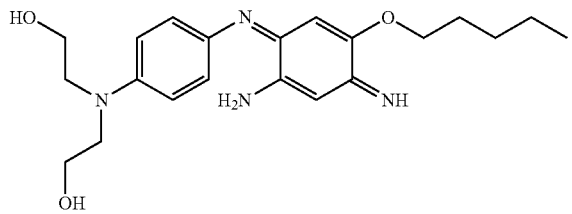

2-[[4-(2-Amino-5-pentyloxy-4-
iminocyclohexa-2,5-
dienylideneamino)phenyl(2-
hydroxyethyl)amino]ethanol Compound 36

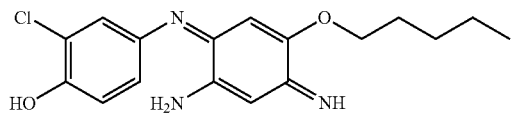

4-(2-Amino-5-pentyloxy-4-
iminocyclohexa-2,5-
dienylideneamino)-2-chlorophenol

Compound 37

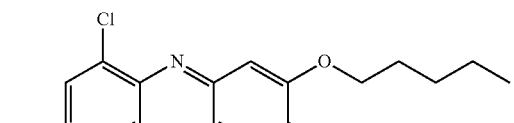

4-(2-Amino-5-pentyloxy-4-
iminocyclohexa-2,5-
dienylideneamino)-3-chlorophenol

Compound 38

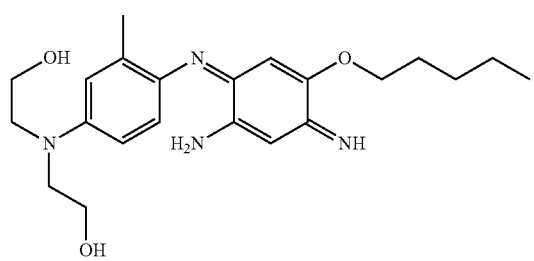

2-[[4-(2-Amino-5-pentyloxy-4-
iminocyclohexa-2,5-
dienylideneamino)-3-
methylphenyl](2-
hydroxyethyl)amino]ethanol Compound 39

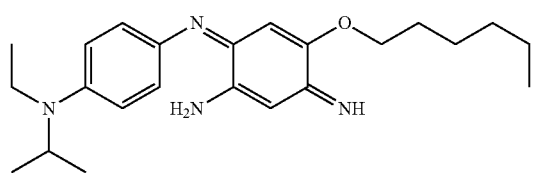

4-hexyloxy-6-[4-
(ethylisopropylamino)phenylimino]-3-
iminocyclohexa-1,4-dienylamine Compound 40

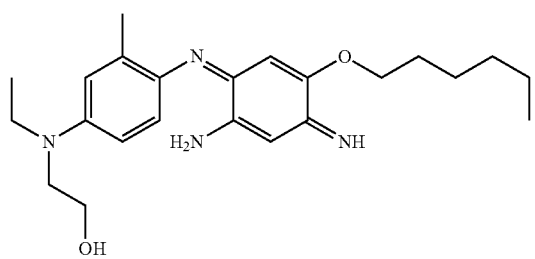

2-{[4-(2-Amino-5-hexyloxy-4-
iminocyclohexa-2,5-
dienylideneamino)-3-
methylphenyl]ethylamino}ethanol Compound 41

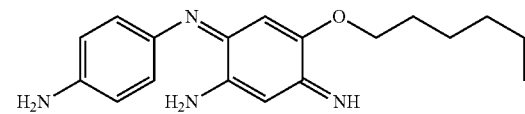

6-(4-Aminophenylimino)-4-hexyloxy-
3-
iminocyclohexa-1,4-dienylamine

Compound 42

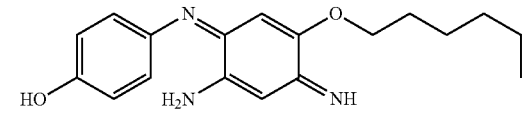

4-(2-Amino-5-hexyloxy-4-
iminocyclohexa-2,5-
dienylideneamino)phenol

-continued

Compound 43

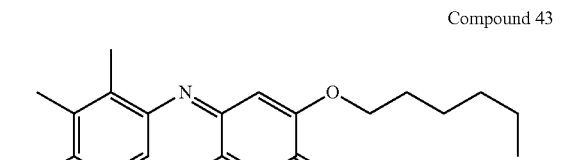

6-(4-Amino-2,3-
dimethylphenylimino)-4-hexyloxy-3-
iminocyclohexa-1,4-dienylamine Compound 44

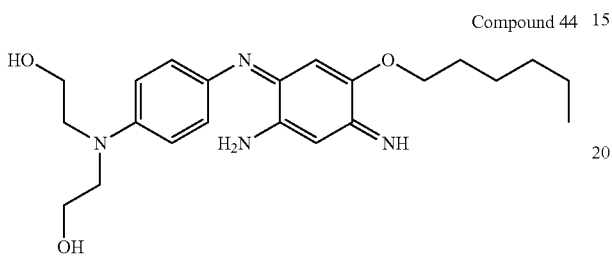

2-[[4-(2-Amino-5-hexyloxy-4-
iminocyclohexa-2,5-
dienylideneamino)phenyl(2-
hydroxyethyl)amino]ethanol Compound 45

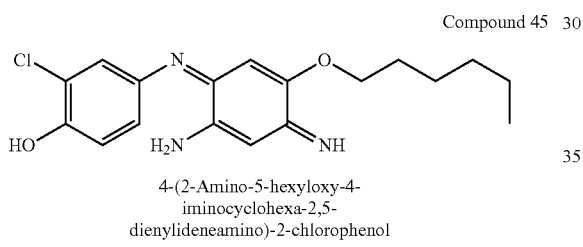

4-(2-Amino-5-hexyloxy-4-
iminocyclohexa-2,5-
dienylideneamino)-2-chlorophenol

Compound 46

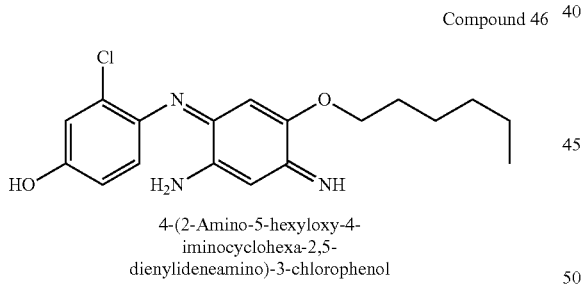

4-(2-Amino-5-hexyloxy-4-
iminocyclohexa-2,5-
dienylideneamino)-3-chlorophenol

Compound 47

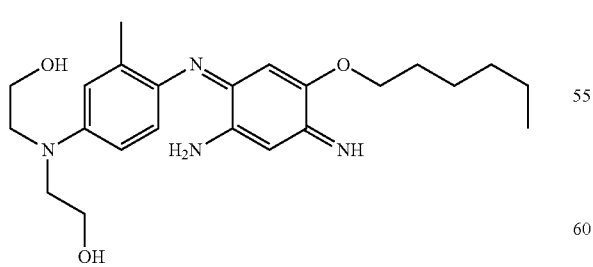

2-[[4-(2-Amino-5-hexyloxy-4-
iminocyclohexa-2,5-
dienylideneamino)-3-
methylphenyl](2-hydroxyethyl)amino]
ethanol -continued Compound 48

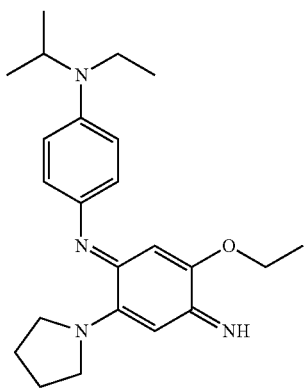

N-(5-Ethoxy-4-imino-2-pyrrolidin-1-
ylcyclohexa-2,5-dienylidene)-N'-
ethyl-N'-isopropylbenzene-1,4-
diamine Compound 49

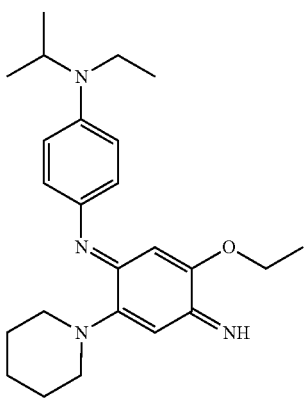

N-(5-Ethoxy-4-imino-2-piperidin-1-
ylcyclohexa-2,5-dienylidene)-N'-
ethyl-N'-isopropylbenzene-1,4-
diamine Compound 50

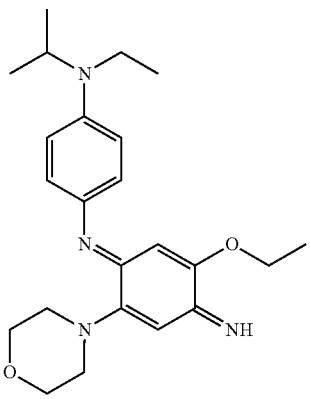

N-(5-Ethoxy-4-imino-2-morpholin-
4-ylcyclohexa-2,5-dienylidene)-N'-
ethyl-N'-isopropylbenzene-1,4-
diamine Compound 51

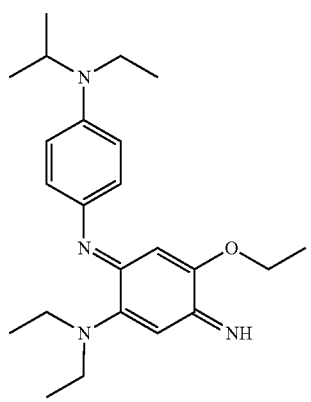

N-(2-Diethylamino-5-ethoxy-4-iminocyclohexa-2,5-dienylidene)-N'-ethyl-N'-isopropylbenzene-1,4-diamine Compound 54

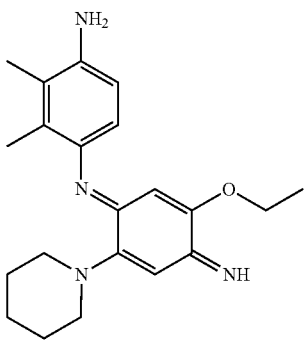

N-(5-Ethoxy-4-imino-2-piperidin-1-ylcyclohexa-2,5-dienylidene)-2,3-dimethylbenzene-1,4-diamine Compound 52

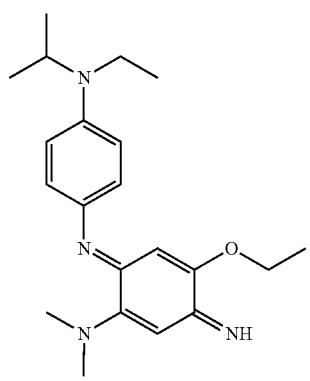

N-(2-methylamino-5-ethoxy-4-iminocyclohexa-2,5-dienylidene)-N'-ethyl-N'-isopropylbenzene-1,4-diamine Compound 55

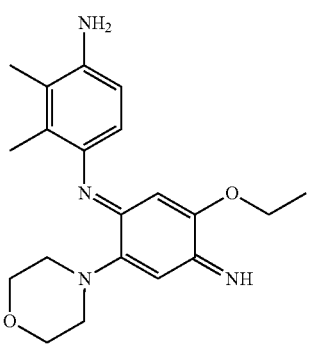

N-(5-Ethoxy-4-imino-2-morpholin-4-ylcyclohexa-2,5-dienylidene)-2,3-dimethylbenzene-1,4-diamine Compound 53

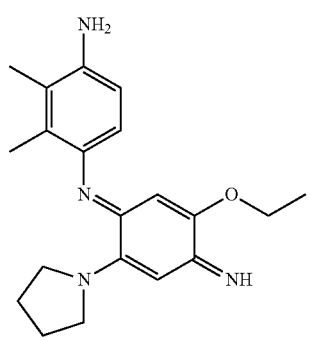

N-(5-Ethoxy-4-imino-2-pyrrolidin-1-ylcyclohexa-2,5-dienylidene)-2,3-dimethylbenzene-1,4-diamine Compound 56

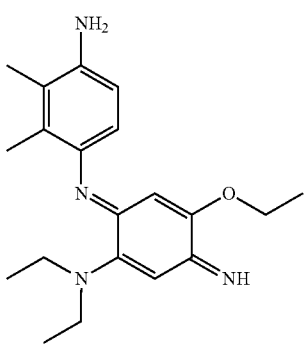

N-(2-Diethylamino-5-ethoxy-4-iminocyclohexa-2,5-dienylidene)-2,3-dimethylbenzene-1,4-diamine Compound 57

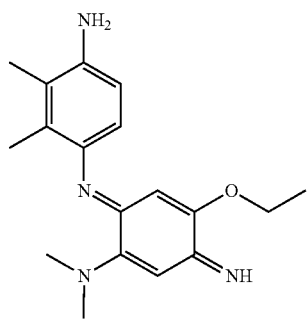

N-(2-Dimethylamino-5-ethoxy-4-iminocyclohexa-2,5-dienylidene)-2,3-dimethylbenzene-1,4-diamine Compound 58

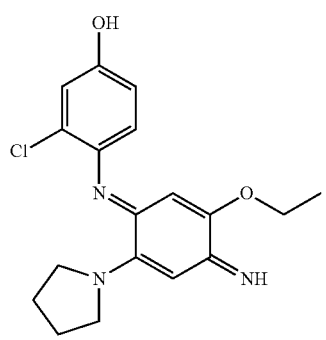

3-Chloro-4-(5-ethoxy-4-imino-2-pyrrolidin-1-ylcyclohexa-2,5-dienylideneamino)phenol Compound 59

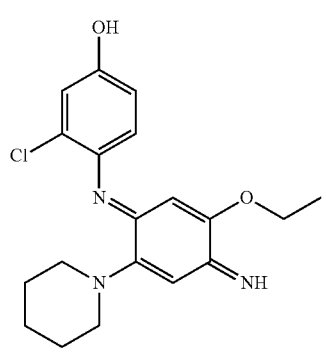

3-Chloro-4-(5-ethoxy-4-imino-2-piperidin-1-ylcyclohexa-2,5-dienylideneamino)phenol Compound 60

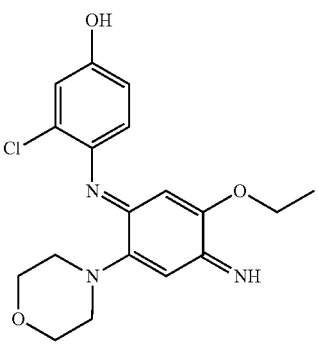

3-Chloro-4-(5-ethoxy-4-imino-2-morpholin-4-ylcyclohexa-2,5-dienylideneamino)phenol Compound 61

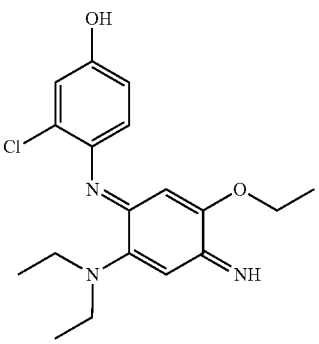

3-Chloro-4-(2-diethylamino-5-ethoxy-4-iminocyclohexa-2,5-dienylideneamino)phenol Compound 62

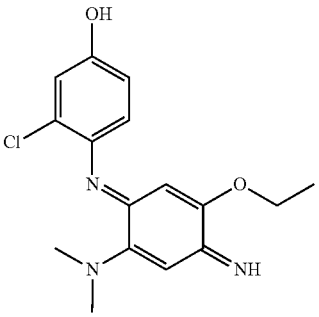

3-Chloro-4-(2-diethylamino-5-ethoxy-4-iminocyclohexa-2,5-dienylideneamino)phenol Compound 63

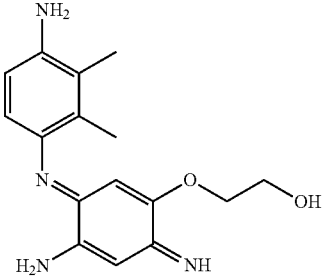

2-{4-Amino-3-[4-amino-2,3-dimethylphenylimino]-6-iminocyclohexa-1,4-dienyloxy}ethanol -continued Compound 64

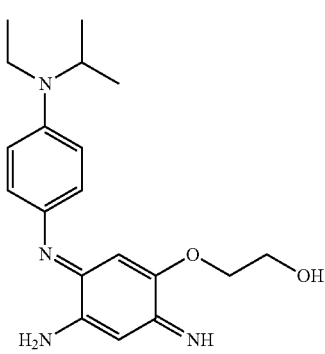

2-{4-Amino-3-[4-(ethylisopropylamino)phenylimino]-6-iminocyclohexa-1,4-dienyloxy}ethanol Compound 65

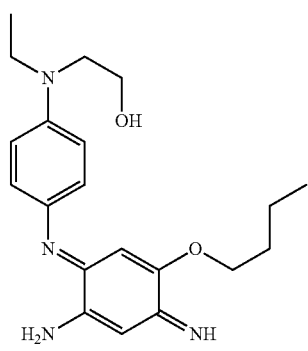

2-({4-[2-Amino-5-butoxy-4-iminocyclohexa-2,5-dienylideneamino]phenyl}ethylamino)ethanol Compound 66

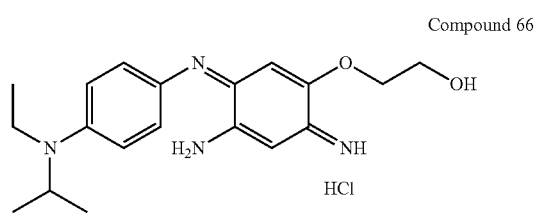

2-{4-amino-3-[4-(ethylisopropylamino)phenylimino]-6-iminocyclohexa-1,4-dienyloxy}ethanol Compound 67

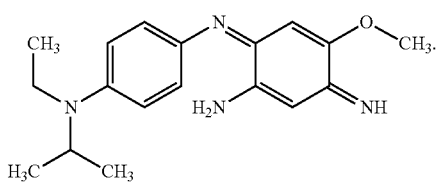

4-methoxy-6-[4-(N-ethyl-N-isopropylamino)phenylimino]-3-iminocyclohexa-1,4-dienyl-1-amine and a second compartment containing a composition comprising one or more oxidizing agents.

* * * * *

UNITED STATES PATENT AND TRADEMARK OFFICE
CERTIFICATE OF CORRECTION

PATENT NO. : 9,226,883 B2
APPLICATION NO. : 14/365211
DATED : January 5, 2016
INVENTOR(S) : Stephane Sabelle et al.

It is certified that error appears in the above-identified patent and that said Letters Patent is hereby corrected as shown below:

Claims

Column 41, line 29, claim 1, change "6-(2-Amino-" to -- 6-(4-Amino- --.

Column 56, line 42, claim 2, change "6-(2-Amino-" to -- 6-(4-Amino- --.

Signed and Sealed this
Nineteenth Day of April, 2016

Michelle K. Lee
*Director of the United States Patent and Trademark Office*